(12) United States Patent
Tobler

(10) Patent No.: US 7,605,134 B2
(45) Date of Patent: *Oct. 20, 2009

(54) 4"-DEOXY-4"-(S)-AMINO AVERMECTIN DERIVATIVES

(75) Inventor: Hans Tobler, Basel (CH)

(73) Assignee: Merial Limited, Duluth, GA (US)

( * ) Notice: Subject to any disclaimer, the term of this patent is extended or adjusted under 35 U.S.C. 154(b) by 657 days.

This patent is subject to a terminal disclaimer.

(21) Appl. No.: 10/488,225

(22) PCT Filed: Aug. 20, 2002

(86) PCT No.: PCT/EP02/09315

§ 371 (c)(1),
(2), (4) Date: Feb. 26, 2004

(87) PCT Pub. No.: WO03/020738

PCT Pub. Date: Mar. 13, 2003

(65) Prior Publication Data

US 2004/0248823 A1    Dec. 9, 2004

(30) Foreign Application Priority Data

Aug. 28, 2001   (CH) .................................. 1598/01

(51) Int. Cl.
*A61K 31/70* (2006.01)
*A61K 31/335* (2006.01)

(52) U.S. Cl. .......................... 514/30; 514/450

(58) Field of Classification Search ............ 514/30
See application file for complete search history.

(56) References Cited

U.S. PATENT DOCUMENTS

| | | | |
|---|---|---|---|
| 4,203,976 A | 5/1980 | Fisher et al. | |
| 4,206,205 A | 6/1980 | Mrozik et al. | |
| 4,427,663 A * | 1/1984 | Mrozik | 514/30 |
| 4,622,313 A | 11/1986 | Wyvratt, Jr. et al. | |
| 4,831,016 A | 5/1989 | Mrozik et al. | |
| 4,874,749 A * | 10/1989 | Mrozik | 514/30 |
| 4,895,837 A | 1/1990 | Mrozik et al. | |
| 5,023,241 A * | 6/1991 | Linn et al. | 514/30 |
| 5,057,499 A | 10/1991 | Mrozik et al. | |
| 5,169,839 A | 12/1992 | Linn et al. | |

(Continued)

FOREIGN PATENT DOCUMENTS

EP      001688      5/1979

(Continued)

OTHER PUBLICATIONS

PF Rolfe, KL Dawson, MD Soll, GK Nichols and WG Ryan, "Persistent efficacy of abamectin and doramectin against gastrointestinal nematodes of cattle", Australian Veterinary Journal, 1997, 75(1), 33-35.*

(Continued)

*Primary Examiner*—Johann R Richter
*Assistant Examiner*—Nathan W Schlientz
(74) *Attorney, Agent, or Firm*—Judy Jarecki-Black; Merial Limited; Thomas Kowalski, Esq.

(57) ABSTRACT

A description is given of compounds of the formula which in the 4"-position has the (S)-configuration and wherein $R_1$ is $C_1$-$C_{12}$alkyl, $C_3$-$C_8$cycloalkyl; or $C_2$-$C_{12}$alkenyl; $R_2$ is hydrogen, optionally substituted $C_1$-$C_{12}$alkyl or optionally substituted $C_2$-$C_{12}$alkenyl; $R_3$ is $C_1$-$C_{12}$alkyl, optionally substituted $C_1$-$C_{12}$alkyl, optionally substituted $C_1$-$C_{12}$alkoxy-$C_1$-$C_{12}$alkyl, optionally substituted $C_3$-$C_{12}$cycloalkyl, optionally substituted $C_2$-$C_{12}$alkenyl; optionally substituted $C_4$-$C_{12}$cycloalkenyl, optionally substituted $C_2$-$C_{12}$alkynyl; or $R_2$ and $R_3$ together are a three- to seven-membered alkylene or four- to seven-membered alkenylene bridge in each of which a $CH_2$ group may have been replaced by O, S or $NR_4$; X is O or S; $R_4$ is $C_1$-$C_8$alkyl, $C_3$-$C_8$cycloalkyl, $C_2$-$C_8$alkenyl, $C_2$-$C_8$alkynyl, benzyl or C(=O)—$R_5$; $R_5$ is for example H, OH, SH, $C_1$-$C_{12}$alkyl, $C_2$-$C_8$alkenyl, $C_2$-$C_8$alkynylyl or $C_1$-$C_{12}$haloalkyl; and, where appropriate, E/Z isomers, mixtures of E/Z isomers and/or tautomers thereof, in each case in free form or in salt form; to a process for the preparation of, and to the use of, such compounds and isomers and tautomers thereof; to starting compounds for the preparation of compounds of formula (I); to pesticidal compositions in which the active ingredient has been selected from the compounds of formula (I) and tautomers thereof; and to a method of controlling pests using such compositions.

(I)

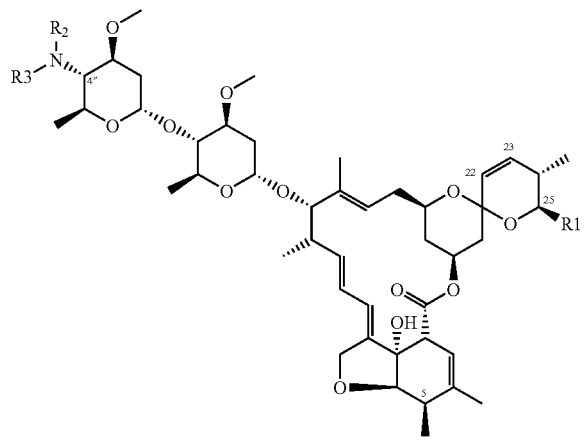

6 Claims, No Drawings

U.S. PATENT DOCUMENTS

| | | | |
|---|---|---|---|
| 5,192,546 | A | 3/1993 | Abercrombie et al. |
| 5,208,222 | A | 5/1993 | Meinke et al. |
| 5,229,415 | A | 7/1993 | Linn et al. |
| 5,346,698 | A | 9/1994 | Abercrombie et al. |
| 5,362,863 | A | 11/1994 | Cvetovich |
| 5,436,355 | A | 7/1995 | Demchak et al. |
| 5,945,445 | A | 8/1999 | Barringer et al. |
| 5,981,500 | A | 11/1999 | Bishop et al. |
| 6,605,595 | B1 | 8/2003 | Omura et al. |
| 6,875,727 | B2 | 4/2005 | Hofer et al. |
| 6,933,260 | B2 | 8/2005 | Piterna et al. |
| 7,250,402 | B2 | 7/2007 | Omura et al. |
| 7,378,399 | B2 | 5/2008 | Cassayre et al. |
| 2006/0140997 | A1 | 6/2006 | Pitterna et al. |
| 2006/0205595 | A1 | 9/2006 | Pitterna et al. |
| 2008/0051353 | A1 | 2/2008 | Jung et al. |

FOREIGN PATENT DOCUMENTS

| | | | |
|---|---|---|---|
| EP | 0089202 | | 9/1983 |
| EP | 0259688 | | 3/1988 |
| EP | 0266131 | | 5/1988 |
| EP | 0301806 | | 1/1989 |
| EP | 0340849 | | 11/1989 |
| EP | 0343708 | | 11/1989 |
| EP | 375393 | A1 * | 6/1990 |
| EP | 0411897 | | 6/1991 |
| EP | 0456509 | | 11/1991 |
| EP | 0465121 | | 1/1992 |
| EP | 0506331 | A | 9/1992 |
| EP | 0519731 | | 12/1992 |
| EP | 1160252 | A | 12/2001 |
| WO | WO 93/15099 | | 8/1993 |
| WO | WO 95/20877 | | 8/1995 |
| WO | WO 96/22300 | A1 | 7/1996 |
| WO | WO 02/068441 | | 9/2002 |
| WO | WO 02/068442 | | 9/2002 |
| WO | WO 03/020738 | | 3/2003 |
| WO | WO 03/053988 | A | 7/2003 |
| WO | WO 2004/067534 | | 8/2004 |

OTHER PUBLICATIONS

Mrozik et al.; *Bioinorganic & Medicinal Letters*, vol. 5, No. 20, pp. 2435-2440, 1995.

Fisher, *American Chemical Society Symposium*, 1997, vol. 658, "Phytochemicals for Pest Control", pp. 220-238, 1991.

Cvetovich et al., *J. Org. Chem.*, 1994, 59, pp. 7704-7708.

Search Report (SYN 118/2001).

U.S. Appl. No. 10/568,715, filed Feb. 17, 2006, Kasaba et al.
U.S. Appl. No. 10/560,390, filed Mar. 22, 2006, Pitterna et al.
U.S. Appl. No. 10/544,274, filed Aug. 3, 2005, Cassayre et al.
U.S. Appl. No. 10/544,281, filed Aug. 3, 2005, Quaranta et al.
U.S. Appl. No. 10/543,638, filed Jul. 28, 2005, Pitterna et al.
U.S. Appl. No. 10/543,643, filed Apr. 5, 2006, Pitterna et al.
U.S. Appl. No. 10/513,247, filed Nov. 2, 2004, Tobler et al.
U.S. Appl. No. 10/498,858, filed Jun. 14, 2004, Cassayre et al.
U.S. Appl. No. 11/319,686, filed Dec. 28, 2005, Pitterna et al.
U.S. Appl. No. 11/319,687, filed Dec. 28, 2005, Pitterna et al.
U.S. Appl. No. 10/539,274, filed Mar. 9, 2006, Maienfisch et al.

Yoshua et al.; Simultanious Determination of Residues of Emanectin and Its Metabolites, and Mibimectin, Ivermectin, and Abamectin in Crops by Liquid Chromatography w Fluorescence Detection. Journal of AOAC International vol. 84, No. 3 (910-917).

Wrzesinski et al, Isolation and Identification of Residues of 4"-(*epi*-Methylamino)-4"-deoxyavermectin B1a Benzoate from the Surface of Cabbage, Journal of Agricultural and Food Chemistry, vol. 44, 1996, pp. 304-312.

Meinke et al., "Affinity Probes for the Avermectin Binding Proteins", J Med Chem 1992, 35, 3879-3884.

Jones, T K et al.; "Synthesis and Biological Activity of 4a,4-Disubstituted Avermectins"; Journal of Agriculture and Food Chemistry., American Chemical Society, 42 1994, p. 1786-1790.

Meinke et al. "Synthesis of Avermectin B1-4'-4'a -oxide; A Precursor to Potent Antihelmintic agents", Biorganic Medicinal Chemistry Letters, vol. 2, 1992 p. 537.

Mrozik, H et al. "Avermectin Acyl Derivatives with Anti helmintic activity" Journal of Medicinal Chemistry, vol. 25, 1982, pp. 658-663.

Shoop et al Efficacy in Sheep and Pharmacokinetics in Cattle That Led to the Selection of Epinomectin as a Topical Endetocide for Cattle, International Journal for Parasitology, 1996, 26 (11), 1227-35.

* cited by examiner

4"-DEOXY-4"-(S)-AMINO AVERMECTIN DERIVATIVES

This application is a 371 filing of International Application No. PCT/EP02/09315, filed Aug. 20, 2002, the contents of which are incorporated herein by reference.

The invention relates to (1) a compound of formula

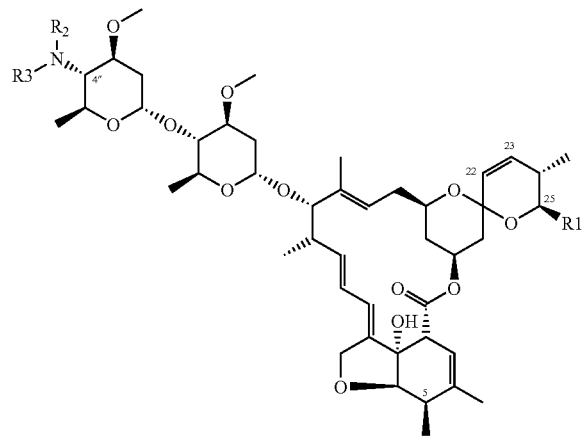

(I)

which in the 4"-position has the (S)-configuration and wherein $R_1$ is $C_1$-$C_{12}$alkyl, $C_3$-$C_8$cycloalkyl; or $C_2$-$C_{12}$alkenyl;

$R_2$ is hydrogen, unsubstituted or mono- to penta-substituted $C_1$-$C_{12}$alkyl or unsubstituted or mono- to penta-substituted $C_2$-$C_{12}$alkenyl;

$R_3$ is $C_1$-$C_{12}$alkyl, mono- to penta-substituted $C_1$-$C_{12}$alkyl, unsubstituted or mono- to penta-substituted $C_1$-$C_{12}$alkoxy-$C_1$-$C_{12}$alkyl, unsubstituted or mono- to penta-substituted $C_3$-$C_{12}$cycloalkyl, unsubstituted or mono- to penta-substituted $C_2$-$C_{12}$alkenyl; unsubstituted or mono- to penta-substituted $C_4$-$C_{12}$cycloalkenyl, unsubstituted or mono- to penta-substituted $C_2$-$C_{12}$alkynyl; or $R_2$ and $R_3$ together are a three- to seven-membered alkylene or four- to seven-membered alkenylene bridge in each of which a $CH_2$ group may have been replaced by O, S or $NR_4$;

wherein the substituents of the mentioned alkyl, alkoxyalkyl, alkenyl, alkynyl, alkylene, alkenylene, cycloalkyl and cycloalkenyl radicals are selected from the group consisting of OH, halogen, halo-$C_1$-$C_2$alkyl, CN, SCN, $NO_2$, Si($C_1$-$C_{12}$alkyl)$_3$, $C_2$-$C_6$alkynyl, $C_3$-$C_8$cycloalkyl that is unsubstituted or substituted by from one to three methyl groups, norbornylenyl, $C_3$-$C_8$cycloalkenyl that is unsubstituted or substituted by from one to three methyl groups; $C_3$-$C_8$halocycloalkyl, $C_1$-$C_{12}$alkoxy, $C_1$-$C_6$alkoxy-$C_1$-$C_6$alkoxy, $C_3$-$C_8$cycloalkoxy, $C_1$-$C_{12}$haloalkoxy, $C_1$-$C_{12}$alkylthio, $C_3$-$C_8$cycloalkylthio, $C_1$-$C_{12}$haloalkylthio, $C_1$-$C_{12}$alkylsulfinyl, $C_3$-$C_8$cycloalkylsulfinyl, $C_1$-$C_{12}$haloalkylsulfinyl, $C_3$-$C_8$halocycloalkylsulfinyl, $C_1$-$C_{12}$alkylsulfonyl, $C_3$-$C_8$cycloalkylsulfonyl, $C_1$-$C_{12}$haloalkylsulfonyl, $C_3$-$C_8$halocycloalkylsulfonyl, $C_2$-$C_8$alkenyl, $C_2$-$C_8$alkynyl, $NH_2$, NH($C_1$-$C_6$alkyl), NH(hydroxy-$C_1$-$C_6$alkyl), N($C_1$-$C_6$alkyl)(hydroxy-$C_1$-$C_6$alkyl), N(phenyl)(hydroxy-$C_1$-$C_6$alkyl), N($C_1$-$C_6$alkyl)$_2$, —C(=X)Z$R_5$, —O—C(=X)$R_6$, —O—C(=X)N($R_8$)$R_6$, —NHC(=X)$R_6$, —NHC(=X)O$R_6$, —NHC(=X)S$R_6$, —NHC(=X)N($R_8$)$R_6$, —S—C(=S)$R_6$, —NHS(O)$_2$—$R_9$, —P(=O)(O$C_1$-$C_6$alkyl)$_2$;

aryl, heterocyclyl, aryloxy, arylthio, heterocyclyloxy; and aryl, heterocyclyl, aryloxy, arylthio and heterocyclyloxy which, depending on the possibilities for substitution on the ring, are mono- to penta-substituted by substituents selected from the group consisting of OH, =O, halogen, CN, $NO_2$, $C_1$-$C_{12}$alkyl, hydroxy$C_1$-$C_{12}$alkyl, $C_3$-$C_8$cycloalkyl, $C_1$-$C_{12}$haloalkyl, $C_1$-$C_{12}$alkoxy, $C_1$-$C_{12}$haloalkoxy, $C_1$-$C_{12}$alkylthio, $C_1$-$C_{12}$haloalkylthio, $C_1$-$C_6$alkoxy-$C_1$-$C_6$alkyl, dimethylamino-$C_1$-$C_6$alkoxy, $C_2$-$C_8$alkenyl, $C_2$-$C_8$alkynyl, Si($C_1$-$C_{12}$alkyl)$_3$, methylenedioxy, —C(=X)$R_5$, —O—C(=X)$R_6$, —$CH_2$—C(=O)$R_5$, —$CH_2$—O—C(=O)Rr, —NH—C(=X)$R_6$, —S—C(=S)$R_6$, $NH_2$, NH($C_1$-$C_{12}$alkyl), —N($C_1$-$C_{12}$alkyl)$_2$, $C_1$-$C_6$alkylsulfinyl, $C_3$-$C_8$cycloalkylsulfinyl, $C_1$-$C_6$haloalkylsulfinyl, $C_3$-$C_8$halocycloalkylsulfinyl, $C_1$-$C_6$alkylsulfonyl, $C_3$-$C_8$cycloalkylsulfonyl, $C_1$-$C_6$haloalkylsulfonyl and $C_3$-$C_8$halocycloalkylsulfonyl; unsubstituted phenyl, phenoxy, phenyl-$C_1$-$C_6$alkyl, phenyl-$C_1$-$C_6$alkoxy, phenyl-$C_2$-$C_6$alkenyl, phenyl-$C_2$-$C_6$alkynyl; phenyl, phenoxy, phenyl-$C_1$-$C_6$alkyl, phenyl-$C_1$-$C_6$alkoxy, phenyl-$C_2$-$C_6$alkenyl and phenyl-$C_2$-$C_6$alkynyl, each of which is substituted in the phenylring by from one to three substituents independently selected of one another from nitro, cyano, halogen, $C_1$-$C_{12}$alkoxy, halo$C_1$-$C_{12}$alkyl and halo$C_1$-$C_{12}$alkoxy;

X is O or S;

Z is a bond, O, $NR_8$ or S;

$R_4$ is $C_1$-$C_8$alkyl, $C_3$-$C_8$cycloalkyl, $C_2$-$C_8$alkenyl, $C_2$-$C_8$alkynyl, benzyl or —C(=O)—$R_5$;

$R_5$ is H, OH, SH, $C_1$-$C_{12}$alkyl, $C_2$-$C_8$alkenyl, $C_2$-$C_8$alkynylyl, $C_1$-$C_{12}$haloalkyl, $C_2$-$C_8$haloalkenyl, $C_1$-$C_6$alkoxy-$C_1$-$C_6$alkyl, —$C_1$-$C_6$S(O)$_2$—$R_9$, $C_1$-$C_6$alkyl which is mono- or disubstituted with substituents selected from COOH, —C(=O)O—$CH_2$-phenyl, unsubstituted or substituted phenyl, unsubstituted or substituted biphenyl, wherein the substituents are selected from cyano, halogen, nitro, trifluoromethyl, trifluoromethyl and benzyloxy; aryl, heterocyclyl, aryl-$C_1$-$C_{12}$alkyl, aryloxy-$C_1$-$C_{12}$alkyl, —$C_1$-$C_6$alkyl-C(=O)—$R_7$, —$C_1$-$C_6$alkyl-C(=O)—$R_7$; or aryl, heterocyclyl, aryl-$C_1$-$C_{12}$alkyl, aryloxy-$C_1$-$C_{12}$alkyl, each of which is substituted on the aromatic ring by from one to three substituents selected independently of one another from halogen, nitro, cyano, $C_1$-$C_6$alkoxy, $C_1$-$C_6$haloalkyl and $C_1$-$C_6$haloalkoxy;

$R_6$ is H, $C_1$-$C_{24}$alkyl, $C_1$-$C_6$alkoxy-$C_1$-$C_6$alkyl, $C_1$-$C_{12}$hydroxyalkyl, $C_1$-$C_{12}$haloalkyl, $C_2$-$C_8$alkenyl, $C_2$-$C_8$alkynyl, $C_3$-$C_8$cycloalkyl, —$C_1$-$C_6$S(O)$_2$—$R_9$, aryl or phenyl-$C_1$-$C_6$alkyl; wherein the phenyl- and aryl-radicals may carry from one to three substituents selected independently of one another from nitro, cyano, halogen, $C_1$-$C_6$alkyl, $C_1$-$C_6$alkoxy, $C_1$-$C_6$haloalkyl and $C_1$-$C_6$haloalkoxy;

$R_7$ is H, OH, $C_1$-$C_{12}$alkyl, $C_1$-$C_{12}$alkoxy, $C_1$-$C_6$alkoxy-$C_1$-$C_6$alkoxy, $C_2$-$C_8$alkenyloxy, phenyl, phenoxy, benzyloxy, $NH_2$, NH($C_1$-$C_{12}$alkyl), N($C_1$-$C_{12}$alkyl)$_2$, —NH-phenyl or —N($C_1$-$C_{12}$alkyl)-phenyl;

$R_8$ is H, $C_1$-$C_{12}$alkyl, phenyl or benzyl; and $R_9$ H, $C_1$-$C_{12}$alkyl, aryl, aryl-$C_1$-$C_{12}$alkyl, or aryl or aryl-$C_1$-$C_{12}$alkyl wherein the aryl radical may carry from one to three substituents selected independently of one another from nitro, cyano, halogen, $C_1$-$C_6$alkyl, $C_1$-$C_6$alkoxy, $C_1$-$C_6$haloalkyl and $C_1$-$C_6$haloalkoxy;

and, where appropriate, E/Z isomers, mixtures of E/Z isomers and/or tautomers thereof, in each case in free form or in salt form;

to a process for the preparation of, and to the use of, such compounds and isomers and tautomers thereof; to starting compounds for the preparation of compounds of formula (I); to pesticidal compositions in which the active ingredient has been selected from the compounds of formula (I) and tautomers thereof; and to a method of controlling pests using such compositions.

Certain macrolide compounds are proposed for pest control in the literature. The biological properties of those known compounds are not entirely satisfactory, however, for which reason there is a need to provide further compounds having pesticidal properties, especially for the control of insects and representatives of the order Acarina. That problem is solved, in accordance with the invention, by the provision of the present compounds of formula (I), wherein the (S)-configuration applies in the 4"-position.

The compounds claimed in accordance with the invention are derivatives of avermectin. Avermectins are known to the person skilled in the art. They are a group of pesticidally active compounds, closely related to one another structurally, that are obtained by fermentation of a strain of the *Streptomyces* avermitilis microorganism. Derivatives of avermectins can be obtained via conventional chemical syntheses.

The avermectins obtainable from *Streptomyces* avermitilis are designated A1a, A1b, A2a, A2b, B1a, B1b, B2a and B2b. Compounds with the designation "A" have a methoxy radical in the 5-position; those compounds designated "B" have an OH group. The "a" series comprises compounds wherein the substituent $R_1$ (in position 25) is a sec-butyl radical; the "b" series have an isopropyl radical in the 25-position. The number 1 in the name of a compound indicates that atoms 22 and 23 are bonded by a double bond; the number 2 indicates that they are bonded by a single bond and carbon atom 23 carries an OH group. The above designations are retained in the description of the present invention, in order to indicate the specific structural type—in the case of the non-natural avermectin derivatives according to the invention—that corresponds to natural avermectin. In accordance with the invention there are claimed derivatives of compounds of the B1 series, more especially mixtures of derivatives of avermectin B1a and avermectin B1b wherein the (S)-configuration applies in the 4"-position.

Some of the compounds of formula (I) may be in the form of tautomers. Accordingly, any reference to the compounds of formula (I) hereinbefore and hereinafter is to be understood, where applicable, as including also corresponding tautomers, even if the latter are not specifically mentioned in every case.

The compounds of formula (I) and, where appropriate, tautomers thereof are capable of forming salts, for example acid addition salts. Those acid addition salts are formed, for example, with strong inorganic acids, such as mineral acids, e.g. sulfuric acid, a phosphoric acid or a hydrohalic acid, with strong organic carboxylic acids, such as unsubstituted or substituted, e.g. halo-substituted, $C_1$-$C_4$alkanecarboxylic acids, saturated or unsaturated dicarboxylic acids, hydroxycarboxylic acids, or with organic sulfonic acids, such as unsubstituted or substituted, e.g. halo-substituted, $C_1$-$C_4$alkane- or aryl-sulfonic acids. Furthermore, compounds of formula (I) having at least one acid group are capable of forming salts with bases. Suitable salts with bases are, for example, metal salts, such as alkali metal and alkaline earth metal salts, e.g. sodium, potassium and magnesium salts, and salts with ammonia or an organic amine, such as morpholine, piperidine, pyrrolidine, a mono-, di- or tri-lower alkylamine, e.g. ethyl-, diethyl-, triethyl- or dimethyl-propyl-amine, or a mono-, di- or tri-hydroxy-lower alkylamine, e.g. mono-, di- or tri-ethanolamine. In addition, corresponding internal salts may, where appropriate, also be formed. Preference is given, firstly, to the free form. Among the salts of compounds of formula (I) preference is given to agrochemically advantageous salts. The free compounds of formula (I) and salts thereof are to be understood hereinbefore and hereinafter as including, where appropriate, both the corresponding salts and the free compounds of formula (I), respectively. The same is correspondingly true for tautomers of compounds of formula (I) and salts thereof.

Preferred anions of salts of compounds of formula (I) are the anion of a mineral acid, for example of sulfuric acid, a phosphoric acid or a hydrohalic acid;

the anion of an organic carboxylic acid, for example an unsubstituted or substituted, e.g. halo-substituted, $C_1$-$C_4$alkanecarboxylic acid, a saturated or unsaturated dicarboxylic acid, or a hydroxycarboxylic acid, the anion of an organic sulfonic acid, for example an unsubstituted or substituted, e.g. halo-substituted, $C_1$-$C_4$alkane- or aryl-sulfonic acid; or the anion of an active-H—C compound. Such active-H—C compounds especially include organic compounds that carry strongly electron-withdrawing substituents, for example nitriles, carbonyls or nitro groups. Preference is given to anions of compounds of formula $Y_1$—$CH_2$—$Y_2$ wherein $Y_1$ and $Y_2$ denote an electron-withdrawing group, with special preference being given to the anions of malodinitrile, cyanoacetic acid, esters of cyanoacetic acid, amides of cyanoacetic acid, acetoacetic acid, esters of acetoacetic acid, acetylacetone, cyanoacetone and barbituric acid; or the anion of an acidic phenol, for example picric acid.

Very special preference is given to 1:1 salts of compounds of formula (I) with the following acids: benzoic acid, maleic acid, fumaric acid, 2-hydroxybenzoic acid, salicylic acid, thiosalicylic acid, malic acid, benzenesulfonic acid, barbituric acid, 2-ethylbutyric acid, thiomalic acid, 3,5-dihydroxybenzoic acid, trimesic acid, D-(−)-quinic acid, 2-bromo-benzoic acid, 2-phenyl-benzoic acid, 3,3'-thiodipropionic acid, naphthalene-1-carboxylic acid, 5-sulfosalicylic acid, 2-methoxy-phenylacetic acid, benzene-1,2,4-tricarboxylic acid, 3-hydroxybenzoic acid, D-gluconic acid, 4,5-dichloro-phthalic acid, n-hexanoic acid (caproic acid), n-heptanoic acid (oenanthic acid), n-octanoic acid (caprylic acid), stearic acid, palmitic acid, 2,2'-dihydroxy-1,1'-dinaphthylmethane-3,3'-4,4'-methylene-bis(3-hydroxy-2-naphthoic acid), embonic acid, 4-methoxy-phenylacetic acid (homoanisic acid), 2-anisic acid (2-methoxybenzoic acid), adamantane-1-carboxylic acid, pyridine-3,4-dicarboxylic acid, 3,4-dihydroxy-benzoic acid, 1-hydroxy-2-naphthoic acid (1-naphthol-2-carboxylic acid), 2,2'-oxydiacetic acid (diglycolic acid), O-ethyl-glycolic acid, (2-naphthylthio)-acetic acid (S-(2-naphthyl)-thioglycolic acid), 2-naphthoxy-acetic acid, perfluoro-octanoic acid, p-toluic acid, cyclohexanepropionic acid, 2,6-dihydroxypyridine-4-carboxylic acid (citrazinic acid), 3-methoxypropionic acid, 3,4,5-trihydroxy-benzoic acid (gallic acid), pyromucic acid (furan-2-carboxylic acid), 2-methylbenzoic acid (o-toluic acid), 3,6,9-trioxa-undecanedioic acid, 3-(4-methoxyphenyl)-propionic acid (p-methoxy-hydrocinnamic acid), 3-(3,4-dihydroxyphenyl)-propionic acid, O-acetylsalicylic acid (aspirin), 3-fluoro-benzoic acid, cyclohexanecarboxylic acid, 5-chloro-2-hydroxybenzoic acid (5-chloro-salicylic acid), 2,5-dimethyl-benzoic acid (p-xylylic acid), 3,4,5-trimethoxy-benzoic acid (trimethylgallic acid), 2,4,6-trimethyl-benzoic acid, 3-phenoxy-benzoic acid, 4-phenyl-butyric acid, 3-trifluoromethyl-benzoic acid, terephthalic acid monomethyl ester, o-hydroxy-phenyl-acetic acid, isophthalic acid, 2,4,6-trihydroxy-benzoic acid, trifluoromethanesulfonic acid, 2-methyl-propionic acid (isobutyric acid), 2,4-dimethoxy-benzoic acid, 2-thienylacetic acid (thiophene-2-acetic acid), 3,4-dimethoxy-benzoic acid (veratric acid), 2,2-bis(hydroxymethyl)-propionic acid, 2-fluoro-phenylacetic acid, 2-methyl-butyric acid, hydroxy-acetic acid, 4-chloro-phenylacetic acid, 2-mercaptobenzoic acid (thiosalicylic acid), (+/−)-2-hydroxyphenyl-acetic acid (DL-mandelic acid), 2,4-dihydroxypyrimidine-6-carboxylic acid, toluene-4-sulfonic acid, (p-toluene-sulfonic acid), 2-chloro-phenylacetic acid, 2,4-dichloro-benzoic acid, 2,6-dichloro-benzoic acid, 2-mercapto-propionic acid (thiolactic acid), 2-chloro-benzoic acid, methanesulfonic acid, ethanesulfonic acid (ethyl-sulfuric acid), 4-phenoxy-butyric acid, 4-tert-butyl-benzoic acid, 3,4-methylenedioxy-benzoic acid, bis(2-carboxyethyl)-disulfide, pivalic acid (trimethylacetic acid), nicotinic acid N-oxide, acrylic acid, 3-benzoylpropionic acid (4-oxo-4-phenyl-butyric acid), (1R)-(−)-camphor-10-sulfonic acid hydrate, 2-chloro-4-fluoro-benzoic acid, 3,5-dimethoxy-benzoic acid, 2-sulfobenzoic acid, sulfoacetic acid, 2-chloro-6-fluoro-benzoic acid, 2,4-dihydroxy-benzoic acid, methoxyacetic acid, 2,4,6-trimethyl-benzene-sulfonic acid, tartaric acid, xanthene-9-carboxylic acid, 4-pentenoic acid (allylacetic acid), 5-sulfosalicylic acid, vinylacetic acid, 2-butynedioic acid (acetylenedicarboxylic acid), 2-oxo-propionic acid (pyruvic acid), cyclohexylacetic acid, 2-hydroxyisobutyric acid, nicotinic acid, 6-chloro-nicotinic acid, isonicotinic acid, picolinic acid, pyrazinecarboxylic acid, oxalic acid, propionic acid, pentafluoropropionic acid, butyric acid, heptafluorobutyric acid, valeric acid, citric acid, glyceric acid, acetic acid, chloroacetic acid, dichloroacetic acid, trifluoroacetic acid, fluoroacetic acid, lactic acid, malonic acid, succinic acid, glutaric acid, adipic acid, pimelic acid, suberic acid, azelaic acid, sebacic acid, phthalic acid, terephthalic acid, phosphoric acid, sulfuric acid, hydrochloric acid, hydrobromic acid, hydriodic acid, nitric acid, perchloric acid, acetoacetic acid, cyanoacetic acid, tetrahydrofuran-2-carboxylic acid, propiolic acid, methacrylic acid, crotonic acid and picric acid.

The general terms used hereinbefore and hereinafter have the following meanings, unless defined otherwise.

Unless defined otherwise, carbon-containing groups and compounds each contain from 1 up to and including 6, preferably from 1 up to and including 4, especially 1 or 2, carbon atoms.

Halogen, both as a group per se and as a structural element of other groups and compounds, for example haloalkyl, haloalkoxy and haloalkylthio, is fluorine, chlorine, bromine or iodine, especially fluorine, chlorine or bromine, more especially fluorine or chlorine.

Alkyl, both as a group per se and as a structural element of other groups and compounds, for example haloalkyl, alkoxy and alkylthio, is, in each case taking due account of the particular number of carbon atoms contained in the group or compound in question, either straight-chained, i.e. methyl, ethyl, propyl, butyl, pentyl, hexyl, heptyl or octyl, or branched, e.g. isopropyl, isobutyl, sec-butyl, tert-butyl, isopentyl, neopentyl or isohexyl.

Cycloalkyl, both as a group per se and as a structural element of other groups and compounds, for example halocycloalkyl, cycloalkoxy and cycloalkylthio, is, in each case taking due account of the particular number of carbon atoms contained in the group or compound in question, cyclopropyl, cyclobutyl, cyclopentyl, cyclohexyl, cycloheptyl or cyclooctyl.

Alkenyl, both as a group per se and as a structural element of other groups and compounds, is, in each case taking due account of the particular number of carbon atoms and conjugated or isolated double bonds contained in the group in question, either straight-chained, for example vinyl, allyl, 2-butenyl, 3-pentenyl, 1-hexenyl, 1-heptenyl, 1,3-hexadienyl or 1,3-octadienyl, or branched, for example isopropenyl, isobutenyl, isoprenyl, tert-pentenyl, isohexenyl, isoheptenyl or isooctenyl. Preference is given to alkenyl groups containing from 3 to 12, especially from 3 to 6, more especially 3 or 4, carbon atoms.

Alkynyl, both as a group per se and as a structural element of other groups and compounds, is, in each case taking due account of the particular number of carbon atoms and conjugated or isolated double bonds contained in the group or compound in question, either straight-chained, for example ethynyl, propargyl, 2-butynyl, 3-pentynyl, 1-hexynyl, 1-heptynyl, 3-hexen-1-ynyl or 1,5-heptadien-3-ynyl, or branched, for example 3-methylbut-1-ynyl, 4-ethylpent-1-ynyl, 4-methylhex-2-ynyl or 2-methylhept-3-ynyl. Preference is given to alkynyl groups containing from 3 to 12, especially from 3 to 6, more especially 3 or 4, carbon atoms.

Alkylene and alkenylene are straight-chained or branched bridge elements, especially —$CH_2$—$CH_2$—$CH_2$—, —$CH_2$—$CH_2$—$CH_2$—$CH_2$—, —$CH_2$—$CH_2$—$CH_2$—$CH_2$—$CH_2$—, —$CH_2(CH_3)CH_2$—$CH_2$—, —$CH_2C(CH_3)_2$—$CH_2$—, —$CH_2$—$CH$=$CH$—$CH_2$— or —$CH_2$—$CH$=$CH$—$CH_2$—$CH_2$—.

Halo-substituted, carbon-containing groups and compounds, for example halo-substituted alkyl, alkenyl, alkynyl, cycloalkyl, alkoxy and alkylthio, may be partially halogenated or perhalogenated, the halogen substituents in the case of multiple halogenation being identical or different. Examples of haloalkyl, both as a group per se and as a structural element of other groups and compounds, for example haloalkoxy and haloalkylthio, are methyl mono- to tri-substituted by fluorine, chlorine and/or by bromine, for example $CHF_2$ or $CF_3$; ethyl mono- to penta-substituted by fluorine, chlorine and/or by bromine, for example $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl each mono- to hepta-substituted by fluorine, chlorine and/or by bromine, for example $CH_2CHBrCH_2Br$, $CF_2CHFCF_3$, $CH_2CF_2CF_3$ or $CH(CF_3)_2$; butyl, or one of the isomers thereof, mono- to nona-substituted by fluorine, chlorine and/or by bromine, for example $CF(CF_3)CHFCF_3$ or $CH_2(CF_2)_2CF_3$; pentyl, or one of the isomers thereof, mono- to undeca-substituted by fluorine, chlorine and/or by bromine, for example $CF(CF_3)(CHF)_2CF_3$ or $CH_2(CF_2)_3CF_3$; and hexyl, or one of the isomers thereof, mono- to trideca-substituted by fluorine, chlorine and/or by bromine, for example $(CH_2)_4CHBrCH_2Br$, $CF_2(CHF)_4CF_3$, $CH_2(CF_2)_4CF_3$ or $C(CF_3)_2(CHF)_2CF_3$. Aryl is especially phenyl, naphthyl, anthryl or perylenyl, preferably phenyl. Heterocyclyl is especially pyridyl, pyrimidyl, s-triazinyl, 1,2,4-triazinyl, thienyl, furyl, tetrahydrofuranyl, pyranyl, tetrahydropyranyl, pyrrolyl, pyrazolyl, imidazolyl, thiazolyl, triazolyl, oxazolyl, thiadiazolyl, oxadiazolyl, benzothienyl, quinolyl, quinoxalinyl, benzofuranyl, benzimidazolyl, benzopyrrolyl, benzothiazolyl, indolyl, tetrahydro-thiopyranyl, benzopyranyl, N-oxido-pyridinio, fluorenyl, thiomorpholin-yl, morpholinyl, piperidinyl, pyrrolidinyl, piperazinyl, dihydropyranyl, dihydroindolyl, piperazinyl, coumarinyl or indazolyl which are preferably attached by way of a carbon atom; preference is given to thienyl, thiazolyl, benzofuranyl, benzothiazolyl, furyl, oxiranyl, tetrahydropyranyl or indolyl; especially pyridyl or thiazolyl.

In the context of the present invention, preference is given to (2) compounds according to group (1) of formula (I) wherein $R_1$ is isopropyl or sec-butyl, preferably wherein there is present a mixture of the isopropyl and sec-butyl derivatives;

(3) compounds according to group (2) of formula (I) wherein $R_2$ is H;

(4) compounds according to group (2) of formula (I) wherein $R_2$ is $C_1$-$C_8$alkyl, especially methyl;

(5) compounds according to group (2) of formula (I) wherein $R_2$ is ethyl;

(6) compounds according to group (2) of formula (I) wherein $R_2$ is n-propyl;

(7) compounds according to one of groups (1) to (6) of formula (I) wherein $R_3$ is unsubstituted or substituted, especially unsubstituted, $C_1$-$C_{12}$alkyl;

(8) compounds according to one of groups (1) to (7) of formula (I) wherein $R_3$ is methyl;

(9) compounds according to one of groups (1) to (7) of formula (I) wherein $R_3$ is ethyl;

(10) compounds according to one of groups (1) to (7) of formula (I) wherein $R_3$ is n-propyl;

(11) compounds according to one of groups (2) to (7) of formula (I) wherein $R_3$ is isopropyl;

(12) compounds according to one of groups (1) to (7) of formula (I) wherein $R_3$ is n-butyl, sec-butyl, isobutyl or tert-butyl;

(13) compounds according to one of groups (1) to (6) of formula (I) wherein $R_3$ is unsubstituted or substituted, especially unsubstituted, $C_6$-$C_{12}$alkyl;

(14) compounds according to one of groups (1) and (2) of formula (I) wherein $R_2$ and $R_3$ together are —$CH_2$—$CH_2$—$CH_2$— or —$CH_2$—$CH_2$—$CH_2$—$CH_2$—;

(15)) compounds according to one of groups (1) and (2) of formula (I) wherein $R_2$ and $R_3$ together are —$CH_2$—$CH_2$—O—$CH_2$—$CH_2$— or —$CH_2$—$CH_2$—N($CH_3$)—$CH_2$—$CH_2$—;

(16) compounds according to one of groups (1) to (6) of formula (I) wherein $R_3$ is substituted $C_1$-$C_4$alkyl and the substituents are selected from the group consisting of OH, halogen, $C_3$-$C_8$cycloalkyl, $C_3$-$C_8$cycloalkenyl that is unsubstituted or substituted by from one to three methyl groups, $C_1$-$C_{12}$alkoxy, $C_2$-$C_8$alkynyl, —C(=O)$R_5$, —NHC(=O)$R_6$, —P(=O)(O$C_1$-$C_6$alkyl)$_2$, unsubstituted or, depending on the possibilities for substitution on the ring, mono- to penta-substituted phenyl, naphthyl, anthryl, phenanthrenyl, fluorenyl, perylenyl and heterocyclyl;

especially wherein the substituents of $R_3$ are selected from the group consisting of halogen, $C_3$-$C_8$cycloalkyl, $C_2$-$C_8$alkynyl, —C(=O)$R_5$, —NHC(=O)$R_6$, —P(=O)(O$C_1$-$C_6$alkyl)$_2$; phenyl, naphthyl, anthryl, pyridyl, thiazolyl, imidazolyl, furyl, quinolyl, pyrazolyl, which are unsubstituted or, depending on the possibilities for substitution on the ring, are mono- to tri-substituted;

(17) compounds according to one of groups (1) to (6) of formula (I) wherein $R_3$ is benzyl carrying, on the aromatic moiety, from one to three substituents selected from the group consisting of OH, halogen, CN, $NO_2$, $C_1$-$C_2$alkyl, dimethylamino-$C_1$-$C_4$alkoxy, $C_3$-$C_6$cycloalkyl, $C_1$-$C_2$haloalkyl, $C_1$-$C_2$alkoxy, $C_1$-$C_2$haloalkoxy, phenoxy, phenyl-$C_1$-$C_6$alkyl, phenyl-$C_1$-$C_4$alkenyl, unsubstituted or chloro- or methoxy-substituted phenoxy, unsubstituted or chloro-, methoxy- or trifluoromethyl-substituted benzyloxy, methylenedioxy, —C(=O)Z$R_5$, —O—C(=O)$R_6$ and NHC(=O)$R_6$;

$R_5$ is H, OH, $NH_2$, NH($C_1$-$C_2$alkyl), N($C_1$-$C_2$alkyl)$_2$, —O—$C_1$-$C_2$alkyl-C(=O)—$R_7$, NH$C_1$-$C_2$alkyl-C(=O)—$R_7$, $C_1$-$C_6$alkyl, $C_1$-$C_2$alkoxy, $C_1$-$C_2$alkoxy-$C_1$-$C_2$alkoxy, $C_2$-$C_4$alkenyloxy, $C_2$-$C_4$alkynyloxy; phenyl, phenoxy, benzyloxy, NH-phenyl, NH—$C_1$-$C_6$alkyl-C(=O)—$R_7$; or phenyl, phenoxy, benzyloxy or NH-phenyl which are substituted by halogen, nitro, methoxy, trifluoromethyl or trifluoromethoxy;

$R_6$ is H, $C_1$-$C_3$alkyl, phenyl or benzyl;

$R_7$ is H, OH, $NH_2$, NH($C_1$-$C_{12}$alkyl), N($C_1$-$C_{12}$alkyl)$_2$, $C_1$-$C_{12}$alkyl, $C_1$-$C_{12}$alkoxy, $C_1$-$C_6$alkoxy-$C_1$-$C_6$alkoxy, $C_2$-$C_8$alkenyloxy, phenyl, phenoxy, benzyloxy, or NH-phenyl; and Z is a bond, O or NH;

(18) compounds according to one of groups (1) to (6) of formula (I) wherein $R_3$ is $C_1$-$C_4$alkyl-C(=O)$R_5$, especially —$CH_2$—C(=O)$R_5$; and $R_5$ is H, OH, $NH_2$, NH($C_1$-$C_2$alkyl), N($C_1$-$C_2$alkyl)$_2$, $C_1$-$C_4$alkyl, $C_1$-$C_{12}$alkoxy, $C_2$-$C_4$alkenyloxy, phenyl, phenoxy, benzyloxy, NH-phenyl, NH—$C_1$-$C_2$alkyl-C(=O)—O—$C_1$-$C_2$-alkyl-phenyl, —P(=O)(O$C_1$-$C_6$alkyl)$_2$; or phenyl, phenoxy, benzyloxy or NH-phenyl which are substituted by chlorine, fluorine, methoxy, trifluoromethyl or by trifluoromethoxy;

more especially wherein $R_5$ is $C_1$-$C_{12}$alkoxy;

(19) compounds according to one of groups (1) to (6) of formula (I) wherein $R_3$ is $C_2$-$C_6$alkyl-NHC(=O)$R_6$ and $R_6$ is H, $C_1$-$C_4$alkyl, $C_2$-$C_4$alkenyl, $C_2$-$C_4$alkynyl, phenyl or benzyl;

(20) compounds according to one of groups (1) to (6) of formula (I) wherein $R_3$ is —$CH_2$-heterocyclyl and heterocyclyl is pyridyl, furyl, tetrahydrofuranyl, pyranyl, tetrahydropyranyl, pyrazolyl, imidazolyl, thiazolyl, benzothienyl, quinolyl, quinoxalinyl, benzofuranyl, benzimidazolyl, benzopyrrolyl, benzothiazolyl, indolyl, coumarinyl or indazolyl, the mentioned radicals being unsubstituted or substituted by one or two substituents selected independently of one another from halogen, trifluoromethyl, trifluoromethoxy and nitro; preferably pyridyl, furyl, pyrazolyl, imidazolyl, thiazolyl, benzimidazolyl, benzopyrrolyl, benzothiazolyl or indolyl which are unsubstituted or substituted by one or two substituents selected independently of one another from halogen, trifluoromethyl, trifluoromethoxy and nitro; especially pyridyl or thiazolyl which are unsubstituted or substituted by one or two substituents selected independently of one another from halogen, trifluoromethyl, trifluoromethoxy and nitro, more especially monosubstituted by chlorine;

(21) compounds according to one of groups (1) to (6) of formula (I) wherein $R_3$ is $C_2$-$C_{10}$alkenyl, especially $C_2$-$C_4$alkenyl, which is unsubstituted or mono- or di-substituted, especially mono-substituted, by $C_2$-$C_4$alkynyl, —C(=O)—$C_1$-$C_4$alkoxy, —C(=O)—O—$C_1$-$C_4$alkylbenzoyl, phenyl or by halogen; especially wherein $R_3$ is —$CH_2$—CH=$CH_2$;

(22) compounds according to one of groups (1) to (6) of formula (I) wherein $R_3$ is branched, unsubstituted $C_4$-$C_{10}$alkyl;

(23) compounds according to one of groups (1) to (6) of formula (I) wherein $R_3$ is branched, substituted $C_3$-$C_{10}$alkyl;

(24) compounds according to one of groups (1) to (6) of formula (I) wherein $R_3$ is unsubstituted benzyl;

(25) compounds according to one of groups (1) to (6) of formula (I) wherein $R_3$ is unsubstituted or substituted, especially unsubstituted, $C_2$-$C_{12}$alkyl;

(26) in the context of the invention special preference to given to the compounds of formula (I) listed in the Tables and, where appropriate, E/Z isomers and mixtures of E/Z isomers thereof, very especially the compounds 4"-deoxy-4"-(S)—N-methylamino-avermectin B1;
4"-deoxy-4"-(S)—N-dimethylamino-avermectin B1;
4"-deoxy-4"-(S)—N-ethylamino-avermectin B1;
4"-deoxy-4"-(S)—N-prop-1-ylamino-avermectin B1;
4"-deoxy-4"-(S)—(N-ethyl-N-methyl-amino)-avermectin B1;
4"-deoxy-4"-(S)—(N-methyl-N-prop-1-yl-amino)-avermectin B1;
4"-deoxy-4"-(S)—(N-isopropyl-N-methylamino)-avermectin B1;
4"-deoxy-4"-(S)—(N-isopropyl-amino)-avermectin B1;
4"-deoxy-4"-(S)—(N-methyl-N-1-propen-3-yl-amino)-avermectin B1;
4"-deoxy-4"-(S)—(N-methyl-N-ethoxycarbonylmethyl-amino)-avermectin B1;
4"-deoxy-4"-(S)—(N-methyl-N-benzyl-amino)-avermectin B1;
4"-deoxy-4"-(S)—(N-methyl-N-4-difluoromethoxyphenylmethyl-amino)-avermectin B1;
4"-deoxy-4"-(S)—(N-methyl-N-2,5-dichlorophenylmethyl-amino)-avermectin B1;
4"-deoxy-4"-(S)—(N-methyl-N-2,5-difluorophenylmethyl-amino)-avermectin B1;
4"-deoxy-4"-(S)—(N-methyl-N-2,3,4-trifluorophenylmethyl-amino)-avermectin B1;
4"-deoxy-4"-(S)-(pyrrolidin-1-yl)-avermectin B1;
4"-deoxy-4"-(S)-(azetidin-1-yl)-avermectin B1;

4"-deoxy-4"-(S)—(N-methyl-N-[3-{2-oxo-2-phenyl-ethoxycarbonyl}-allyl]-amino)-avermectin B1;

4"-deoxy-4"-(S)—(N-methyl-N-1-propargyl-amino)-avermectin B1; and

4"-deoxy-4"-(S)-(piperidin-1-yl)-avermectin B1.

The invention relates also to a process for the preparation of compounds of formula (I) as defined under (1) hereinbefore and, where appropriate, tautomers thereof, in which process (A) a compound of formula

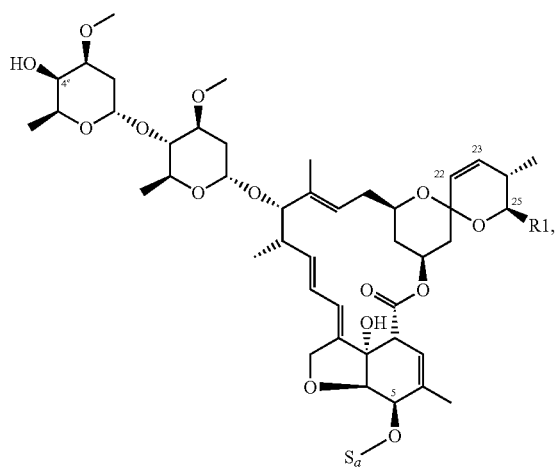

(II)

wherein $R_1$ is as defined hereinbefore under (1) for formula (I) and $S_a$ is a protecting group, and which is known or can be prepared by methods known per se, is reacted with a sulfonic acid derivative to form a compound of formula wherein Q is a sulfonic acid radical and $S_a$ and $R_1$ are as defined for formula (II);

(B) the resulting compound of formula (III) is reacted with an azide salt to form a compound of formula (IV)

wherein the radical $A_v$ corresponds to the macrocycle of the basic avermectin structure as indicated within the brackets of formula (III), with inversion at the 4"-position; or, where appropriate, (C) for the preparation of a compound of formula (IV), a compound of formula (II) is reacted with an azide in the presence of triphenylphosphine or a trialkylphosphine and an azodicarboxylic acid derivative;

(D) the protecting group Sa of the compound of formula (IV) is split off by reaction with an acid to form the compound of formula (III)

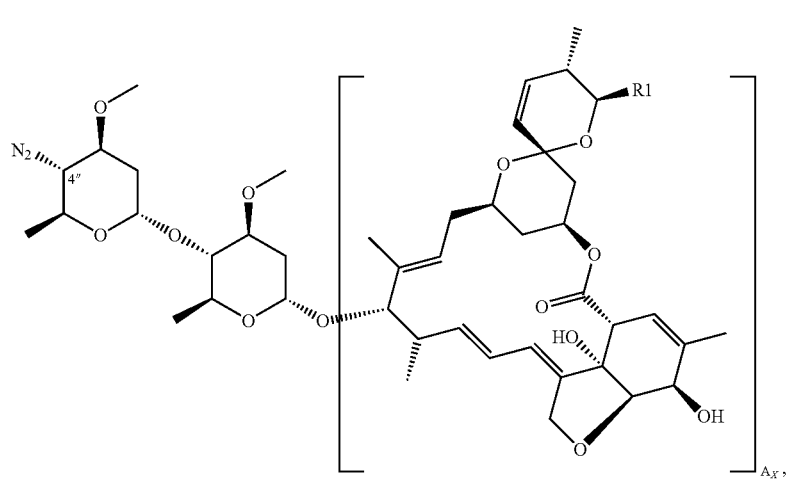

wherein $R_1$ is as defined hereinbefore;

(E) for the preparation of a compound of formula (I) wherein $R_2$ is H and $R_3$ is —CH$_2$—$R_{33}$, with $R_{33}$ being unsubstituted or mono- to penta-substituted $C_1$-$C_{11}$alkyl, unsubstituted or mono- to penta-substituted $C_2$-$C_{11}$alkenyl; or unsubstituted or mono- to penta-substituted $C_2$-$C_{11}$alkynyl; a compound of formula (IV) is reacted first (E1) with a phosphine or a phosphite; then (E2) with an aldehyde of formula $R_{33}$—CHO; and then (E3) with a hydride, optionally in the presence of a catalytic amount of acid, to form a compound of formula (VI)

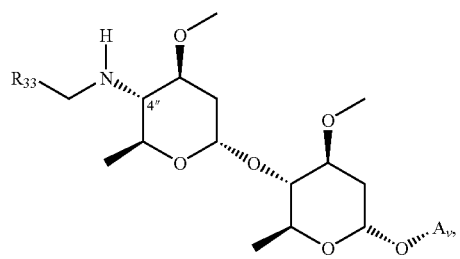

wherein $A_y$ corresponds to the macrocyclic structure defined for formula (IV) and $R_{33}$ is as defined hereinbefore; and (F) the protecting group is split off from the resulting compound of formula (VI) analogously to process step (D); or, (G) for the preparation of a compound of formula (I) wherein $R_2$ and $R_3$ are as defined under process step (E), a compound of formula (V) is reacted analogously to process steps (E1) to (E3);

(H) for the preparation of a compound of formula (I) wherein $R_2$ is H and $R_3$ is —CH$_3$, a compound of formula (IV) is reacted first (H1) with a phosphine; then (H2) with aqueous formaldehyde in the presence a water-withdrawing agent such as a of a molecular sieve, or with formaldehyde generated from paraformaldehyde; and then (H3) with a hydride in the presence of a catalytic amount of acid; and the resulting compound of formula (VIa)

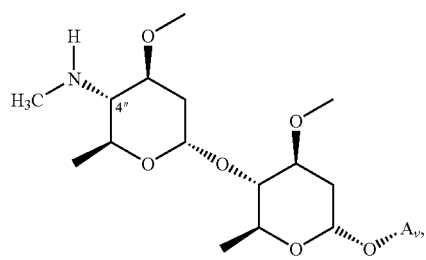

wherein $A_y$ corresponds to the macrocyclic structure defined for formula (IV), is further reacted analogously to process step (D); or, (I) for the preparation of a compound of formula (I) wherein $R_2$ is H and $R_3$ is —CH$_3$, a compound of formula (V) is reacted analogously to process steps (H1) to (H3); or, (K) for the preparation of a compound of formula (I) wherein $R_2$ is CH$_3$ and $R_3$ is as defined hereinbefore for formula (I), a compound of formula (I) wherein $R_3$ is as defined hereinbefore for formula (I) is reacted, in accordance with process steps (H2) and (H3) above, first in the presence of a catalytic amount of acid with formaldehyde or paraformaldehyde, and then with a hydride; or, (L) for the preparation of a compound of formula (I) wherein $R_2$ is H or unsubstituted or mono- to penta-substituted $C_1$-$C_{12}$alkyl or unsubstituted or mono- to penta-substituted $C_2$-$C_{12}$alkenyl, and $R_3$ is as defined hereinbefore for formula (I), a compound of formula (I), wherein $R_2$ is H and $R_3$ is H or is as defined hereinbefore for formula (I), is reacted with a compound of formula Hal-$R_3$, wherein $R_3$ is unsubstituted or mono- to penta-substituted $C_1$-$C_{12}$alkyl or unsubstituted or mono- to penta-substituted $C_2$-$C_{12}$alkenyl and Hal is halogen, preferably iodine; or, (M) for the preparation of a compound of formula (I) wherein $R_2$ and $R_3$ are CH$_3$, a compound of formula (I), wherein $R_2$ and $R_3$ are hydrogen, is reacted (M1) with formaldehyde or paraformaldehyde; and then (M2) with a hydride in the presence of a catalytic amount of acid; or, (N) for the preparation of a compound of formula (I) wherein $R_2$ and $R_3$ together are a three- to seven-membered alkylene or four- to seven-membered alkenylene bridge in each of which a $CH_2$ group may have been replaced by O, S or $NR_4$, a compound of formula (I), wherein $R_2$ and $R_3$ are H, is reacted with a compound of formula Hal-$C_3$-$C_7$alkylene-Hal or a compound Hal-$C_4$-$C_7$alkenylene-Hal, wherein in the alkylene and alkenylene groups a $CH_2$ group may have been replaced by O, S or $NR_4$ and Hal is a halogen.

The invention relates also to (O) a process for the preparation of a compound of formula (I) wherein $R_2$ and $R_3$ are H, in which process either a compound of formula (IV) is reacted, analogously to process step (H1), with a phosphine and then with a base; and the resulting compound, which carries a protecting group in the 5-position, is further reacted analogously to process step (D); or a compound of formula (V) is reacted, analogously to process step (H1), with a phosphine and then with a base.

The remarks made above in relation to tautomers of compounds of formula (I) apply analogously to starting materials referred to hereinbefore and hereinafter as regards the tautomers thereof.

The reactions described hereinbefore and hereinafter are carried out in a manner known per se, for example in the absence or, customarily, in the presence of a suitable solvent or diluent or a mixture thereof, the reactions being carried out, as required, with cooling, at room temperature or with heating, for example in a temperature range of from about –80° C. to the boiling point of the reaction medium, preferably from about 0° C. to about +150° C., and, if necessary, in a closed vessel, under pressure, in an inert gas atmosphere and/or under anhydrous conditions. Especially advantageous reaction conditions can be found in the Examples.

The reaction time is not critical; preference is given to a reaction time of from about 0.1 to about 72 hours, especially from about 0.5 to about 24 hours.

The product is isolated by customary methods, for example by means of filtration, crystallisation, distillation or chromatography, or any suitable combination of such methods.

The starting materials mentioned hereinbefore and hereinafter that are used for the preparation of compounds of formula (I) and, where appropriate, tautomers thereof, are known or can be prepared by methods known per se, for example in accordance with the information given hereinafter.

Process Variant (A):

Examples of suitable solvents and diluents include: aromatic, aliphatic and alicyclic hydrocarbons and halogenated hydrocarbons, such as benzene, toluene, xylene, mesitylene, Tetralin, chlorobenzene, dichlorobenzene, bromobenzene, petroleum ether, hexane, cyclohexane, dichloromethane, trichloromethane, tetrachloromethane, dichloroethane, trichloroethene and tetrachloroethene; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxydiethyl ether, tetrahydrofuran and dioxane; or mixtures of the mentioned solvents. Preference is given to dichloromethane.

Suitable leaving groups Q in the compounds of formula (III) are especially sulfonic acid radicals; preference is given, for example, to the anions of toluenesulfonic acid, methanesulfonic acid, trifluoromethanesulfonic acid, pentafluoroethanesulfonic acid and nonafluorobutanesulfonic acid.

Suitable protecting groups Sa in the compounds of formulae (II), (III), (IV) and (VI) are especially trialkylsilyl- or allyoxycarbonyl-groups; preference is given, for example, to trimethylsilyl, triethylsilyl, dimethyl-tert-butylsilyl, dim-ethyl-isopropylsilyl, dimethyl-1,1,2-trimethylpropylsilyl, diethyl-isopropylsilyl, dimethyl-tert-hexylsilyl; but also to phenyl-tert-alkylsilyl groups such as diphenyl-tert-butylsilyl.

The reactions are advantageously carried out in a temperature range of from about –70° C. to +10° C., preferably from –35° C. to 0° C.

Especially preferred conditions for the reaction are described in Example A.1.

Process Variant (B):

Examples of solvents and diluents include: nitriles, such as acetonitrile; dimethyl sulfoxide; and also alcohols, such as, for example, ethanol or methanol; amides, such as dimethylformamide or dimethylacetamide, are especially suitable.

Especially suitable azide salts are $NaN_3$ and $Zn(N_3)_2 \cdot$pyridine; especially $NaN_3$.

The reactions are advantageously carried out in a temperature range of from –10° C. to +10° C.

Especially preferred conditions for the reaction are described, for example, in Example A.1.

Process Variant (C):

Examples of suitable solvents and diluents are the same as those mentioned in process variant (A). Also suitable are amides, such as dimethylformamide, dimethylacetamide or hexamethylphosphoric triamide.

Suitable azodicarboxylic acid derivatives are especially azodicarboxylic acid esters, for example the dibenzyl, diethyl, dibutyl, diisopropyl or di-tert-butyl ester or the di-(2,2,2-trichloroethyl) ester; or azodicarboxylic acid amides, such as, for example, N,N,N,N-azodicarboxylic acid tetramethylamide or azodicarboxylic acid dimorpholide.

Suitable azide sources are especially $(PhO)_2PN_3$, $Zn(N_3)_2$·pyridine or $HN_3$.

Suitable phosphines are especially trialkyl- and triarylphosphines, such as, for example, trimethyl-, triethyl- and tri-n-butyl-phosphine and also triphenylphosphine.

The reactions are advantageously carried out in a temperature range of from –20° C. to 150° C.

Process Variant (D):

Examples of suitable solvents and diluents are the same as those mentioned in process variant (A). Also suitable are nitriles, such as acetonitrile; dimethyl sulfoxide; and alcohols, such as, for example, ethanol or methanol; and also water.

The reactions are advantageously carried out in a temperature range of from –10° C. to 25° C.

Suitable acids for splitting off the protecting group are, for example, HF in pyridine, $Zn(BF_4)_2 \cdot H_2O$ or methanesulfonic acid.

Especially preferred conditions for this process variant are described, for example, in Example A.2.

Process Variant (E):

Examples of suitable solvents and diluents are the same as those mentioned in process variant (A). Also suitable are nitrites, such as acetonitrile; and also esters of carboxylic acids, such as, for example ethyl acetate.

The reactions are advantageously carried out in a temperature range of from 0° C. to +100° C.

Suitable phosphines include, inter alia, the same as those mentioned under process variant (C). Suitable phosphites are, for example, trimethyl phosphite, triethyl phosphite, tri-n-butyl phosphite and tri-tert-butyl phosphite.

Suitable hydrides are, especially, complex hydrides, especially sodium borohydride and sodium cyanoborohydride.

Suitable acids are, especially, weak carboxylic acids, such as acetic acid, propionic acid or pivalic acid, especially pivalic acid. The acids are used preferably in catalytic amounts, especially in amounts of less than 10 mol %, more especially less than 5 mol %, very especially less than 2 mol %.

Especially preferred conditions for this process variant are described, for example, in Example A.3.

Process Variant (F):

The same process conditions apply as described in variant (D). The reaction is preferably carried out in the presence of methanesulfonic acid in methanol at 0° C.

Process Variant (G):

The same process conditions apply as described in variant (E).

Process Variant (H):

The same process conditions apply as described in variant (E). As phosphine there are used, for example, trimethylphosphine or tributylphosphine, preferably trimethylphosphine.

In variant (H2), the generation of formaldehyde from paraformaldehyde is carried by heating a suspension of paraformaldehyde in a solvent such as an ether in the presence of a catalytical amount of an acid such as para-toluoenesulfonic acid. The formaldehyde is being distilled off the solution.

Process Variant (I):

The same process conditions apply as described in variant (H).

Process Variant (K):

Preferred solvents are alcohols, such as methanol or ethanol.

The reactions are advantageously carried out in a temperature range of from 0° C. to +20° C.; preferably from 0° C. to 10° C.

Otherwise the same conditions apply as mentioned in process variant (H). Special preference is given to proceeding with sodium borohydride or sodium cyanoborohydride and with pivalic acid as catalyst.

Process Variant (L):

The same solvents are used as mentioned in process variant (A). Also suitable are amides, such as dimethylformamide and dimethylacetamide; nitrites, such as acetonitrile; and esters, such as ethyl acetate.

Suitable bases are especially carbonates, such as sodium carbonate, sodium hydrogen carbonate and potassium carbonate, trialkylamines, such as triethylamine, and heterocyclic bases, such as, for example, pyridine.

Process Variant (M):

Suitable solvents are especially alcohols, such as methanol or ethanol.

Formaldehyde is preferably used either in the form of an aqueous solution or in the form of paraformaldehyde. Preference is given to a mode of operation in which an excess of formaldehyde or paraformaldehyde is used.

Special preference is given to proceeding with sodium borohydride or sodium cyanoborohydride and with pivalic acid or acetic acid as catalyst.

Process Variant (N):

Examples of suitable solvents and diluents are the same as those mentioned in process variant (A). Also suitable are esters of carboxylic acids, such as, for example, ethyl acetate.

Suitable bases are especially carbonates, such as sodium carbonate, sodium hydrogen carbonate or potassium carbonate.

Process Variant (O):

Examples of suitable solvents and diluents are the same as those mentioned in process variant (A). Also suitable are nitrites, such as acetonitrile; and also esters of carboxylic acids, such as, for example, ethyl acetate.

Suitable phosphines are especially trialkyl- and triarylphosphines, such as, for example, trimethyl- and tri-n-butyl phosphine and also triphenylphosphine.

As bases there are especially used sodium hydroxide solution or ammonium hydroxide, especially in highly diluted form, more especially in a concentration of, for example, 0.01N.

The compounds of formula (I) may be in the form of one of the possible isomers or in the form of a mixture thereof, in the form of pure isomers, or in the form of mixtures of isomers, that is to say in the form of a racemic mixture; the invention relates both to the pure isomers and to the racemic mixtures and this is to be understood accordingly hereinbefore and hereinafter, even when stereochemical details are not specifically mentioned in each case.

The racemates can be resolved into the optical antipodes by known methods, for example by recrystallisation from an optically active solvent, by chromatography on chiral adsorbents, for example high-pressure liquid chromatography (HPLC) on acetyl cellulose, with the aid of suitable microorganisms, by cleavage with specific immobilised enzymes, or via the formation of inclusion compounds, for example using chiral crown ethers, in which case only one enantiomer is complexed.

According to the invention, pure optical isomers can be obtained not only by separation of corresponding mixtures of isomers but also by generally known methods of enantioselective synthesis, for example by carrying out the process according to the invention with starting materials that have appropriate stereochemistry.

It is advantageous to isolate or synthesise whichever isomer is biologically more active, insofar as the individual components have different biological activity.

The compounds of formula (I) may also be obtained in the form of their hydrates and/or may include other solvents, for example solvents which may optionally have been used for the crystallisation of compounds in solid form.

The invention relates to all those embodiments of the process according to which a compound obtainable as starting material or intermediate at any stage of the process is used as starting material and all or some of the remaining steps are carried out, or in which a starting material is used in the form of a derivative and/or a salt and/or its racemates or antipodes, or, especially, is formed under the reaction conditions.

In the process of the present invention it is preferable to use those starting materials and intermediates which result in the compounds of formula (I) that are especially preferred.

The invention relates especially to the preparation processes described in the Examples.

The invention relates also to the compounds of formulae (IV), (V) and (VI), and, where appropriate, E/Z isomers, mixtures of E/Z isomers and/or tautomers, in each case in free form or in salt form.

In the area of pest control, the compounds of formula (I) according to the invention are active ingredients exhibiting valuable preventive and/or curative activity with a very advantageous biocidal spectrum and a very wide spectrum, even at low rates of concentration, while being well tolerated by warm-blooded organisms, fish and plants. The compounds are, surprisingly, equally suitable for controlling plant pests and also ecto- and endo-parasites of humans and especially of productive livestock, domestic animals and pets. They are effective against all or individual development stages of normally sensitive animal pests, but also of resistant animal pests, such as insects and representatives of the order Acarina, nematodes, cestodes and trematodes, whilst at the same time sparing useful organisms. The insecticidal or acaricidal activity of the active ingredients according to the invention may manifest itself directly, i.e. in the mortality of the pests, which occurs immediately or only after some time, for example during moulting, or indirectly, for example in reduced oviposition and/or hatching rate, good activity corresponding to a mortality of at least 50 to 60%.

The action of the compounds according to the invention and of compositions comprising them against animal pests can be significantly broadened and adapted to prevailing circumstances by the addition of other insecticides, acaricides or nematicides. Examples of suitable additives include representatives of the following classes of active ingredients: organophosphorus compounds, nitrophenols and derivatives, formamidines, ureas, carbamates, pyrethroids, chlorinated hydrocarbons, neonicotinoids and *Bacillus thuringiensis* preparations.

Especially suitable mixing partners are, for example: azamethiphos; chlorfenvinphos; cypermethrin, cypermethrin high-cis; cyromazine; diafenthiuron; diazinon; dichlorvos; dicrotophos; dicyclanil; fenoxycarb; fluazuron; furathiocarb; isazofos; jodfenphos; kinoprene; lufenuron; methacriphos; methidathion; monocrotophos; phosphamidon; profenofos; diofenolan; a compound obtainable from the *Bacillus thuringiensis* strain GC91 or from the strain NCTC11821; pymetrozine; bromopropylate; methoprene; disulfoton; quinalphos; taufluvalinate; thiocyclam; thiometon; aldicarb; azinphos-methyl; benfuracarb; bifenthrin; buprofezin; carbofuran; dibutylaminothio; cartap; chlorfluazuron; chlorpyrifos; cyfluthrin; lambda-cyhalothrin; alpha-cypermethrin; zeta-cypermethrin; deltamethrin; diflubenzuron; endosulfan; ethiofencarb; fenitrothion; fenobucarb; fenvalerate; formothion; methiocarb; heptenophos; imidacloprid; isoprocarb; methamidophos; methomyl; mevinphos; parathion; parathion-methyl; phosalone; pirimicarb; propoxur; teflubenzuron; terbufos; triazamate; fenobucarb; tebufenozide; fipronil; beta-cyfluthrin; silafluofen; fenpyroximate; pyridaben; fenazaquin; pyriproxyfen; pyrimidifen; nitenpyram; acetamiprid; avermectin B1 (abamectin); emamectin; emamectin benzoate; spinosad; a plant extract which is active against insects; a preparation comprising nematodes which is active against insects; a preparation obtainable from *Bacillus subtilis*; a preparation comprising fungi which is active against insects; a preparation comprising viruses which is active against insects; chlorfenapyr; acephate; acrinathrin; alanycarb; alphamethrin; amitraz; Az 60541; azinphos A; azinphos M; azocyclotin; bendiocarb; bensultap; beta-cyfluthrin; BPMC; brofenprox; bromophos A; bufencarb; butocarboxim; butylpyridaben; cadusafos; carbaryl; carbophenothion; chloethocarb; chlorethoxyfos; chlormephos; cis-resmethrin; clocythrin; clofentezine; cyanophos; cycloprothrin; cyhexatin; demeton M; demeton S; demeton-S-methyl; dichlofenthion; dicliphos; diethion; dimethoate; dimethylvinphos; dioxathion; edifenphos; esfenvalerate; ethion; ethofenprox; ethoprophos; etrimphos; fenamiphos; fenbutatin oxide; fenothiocarb; fenpropathrin; fenpyrad; fenthion; fluazinam; flucycloxuron; flucythrinate; flufenoxuron; flufenprox; fonophos; fosthiazate; fubfenprox; HCH; hexaflumuron; hexythiazox; IKI-220; iprobenfos; isofenphos; isoxathion; ivermectin; malathion; mecarbam; mesulfenphos; metaldehyde; metolcarb; milbemectin; moxidectin; naled; Nc 184; omethoate; oxamyl; oxydemeton M; oxydeprofos; permethrin; phenthoate; phorate; phosmet; phoxim; pirimiphos M; pirimiphos E; promecarb; propaphos; prothiofos; prothoate; pyrachlophos; pyridaphenthion; pyresmethrin; pyrethrum; tebufenozide; salithion; sebufos; sulfotep; sulprofos; tebufenpyrad; tebupirimphos; tefluthrin; temephos; terbam; tetrachlorvinphos; thiacloprid; thiafenox; thiodicarb; thiofanox; thionazin; thuringiensin; tralomethrin; triarthene; triazophos; triazuron; trichlorfon; triflumuron; trimethacarb; vamidothion; xylylcarb; YI 5301/5302; zetamethrin; DPX-MP062-indoxacarb; methoxyfenozide; bifenazate; XMC (3,5-xylyl methylcarbamate); or the fungus pathogen *Metarhizium* Anisopliae; very especially fipronil, thiamethoxam, or lambda-cyhalothrin.

Examples of the abovementioned animal pests which can be controlled with the instantly claimed compounds are:

from the order *Lepidoptera*, for example,

*Acleris* spp., *Adoxophyes* spp., *Aegeria* spp., *Agrotis* spp., *Alabama argillaceae*, *Amylois* spp., *Anticarsia gemmatalis*, *Archips* spp., *Argyrotaenia* spp., *Autographa* spp., *Busseola fusca*, *Cadra cautella*, *Carposina nipponensis*, *Chilo* spp., *Choristoneura* spp., *Clysia ambi*-guella, *Cnaphalocrocis* spp., *Cnephasia* spp., *Cochylis* spp., *Coleophora* spp., *Crocidolomia binotalis*, *Cryptophlebia leucotreta*, *Cydia* spp., *Diatraea* spp., *Diparopsis castanea*, *Earias* spp., *Ephestia* spp., *Eucosma* spp., *Eupoecilia ambiguella*, *Euproctis* spp., *Euxoa* spp., *Grapholita* spp., *Hedya nubiferana*, *Heliothis* spp., *Hellula undalis*, *Hyphantria cunea*, *Keiferia lycopersicella*, *Leucoptera scitella*, *Lithocollethis* spp., *Lobesia botrana*, *Lymantria* spp., *Lyonetia* spp., *Malacosoma* spp., *Mamestra brassicae*, *Manduca sexta*, *Operophtera* spp., *Ostrinia nubilalis*, *Pammene* spp., *Pandemis* spp., *Panolis flammea*, *Pectinophora gossypiella*, *Phthorimaea operculella*, *Pieris rapae*, *Pieris* spp., *Plutella xylostella*, *Prays* spp., *Scirpophaga* spp., *Sesamia* spp., *Sparganothis* spp., *Spodoptera* spp., *Synanthedon* spp., *Thaumetopoea* spp., *Tortrix* spp., *Trichoplusia ni* and *Yponomeuta* spp.;

from the order Coleoptera, for example,

*Agriotes* spp., *Anthonomus* spp., *Atomaria linearis*, *Chaetocnema tibialis*, *Cosmopolites* spp., *Curculio* spp., *Dermestes* spp., *Diabrotica* spp., *Epilachna* spp., *Eremnus* spp., *Leptinotarsa decemlineata*, *Lissorhoptrus* spp., *Melolontha* spp., *Orycaephilus* spp., *Otiorhynchus* spp., *Phlyctinus* spp., *Popillia* spp., *Psylliodes* spp., *Rhizopertha* spp., Scarabeidae, *Sitophilus* spp., *Sitotroga* spp., *Tenebrio* spp., *Tribolium* spp. and *Trogoderma* spp.;

from the order Orthoptera, for example,

*Blatta* spp., *Blattella* spp., *Gryllotalpa* spp., *Leucophaea maderae*, *Locusta* spp., *Periplaneta* spp. and *Schistocerca* spp.;

from the order *Isoptera*, for example, *Reticulitermes* spp.;

from the order Psocoptera, for example, *Liposcelis* spp.;

from the order Anoplura, for example, *Haematopinus* spp., *Linognathus* spp., *Pediculus* spp., *Pemphigus* spp. and *Phylloxera* spp.;

from the order *Mallophaga*, for example, *Damalinea* spp. and *Trichodectes* spp.;

from the order Thysanoptera, for example, *Frankliniella* spp., *Hercinothrips* spp., *Taeniothrips* spp., *Thrips palmi*, *Thrips tabaci* and *Scirtothrips aurantii*;

from the order Heteroptera, for example, *Cimex* spp., *Distantiella theobroma*, *Dysdercus* spp., *Euchistus* spp. *Eurygaster* spp. *Leptocorisa* spp., *Nezara* spp., *Piesma* spp., *Rhodnius* spp., *Sahlbergella singularis*, *Scotinophara* spp. and *Triatoma* spp.;

from the order Homoptera, for example, *Aleurothrixus floccosus*, *Aleyrodes brassicae*, *Aonidiella* spp., *Aphididae*, *Aphis* spp., *Aspidiotus* spp., *Bemisia tabaci, Ceroplaster* spp., *Chrysomphalus aonidium, Chrysomphalus dictyospermi, Coccus hesperidum, Empoasca* spp., *Eriosoma larigerum, Erythroneura* spp., *Gascardia* spp., *Laodelphax* spp., *Lecanium corni, Lepidosaphes* spp., *Macrosiphus* spp., *Myzus* spp., *Nephotettix* spp., *Nilaparvata* spp., *Paratoria* spp., *Pemphigus* spp., *Planococcus* spp., *Pseudaulacaspis* spp., *Pseudococcus* spp., *Psylla* spp., *Pulvinaria aethiopica, Quadraspidiotus* spp., *Rhopalosiphum* spp., *Saissetia* spp., *Scaphoideus* spp., *Schizaphis* spp., *Sitobion* spp., *Trialeurodes vaporariorum, Trioza erytreae* and *Unaspis citri*;

from the order *Hymenoptera*, for example, Acromyrmex, *Atta* spp., *Cephus* spp., *Diprion* spp., *Diprionidae, Gilpinia polytoma, Hoplocampa* spp., *Lasius* spp., *Monomorium pharaonis, Neodiprion* spp., *Solenopsis* spp. and *Vespa* spp.;

from the order Diptera, for example, *Aedes* spp., *Antherigona soccata, Bibio hortulanus, Calliphora erythrocephala, Ceratitis* spp., *Chrysomyia* spp., *Culex* spp., *Cuterebra* spp., *Dacus* spp., *Drosophila melanogaster, Fannia* spp., *Gastrophilus* spp., *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit, Pegomyia hyoscyami, Phorbia* spp., *Rhagoletis pomonella, Sciara* spp., *Stomoxys* spp., *Tabanus* spp., *Tannia* spp. and *Tipula* spp.;

from the order *Siphonaptera*, for example, *Ctenocephalides felis, Ctenocephalides canis, Ceratophyllus* spp. and *Xenopsylla cheopis*;

from the order *Thysanura*, for example, *Lepisma saccharina* and from the order Acarina, for example, *Acarus siro, Aceria sheldoni, Aculus schlechtendali, Amblyomma* spp., *Argas* spp., *Boophilus* spp., *Brevipalpus* spp., *Bryobia praetiosa, Calipitrimerus* spp., *Chorioptes* spp., *Dermanyssus gallinae, Eotetranychus carpini, Eriophyes* spp., *Hyalomma* spp., *Ixodes* spp., *Olygonychus pratensis, Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Tarsonemus* spp. and *Tetranychus* spp.;

from the class Trematoda especially representatives of the family Fasciolidae, especially *Fasciola hepatica*;

from the class Nematoda, for example, root knot nematodes, cyst-forming nematodes and also stem and leaf nematodes;

especially of *Heterodera* spp., e.g. *Heterodera schachtii, Heterodera avenae* and *Heterodera trifolii; Globodera* spp., e.g. *Globodera rostochiensis; Meloidogyne* spp., e.g. *Meloidogyne incognita* and *Meloidogyne javanica; Radopholus* spp., e.g. *Radopholus similis; Pratylenchus*, e.g. *Pratylenchus neglectans* and *Pratylenchus penetrans; Tylenchulus*, e.g. *Tylenchulus semipenetrans*; Longidorus, Trichodorus, Xiphinema, Ditylenchus, Aphelenchoides and Anguina; especially *Meloidogyne*, e.g. *Meloidogyne incognita*, and *Heterodera*, e.g. *Heterodera glycines*.

An especially important aspect of the present invention is the use of the compounds of formula (I) according to the invention for the protection of plants against parasitic feeding pests.

The active ingredients according to the invention can be used to control, i.e. to inhibit or destroy, pests of the mentioned type occurring especially on plants, more especially on useful plants and ornamentals in agriculture, in horticulture and in forestry, or on parts of such plants, such as the fruits, blossoms, leaves, stems, tubers or roots, while in some cases parts of plants that grow later are still protected against those pests.

Target crops are especially cereals, e.g. wheat, barley, rye, oats, rice, maize and sorghum; beet, such as sugar beet and fodder beet; fruit, e.g. pomes, stone fruit and soft fruit, such as apples, pears, plums, peaches, almonds, cherries and berries, e.g. strawberries, raspberries and blackberries; leguminous plants, such as beans, lentils, peas and soybeans; oil plants, such as rape, mustard, poppy, olives, sunflowers, coconut, castor oil, cocoa and groundnuts; cucurbitaceae, such as marrows, cucumbers and melons; fibre plants, such as cotton, flax, hemp and jute; citrus fruits, such as oranges, lemons, grapefruit and mandarins; vegetables, such as spinach, lettuce, asparagus, cabbages, carrots, onions, tomatoes, potatoes and paprika; lauraceae, such as avocado, cinnamon and camphor; and tobacco, nuts, coffee, aubergines, sugar cane, tea, pepper, vines, hops, bananas, natural rubber plants and ornamentals.

Further areas of use of the active ingredients according to the invention are the protection of stored goods and storerooms and the protection of raw materials, and also in the hygiene sector, especially the protection of domestic animals and productive livestock against pests of the mentioned type, especially against infestation of domestic animals, especially cats and dogs, by fleas, ticks and nematodes.

The invention therefore also relates to a pesticidal composition which comprises a compound of the formula (I), in the form of emulsifiable concentrates, suspension concentrates, directly sprayable or dilutable solutions, spreadable pastes, dilute emulsions, wettable powders, soluble powders, dispersible powders, wettable powders, dusts, granules or encapsulations in polymeric substances, all of which comprise—at least—one of the active ingredients according to the invention and which are to be selected to suit the intended aims and prevailing circumstances.

In these compositions, the active ingredient is employed together with—at least—one of the auxiliaries conventionally used in the art of formulation, such as extenders, e.g. solvents or solid carriers, or such as surface-active compounds (surfactants).

Examples of suitable solvents are: non-hydrogenated or partially hydrogenated aromatic hydrocarbons, preferably the fractions $C_8$ to $C_{12}$ of alkylbenzenes, such as xylene mixtures, alkylated naphthalenes or tetrahydronaphthalene, aliphatic or cycloaliphatic hydrocarbons such as paraffins or cyclohexane, alcohols such as ethanol, propanol or butanol, glycols and their ethers and esters such as propylene glycol, dipropylene glycol ether, ethylene glycol, ethylene glycol monomethyl ether or ethylene glycol monoethyl ether, ketones such as cyclohexanone, isophorone or diacetone alcohol, strongly polar solvents such as N-methylpyrrolid-2-one, dimethyl sulfoxide or N,N-dimethylformamide, water, free or epoxidized rapeseed, castor, coconut or soya oil, and silicone oils.

Solid carriers which are used for example for dusts and dispersible powders are, as a rule, ground natural minerals, such as calcite, talc, kaolin, montmorillonite or attapulgite. To improve the physical properties, it is also possible to add highly-disperse silicas or highly-disperse absorptive polymers. Suitable particulate adsorptive carriers for granules are porous types, such as pumice, brick grit, sepiolite or bentonite, and suitable non-sorptive carrier materials are calcite or sand. Moreover, a large number of granulated materials of inorganic or organic nature can be used, in particular dolomite or comminuted plant residues.

Suitable surface-active compounds are, depending on the nature of the active ingredient to be formulated, non-ionic, cationic and/or anionic surfactants or surfactant mixtures which have good emulsifying, dispersing and wetting properties. The surfactants listed below are only to be considered as examples; many more surfactants conventionally used in the art of formulation and suitable in accordance with the invention are described in the relevant literature.

Suitable non-ionic surfactants are primarily polyglycol ether derivatives of aliphatic or cycloaliphatic alcohols, of saturated or unsaturated fatty acids and alkylphenols which can contain 3 to 30 glycol ether groups and 8 to 20 carbon atoms in the (aliphatic) hydrocarbon radical and 6 to 18 carbon atoms in the alkyl radical of the alkylphenols. Also suitable are water-soluble polyethylene oxide adducts with polypropylene glycol, ethylenediaminopolypropylene glycol and alkylpolypropylene glycol having 1 to 10 carbons in the alkyl chain and 20 to 250 ethylene glycol ether and 10 to 100 propylene glycol ether groups. The abovementioned compounds normally contain 1 to 5 ethylene glycol units per propylene glycol unit. Examples which may be mentioned are nonylphenylpolyethoxyethanols, castor oil polyglycol ethers, polypropylene/polyethylene oxide adducts, tributylphenoxypolyethoxyethanol, polyethylene glycol and octylphenoxypolyethoxyethanol. Also suitable are fatty acid esters of polyoxyethylene sorbitan, such as polyoxyethylene sorbitan trioleate.

The cationic surfactants are mainly quaternary ammonium salts which have, as substituents, at least one alkyl radical of 8 to 22 carbon atoms and, as further substituents, lower alkyl, benzyl or lower hydroxyalkyl radicals which may be halogenated. The salts are preferably in the form of halides, methylsulfates or ethylsulfates. Examples are stearyltrimethylammonium chloride and benzyldi(2-chloroethyl) ethylammonium bromide.

Suitable anionic surfactants can be both water-soluble soaps and water-soluble synthetic surface-active compounds. Soaps which are suitable are the alkali metal salts, alkaline earth metal salts and unsubstituted or substituted ammonium salts of higher fatty acids ($C_{10}$-$C_{22}$), such as the sodium or potassium salts of oleic or stearic acid, or of natural fatty acid mixtures which can be obtained, for example, from coconut or tall oil; mention must also be made of the fatty acid methyltaurinates. However, synthetic surfactants, in particular fatty sulfonates, fatty sulfates, sulfonated benzimidazole derivatives or alkylarylsulfonates, are used more frequently. As a rule, the fatty sulfonates and fatty sulfates exist as alkali metal salts, alkaline earth metal salts or unsubstituted or substituted ammonium salts and generally have an alkyl radical of 8 to 22 C atoms, alkyl also including the alkyl moiety of acyl radicals; examples which may be mentioned are the sodium or calcium salt of lignosulfonic acid, of the dodecylsulfuric ester or of a fatty alcohol sulfate mixture prepared with natural fatty acids. This group also includes the salts of the sulfuric esters and sulfonic acids of fatty alcohollethylene oxide adducts. The sulfonated benzimidazole derivatives preferably contain 2 sulfo groups and one fatty acid radical having approximately 8 to 22 C atoms. Examples of alkylarylsulfonates are the sodium, calcium or triethanolammonium salts of dodecylbenzenesulfonic acid, of dibutylnaphthalenesulfonic acid or of a naphthalenesulfonic acid/formaldehyde condensate. Also suitable are corresponding phosphates, such as salts of the phosphoric ester of a p-nonylphenol (4-14) ethylene oxide adduct, or phospholipids.

As a rule, the compositions comprise 0.01 to 99,99%, in particular 0.1 to 99%, in particular 0.1 to 95%, of active ingredient and 0.01 to 99.99%, especially 1 to 99.9%, in particular 5 to 99.9%, of—at least—one solid or liquid auxiliary, it being possible, as a rule, for the surfactants to amount to 0 to 25%, in particular 0.1 to 20%, of the composition (% is in each case percent by weight). While concentrated compositions are more preferred as commercially available goods, the end user uses, as a rule, dilute compositions, which have a considerably lower concentration of active ingredient. Preferred compositions are composed in particular as follows (%=percent by weight):

| | |
|---|---|
| Emulsifiable concentrates: | |
| active ingredient: | 1 to 90%, preferably 5 to 20% |
| surfactant: | 1 to 30%, preferably 10 to 20% |
| solvent: | 5 to 98%, preferably 70 to 85% |
| Dusts: | |
| active ingredient: | 0.1 to 10%, preferably 0.1 to 1% |
| solid carrier: | 99.9 to 90%, preferably 99.9 to 99% |
| Suspension concentrates: | |
| active ingredient: | 5 to 75%, preferably 10 to 50% |
| water: | 94 to 24%, preferably 88 to 30% |
| surfactant: | 1 to 40%, preferably 2 to 30% |
| Wettable powder: | |
| active ingredient: | 0.5 to 90%, preferably 1 to 80% |
| surfactant: | 0.5 to 20%, preferably 1 to 15% |
| solid carrier: | 5 to 99%, preferably 15 to 98% |
| Granules: | |
| active ingredient: | 0.5 to 30%, preferably 3 to 15% |
| solid carrier: | 99.5 to 70%, preferably 97 to 85% |

The activity of the compositions according to the invention can be widened considerably, and adapted to prevailing circumstances, by adding other insecticidally, acaricidally and/or fungicidally active ingredients. Examples of suitable additives of active ingredients are representatives of the following classes of active ingredients: organophosphorus compounds, nitrophenols and derivatives, formamidines, ureas, carbamates, pyrethroids, chlorinated hydrocarbons and *Bacillus thuringiensis* preparations. The compositions according to the invention may also comprise other solid or liquid auxiliaries such as stabilizers, for example epoxidized or unepoxidized vegetable oils (e.g. epoxidized coconut oil, rapeseed oil or soya oil), antifoams, e.g. silicone oil, preservatives, viscosity regulators, binders and/or tackifiers, and also fertilizers or other active ingredients for achieving specific effects, for example bactericides, nematicides, molluscicides or selective herbicides.

The compositions according to the invention are prepared in a known manner, in the absence of auxiliaries for example by grinding and/or screening a solid active ingredient, or active ingredient mixture, for example to obtain a specific particle size, and in the presence of at least one auxiliary for example by intimately mixing and/or grinding the active ingredient, or active ingredient mixture, with the auxiliary (or auxiliaries). These processes for the preparation of the compositions according to the invention and the use of the compounds of the formula (I) for the preparation of these compositions are also subjects of the invention.

The methods of application for the compositions, i.e. the methods of controlling pests of the abovementioned type, such as spraying, atomizing, dusting, brushing on, seed-dressing, scattering or pouring, which are to be selected to suit the intended aims and the prevailing circumstances, and the use of the compositions for controlling pests of the abovementioned type are also subjects of the invention. Typical use concentrations are between 0.1 and 1000 ppm, preferably between 0.1 and 500 ppm, of active ingredient. The rates of application per hectare are generally 1 to 2000 g of active ingredient per hectare, in particular 10 to 1000 g/ha, preferably 20 to 600 g/ha, especially 20 to 100 g/ha.

A preferred method of application in the field of crop protection is application to the foliage of the plant (foliar application), it being possible to adjust frequency and rate of application to the degree or risk of infestation with the pest in question. Alternatively, the active ingredient can reach the plants via the root system (systemic action), by drenching the locus of the plants with a liquid composition or by incorporating the active ingredient in solid form into the locus of the plants, for example in the soil, for example in the form of granules (soil application). In the case of paddy rice crops, such granules can be metered into the flooded paddy field.

The compositions according to the invention are also suitable for the protection of plant propagation material, e.g. seed such as fruits, tubers or kernels, or nursery plants, against fungal infection and animal pests. The propagation material can be dressed with the composition before planting, for example seed can be dressed before sowing. It is also possible to apply the active ingredients according to the invention to seed kernels (coating), either by soaking the kernels in a liquid composition or by coating them with a solid composition. Alternatively, the composition can be applied to the site of application when the propagation material is planted, for example into the seed furrow during sowing. These treatment methods for plant propagation material and the plant propagation material treated accordingly are further subjects of the invention.

PREPARATION EXAMPLES

In the following Examples, the preparation of avermectin B1 derivatives (mixtures of avermectin B1a and B1b derivatives) is described. The B1b derivative generally is present in the mixtures only in an amount of about from 5 to 10% by weight, for which reason only the bands of the B1a derivative can usually be seen in the NMR spectrum.

The abbreviations in the details of NMR data denote:
s: singlet, MHz: megahertz, brs: broad singlet; t: triplet; m: multiplet; d: doublet; J: coupling constant.

TBDMS in the Examples denotes the radical —Si(CH$_3$)$_2$ (tert-butyl), R$_1$ denotes a mixture of isopropyl and sec-butyl.

Example A.1

Preparation of 4"-deoxy-4"-(S)-azido-5-OTBDMS-avermectin B1 of Formula

Synthesis Variant a):

To a solution of 10.93 g of 4"-(R)-5-OTBDMS-avermectin B1 (mixture of B1a and B1b derivative) in 180 ml of absolute tetrahydrofuran under argon there are added 11.61 g of triphenylphosphine and the mixture is cooled to 0° C. 13.21 g of dibenzyl azodicarboxylate and 12.19 g of diphenylphosphoryl azide in 120 ml of absolute tetrahydrofuran are added, dropwise, to the reaction solution over the course of 30 minutes, with stirring. The mixture is allowed to warm up to room temperature and is then heated at 50° C. for 5 hours. The mixture is left to stand overnight at room temperature and is then poured onto ice-water and extracted three times with ether. Washing twice with saturated aqueous NaCl solution and drying over Na$_2$SO$_4$ and concentration by evaporation yields the crude product in the form of a viscous oil. Column chromatography on silica gel using ethyl acetate/hexane (1:10 to 1:4) as eluant, dissolving in CH$_2$Cl$_2$ and subsequent evaporation of the solvent and drying under a high vacuum yields the desired product in the form of a colourless dry foam.

Synthesis Variant b):

Step 1): To 987 mg of 4"-(R)-5-OTBDMS-avermectin B1 in 30 ml of absolute CH$_2$Cl$_2$ under argon there are added, in rapid succession, at −35° C., 732 mg of 4-N,N-dimethylaminopyridine, 775 mg of ethyldiisopropylamine (Hünig's base) and 1129 mg of trifluoromethanesulphonic anhydride, with vigorous stirring, and stirring is continued at 0° C. for 2 h. After 70 minutes, a further portion of 0.2 ml of trifluoromethanesulphonic anhydride is added. The mixture is then poured onto ice-water, extracted twice with ether, washed several times each with water and with saturated aqueous NaCl solution and dried with Na$_2$SO$_4$, and the solvent is evaporated off. Fractionated filtration over silica gel on a column using ethyl acetate/hexane (1:2) as eluant yields the compound of formula

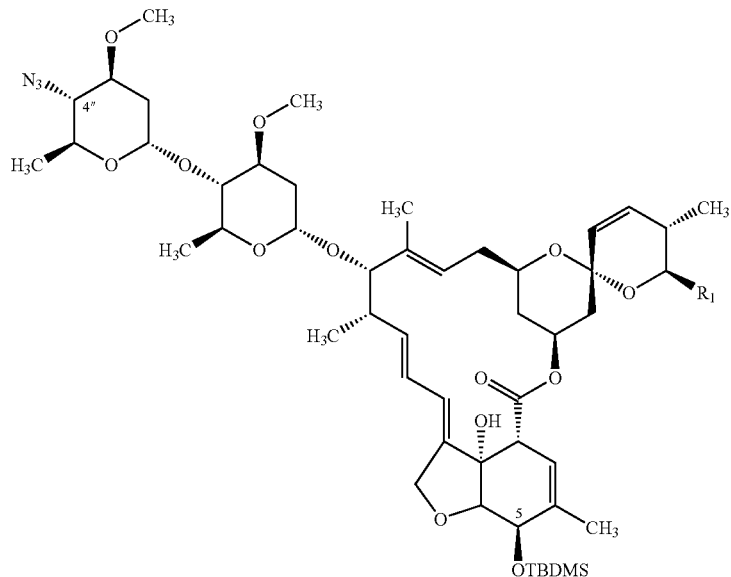

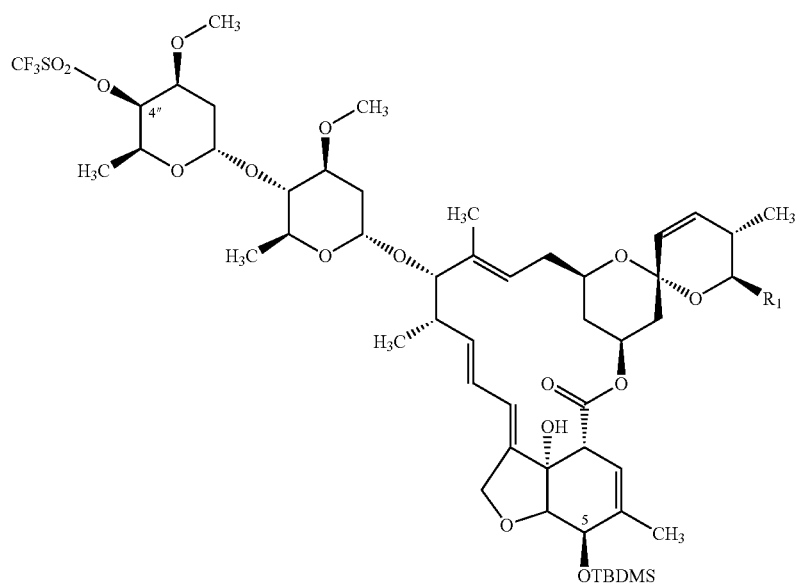

in the form of a pale-yellow foam.

Step 2): To 883 mg of the resulting intermediate in 5 ml of absolute dimethylformamide there are added, with ice-$H_2O$-cooling, 102 mg of sodium azide and stirring is carried out for a further 15 hours. Aqueous working-up using ethyl acetate, water and saturated aqueous NaCl solution, drying ($Na_2SO_4$) and column-chromatographic purification of the crude product on silica gel using ethyl acetate/hexane (1:5) as eluant yields 493 mg of 4"-deoxy-4"-(S)-azido-5-OTBDMS-avermectin B1b and 61 mg of a mixture of 4"-deoxy-4"-(S)-azido-5-OTBDMS-avermectin B1a+1b, both in the form of a colourless dry foam.

In NMR (500 MHz), the title product exhibits the following selected signals (δ, ppm) for the B1a derivative: 0.13 (6H, s, Si($CH_3$)$_2$), 1.49 (3H, brs, $CH_3$-14a) 1.78 (3H, brs, $CH_3$-4a), 2.98 (1H, t, J=9.7 Hz, CH-4"), 3.20 (1H, t, J=9.0 Hz, CH-4'), 3.39 (1H, m, CH-2), 3.42 (3H, s, $OCH_3$), 3.46 (3H, s, $OCH_3$), 3.82 (d, J=5.7 Hz, CH-6), 3.92 (1H, brs, CH-13), 4.09 (1H, s, HO—C-7), 4.43 (1H, m, CH-5), 4.56-4.69 (2H, ABX system, $J_1$=1.5 Hz, $J_2$=14.4 Hz, $CH_2$-8a), 4.75 (1H, d, J=3.0 Hz, CH-1'), 4.99 (1H, m, CH-15), 5.32 (1H, d, J=1 Hz, CH-3), 5.40 (1H, d, J=3.0 Hz, CH-1").

Example A.2

Preparation of 4"-deoxy-4"-(S)-azido-avermectin B1 of Formula

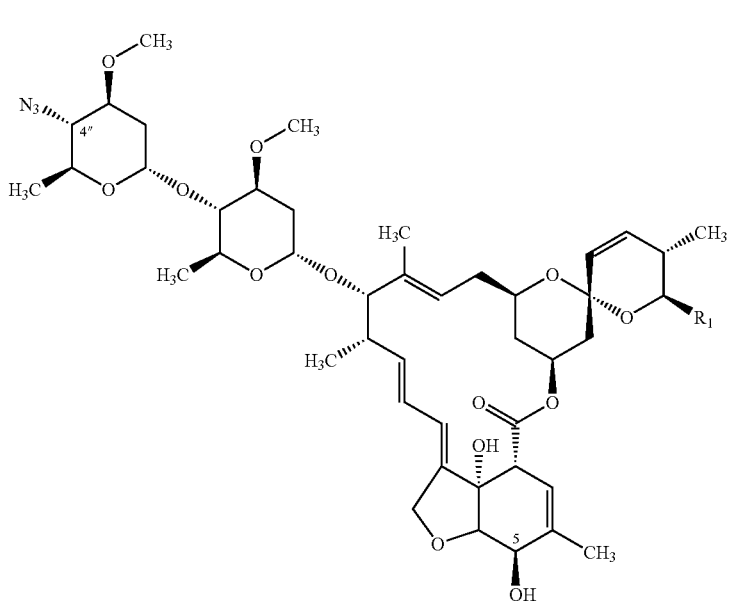

(Va)

To a solution of 805 mg of 4"-deoxy-4"-(S)-azido-5-OTBDMS-avermectin B1 of formula (IVa) in 5 ml of absolute THF under argon there are added, with ice-cooling, 20 ml of HFpyridine reagent in tetrahydrofuran, and the mixture is left to stand at room temperature for 22 hours. The reaction mixture is poured onto cooled saturated aqueous $NaHCO_3$ solution and extracted twice with ether. The combined organic extracts are washed with water and with saturated aqueous NaCl solution (twice in each case), dried over $MgSO_4$ and concentrated by evaporation. The crude product is purified by column chromatography on silica gel using ethyl acetate/hexane (2:5) as eluant.

The title product is thus obtained, which, in NMR (500 MHz), exhibits the following selected signals (δ, ppm) for the B1a derivative: 1.48 (3H, brs, $CH_9$-14a), 1.87 (3H, brs, $CH_3$-4a), 2.98 (1H, t, J=9.8 Hz, CH-4"), 3.20 (1H, t, J=9.0 Hz, CH-4'), 3.29 (1H, m, CH-2), 3.42 (3H, s, $OCH_3$), 3.46 (3H, s, $OCH_3$), 3.92 (1H, brs, CH-13), 3.96 (1H, d, J=6.1 Hz, CH-6), 4.29 (1H, brd, J=5.9 Hz, CH-5), 4.64-4.72 (2H, ABX system, $CH_2$-8a), 4.76 (1H, d, J=3 Hz, CH-1'), 4.98 (1H, dm, J=7.3 Hz, CH-15).

Example A.3

Preparation of 4'-deoxy-4"-(S)-ethylamino-5-OTBDMS-avermectin B1 of Formula

Step 1): 1 g of 4"-deoxy-4"-(S)-azido-5-OTBDMS-avermectin B1 in 50 ml of absolute tetrahydrofuran under argon is stirred together with 2.97 ml of trimethylphosphine (1M in tetrahydrofuran) for 4 hours at 65° C.

Step 2): To the resulting solution from Step 1) there is added 0.224 ml of acetaldehyde and the mixture is stirred at 40° C. for 15 hours. The solution is then concentrated by evaporation in vacuo.

Step 3): The crude product from the previous Step is taken up in 30 ml of methanol; 45 mg of $NaBH_4$ are added and the mixture is stirred at room temperature for 2 hours. The solution is poured onto water and extracted with ethyl acetate. Subsequent washing of the organic phase with saturated aqueous NaCl solution and drying with $Na_2SO_4$ yields the crude product after concentration by evaporation. Purification is carried out on silica gel using $CH_2Cl_2$/MeOH (95:5) as eluant.

4"-Deoxy-4"-(S)-ethylamino-5-OTBDMS-avermectin B1 is thus obtained, which, in NMR (500 MHz), exhibits the following signals (δ, ppm) for the B1a derivative: 0.12 (6H, s, 5-OSi($CH_3$)$_2$), 1.09 (3H, t, J=7 Hz, $\underline{CH_3}CH_2NH$), 1.49 (brs, $CH_3$-14a), 1.78 (3H, brs, $CH_3$-4a), 2.17 (t, J=9.5 Hz, CH-4"), 2.69 (2H, m, $CH_3\underline{CH_2}NH$), 3.22 (1H, t, J=9 Hz, CH-4'), 3.38 (3H, s, $OCH_3$), 3.42 (3H, s, $OCH_3$), 3.82 (1H, d, J=5.7 Hz, (VIa)

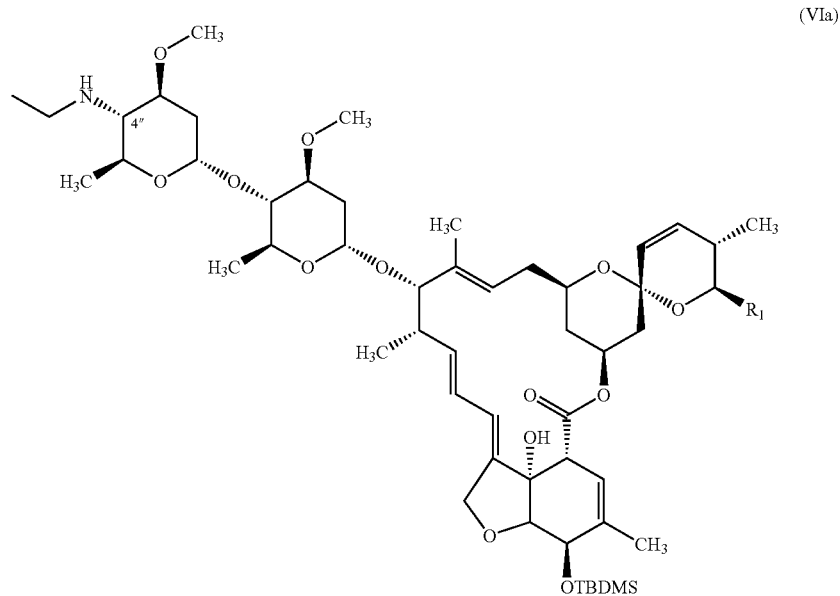

CH-6), 3.92 (1H, brs, CH-13), 4.43 (1H, m, CH-5), 4.56-4.69 (2H, ABX system, $CH_2$-8a), 4.99 (1H, m, CH-15).

Example A.4

4"-Deoxy-4"-(S)-ethylamino-avermecfin B1 of Formula

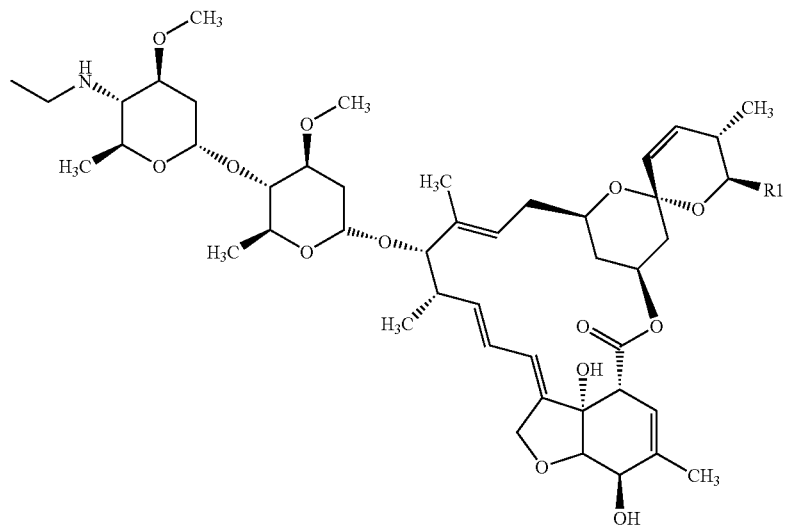

484 mg of 4"-deoxy-4"-(S)-ethylamino-5-OTBDMS-avermectin B1 in 30 ml of methanol under argon are treated for 2 hours with 60 mg of methanesulfonic acid with ice/water cooling. The reaction solution is added to saturated $NaHCO_3$ solution, extracted three times with ethyl acetate, washed with saturated aqueous NaCl solution and dried over $Na_2SO_4$. The crude product, concentrated by evaporation, is purified on silica gel using ethyl acetate/hexane (3:1) as eluant.

Drying in vacuo yields 4"-deoxy-4"-(S)-ethylamino-avermectin B1, which, in NMR (500 MHz), exhibits the following signals (δ, ppm) for the B1 a deriviative: 1.09 (3H, t, J=7.1 Hz, $CH_3CH_2NH$), 1.48 (brs, $CH_3$-14a), 1.86 (3H, brs, $CH_3$-4a), 2.16 (t, J=9.4 Hz, CH-4"), 2.68 (2H, m, $CH_3\underline{CH_2}NH$), 3.22 (1H, t, J=8.9 Hz, CH-4'), 3.29 (1H, m, CH-2), 3.38 (3H, s, $OCH_3$), 3.43 (3H, s, $OCH_3$), 3.92 (brs, CH-13), 3.96 (d, J=6.4 Hz, CH-6), 4.28 (1H, m, CH-5), 4.58-4.76 (2H, ABX system, $CH_2$-8a), 4.75 (1H, d, J=approx. 3 Hz, CH-1'), 4.98 (1H, m, CH-15).

Example A.5

Preparation of 4"-deoxy-4"-(S)—N-ethyl-N-methyl-avermectin B1 of Formula

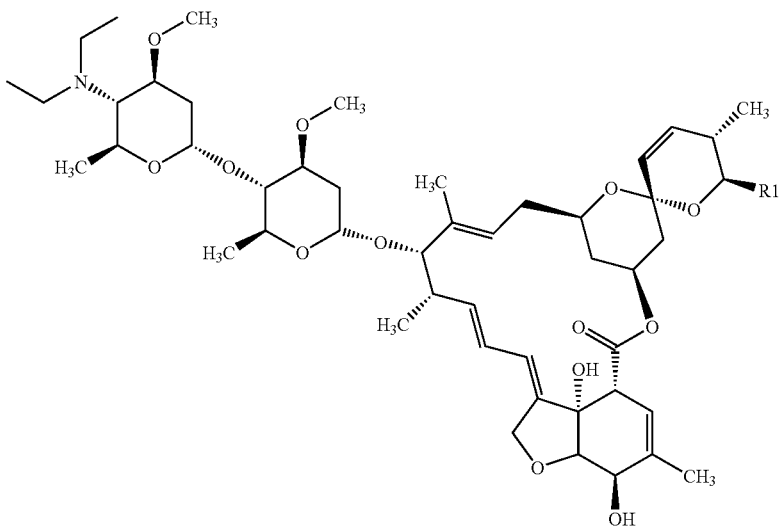

To a solution of 130 mg of 4"-deoxy-4"-(S)-ethylamino-avermectin B1 in 4 ml of methanol under argon there are added, with stirring, a catalytic amount of pivalic acid and 0.310 ml of formaldehyde (37% in water). After 1.75 hours, 11 mg of NaCNBH$_3$ are added and stirring is carried out for a further 2 hours. The reaction solution is poured onto saturated aqueous NaHCO$_3$ solution, extracted three times with ethyl acetate, washed three times with saturated aqueous NaCl solution and dried over Na$_2$SO$_4$. The crude product, concentrated by evaporation, is purified on silica gel using ethyl acetate/hexane (1:2) as eluant and dried in vacuo.

There is thus obtained 4"-deoxy-4"-(S)—N-ethyl-N-methyl-avermectin B1, which, in NMR (500 MHz), exhibits the following selected signals (δ, ppm) for the B1 a derivative: 1.02 (3H, t, J=7.1 Hz, CH$_3$CH$_2$N) 1.48 (3H, brs, CH$_3$-14a), 1.87 (3H, brs, CH$_3$-4a), 2.21 (t, J=9.7 Hz, CH-4"), 2.33 (3H, s, NCH$_3$), 2.65 (2H, q, J=7.1 Hz, CH$_3$CH$_2$N), 3.24 (1H, t, J=9 Hz), 3.29 (1H, m, CH-2), 3.35 (3H, s, OCH$_3$), 3.43 (3H, s, OCH$_3$), 3.93 (brs, CH-13), 3.97 (d, J=6.1 Hz), 4.01 (1H, s, HO—C-7), 4.28 (1H, m, CH-5), 4.64-4.71 (2H, ABX system, CH$_2$-8a), 4.76 (1H, d, J=4.2 Hz, CH'-1'), 4.99 (1H, m, CH-15).

Example A.6

Preparation of 4"-deoxy-4"-(S)—N,N-diethyl-avermectin B1 of Formula

To a two-phase mixture of 50 mg of 4"-deoxy-4"-(S)-ethylamino-avermectin B1 in 5 ml of ethyl acetate and 5.6 ml of 0.1M NaHCO$_3$ in H$_2$O there is added 0.56 ml of ethyl iodide. The reaction mixture is stirred vigorously in a closed vessel at 60-68° C. for 72 hours; it is then poured onto water, extracted with ethyl acetate, washed with saturated aqueous NaCl solution and subsequently dried over Na$_2$SO$_4$. The crude product, concentrated by evaporation, is separated from the unreacted starting material on silica gel using ethyl acetate/hexane (1:1) as eluant.

There is thus obtained 4"-deoxy-4"-(S)—N,N-diethylamino-avermectin B1, which, in NMR (500 MHz), exhibits the following selected signals (δ, ppm) for the B1a derivative: 1.1 (6H, t, J=7 Hz, (CH$_3$CH$_2$)$_2$N, 1.48 (3H, brs, CH$_3$-14a), 1.86 (3H, brs, CH$_3$-4a), 2.31 (t, J=approx. 10 Hz, CH-4"), 2.67 (4H, m, (CH$_3$CH$_2$)$_2$N, 3.26 (1H, t, J=9 Hz, CH-4'), 3.31 (1H, m, CH-2), 3.36 (3H, s, OCH$_3$), 3.44 (3H, s, OCH$_3$), 4.30 (1H, m, CH-5), 4.66-4.74 (2H, ABX system, CH$_2$-8a).

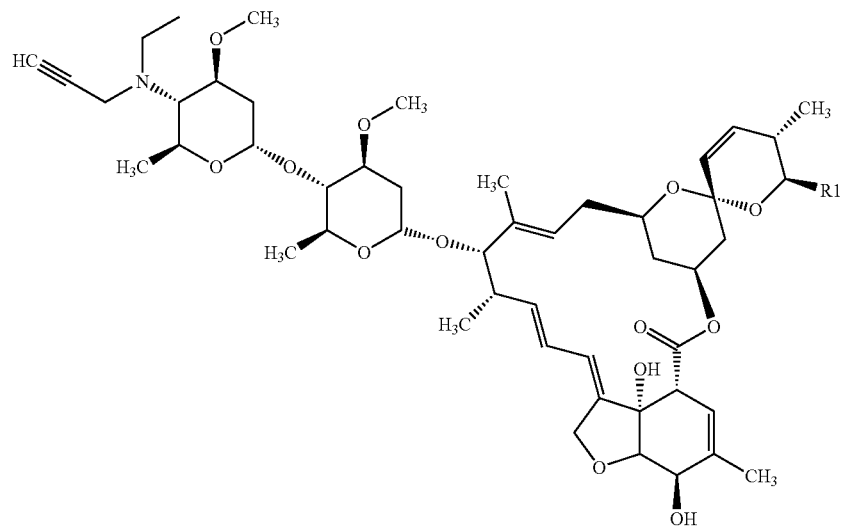

Example A.7

Preparation of 4"-deoxy-4"-(S)—N-ethyl-N-propargylamino-avermectin B1 of Formula

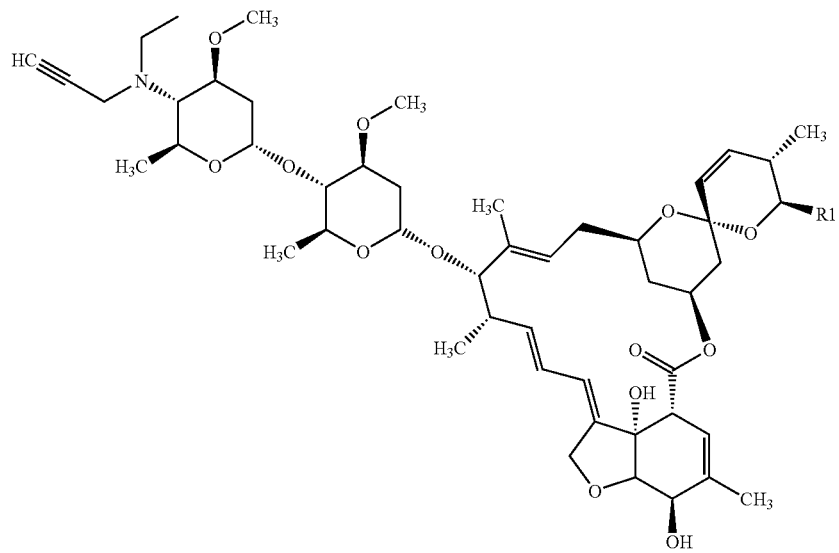

To a two-phase mixture of 50 mg of 4"-deoxy-4"-(S)-ethylamino-avermectin B1 in 3 ml of ethyl acetate and 5.6 ml of 0.1M NaHCO$_3$ in H$_2$O there is added 0.42 ml of propargyl bromide. The reaction mixture is stirred vigorously in a closed vessel at 70° C. for 72 hours; it is then poured onto water, extracted with ethyl acetate, washed with saturated aqueous NaCl solution and then dried over Na$_2$SO$_4$. The crude product, concentrated by evaporation, is purified on silica gel using ethyl acetate/hexane (1:1) as eluant.

There is thus obtained the title product 4"-deoxy-4"-(S)—N-ethyl-N-propargylamino-avermectin B1, which, in NMR (500 MHz), exhibits the following selected signals (δ, ppm) for the B1a derivative: 1.06 (3H, m, CH$_3$CH$_2$N), 1.49 (brs, CH$_3$-14a), 1.87 (3H, brs, CH$_3$-4a), 2.15 (1H, brs, CH≡CHCH$_2$N), 2.28 (t, J=10 Hz, CH-4"), 2.33 (d, J=8 Hz, HO—C-5), 2.65-2.85 (2H, dm, CH$_3$CH$_2$N), 3.23 (1H, t, J=9 Hz, CH-4'), 3.29 (1H, m, CH-2), 3.33 (3H, s, OCH$_3$), 3.43 (3H, s, OCH$_3$), 3.49 (brs, CH═CHCH$_2$N), 3.93 (brs, CH-13), 3.97 (d, J=6.4 Hz, CH-6), 4.01 (1H, s, HO—C-7), 4.28 (1H, m, CH-5), 4.64-4.71 (2H, ABX system, CH$_2$-8a), 5.00 (1H, m, CH-15).

Example A.8

Preparation of 4"-deoxy-4"-(S)-methylamino-5-OT-BDMS-avermectin B1 of Formula

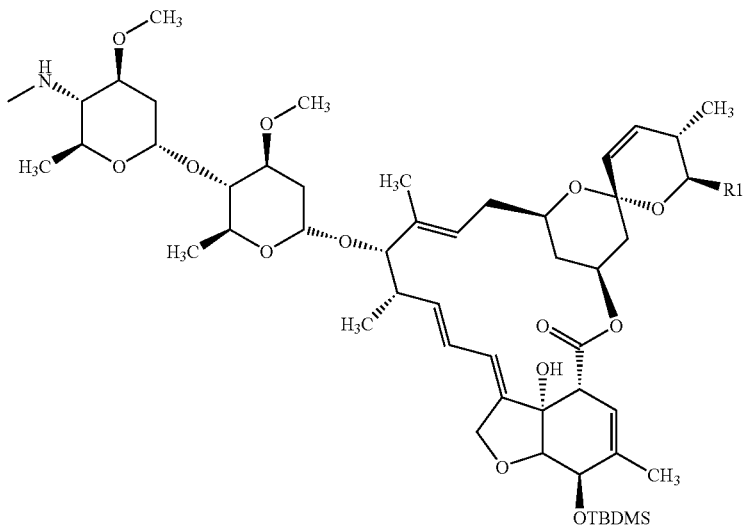

Step 1): A solution of 500 mg of 4"-deoxy-4"-(S)-azido-5-OTBDMS-avermectin B1 and 1.48 ml of trimethylphosphine (1M in tetrahydrofuran) in 40 ml of absolute tetrahydrofuran under argon is left to stand at room temperature for 72 hours.

Step 2): To the resulting solution there are added approximately 15 g of 0.4 nm molecular sieve (in bead form) and also 0.320 ml of formaldehyde (37% in $H_2O$), and the mixture is stirred at 65° C. for 24 hours. Filtration is carried out and the solution is concentrated by evaporation in vacuo and dried to constant weight. The imine intermediate is obtained in the form of a colourless dry foam.

Step 3): The intermediate from Step 2) is taken up in 30 ml of methanol; a spatula tip of pivalic acid and 22.5 mg of $NaBH_4$ are added and stirring is carried out at room temperature for 2 hours. The mixture is then poured onto water, extracted with ethyl acetate, washed with saturated NaCl solution and dried over $Na_2SO_4$. The crude product obtained is purified on silica gel using $CH_2Cl_2$/MeOH (95:5) as eluant.

There is thus obtained 4'-deoxy-4"-(S)-methylamino-5-OTBDMS-avermectin B1, which, in NMR (500 MHz), exhibits the following selected signals (δ, ppm) for the B1a derivative: 0.12 (6H, s, $Si(CH_3)_2$), 1.49 (brs, $CH_3$-14a), 1.78 (brs, $CH_3$-4a), 2.10 (1H, t, J=9.5 Hz, CH-4"), 2.46 (3H, s, $CH_3NH$), 3.23 (t, J=9 Hz, CH-4'), 3.38 (3H, s, $OCH_3$), 3.42 (3H, s, $OCH_3$), 3.92 (1H, brs, CH-13), 4.42 (1H, m, CH-5), 4.56-4.69 (2H, ABX system, $J_1$=2.2 Hz, $J_2$=14.2 Hz, $CH_2$-8a), 4.76 (1H, d, J=3.9 Hz, CH-1'), 4.99 (1H, m, CH-15).

Example A.9

Preparation of
4"-deoxy-4"-(S)-methylamino-avermectin B1 of Formula

Synthesis Variant a)

A solution of 250 mg of 4"-deoxy-4"-(S)-methylamino-5-OTBDMS-avermectin B1 in 20 ml of methanol is treated, at 0-5° C., with 31 mg of methanesulfonic acid for 5 hours. The reaction solution is added to saturated $NaHCO_3$ solution. The mixture is extracted three times with ethyl acetate, washed three times with saturated NaCl solution and dried with $Na_2SO_4$. 230 mg of crude product are obtained. Purification on silica gel using $CH_2Cl_2$/MeOH (95:5) as eluant yields the desired product in the form of a colourless dry foam after drying under a high vacuum.

Synthesis Variant b)

Step 1): 300 mg of 4"-deoxy-4"-(S)-azido-avermectin B1 are stirred in 25 ml of absolute tetrahydrofuran under argon with 1.67 ml of trimethylphosphine (1M in tetrahydrofuran) for 12 hours at room temperature and then for 24 hours at 65° C.

Step 2): To the resulting solution there are added 15 g of 0.4 nm molecular sieve (in bead form) and also 0.217 ml of formaldehyde (37% in $H_2O$) and the mixture is stirred at 70° C. for 24 hours.

Step 3): The intermediate from Step 2) is dissolved in 15 ml of methanol, and 15 mg of $NaBH_4$ are added. After stirring for 5 hours, the mixture is poured onto water, extracted with ethyl acetate, washed with saturated aqueous NaCl solution and dried over $Na_2SO_4$. The crude product is purified on silica gel using $CH_2Cl_2$/MeOH (95:5) as eluant.

There is thus obtained 4"-deoxy-4"-(S)-methylamino-avermectin B1, which, in NMR (500 MHz), exhibits the following selected signals (δ, ppm) for the B1a derivative: 1.15 (3H, d, J=7.1 Hz), 1.23 (3H, d, J=6.1 Hz), 1.27 (3H, d, J=6.4 Hz), 1.48 (3H, brs, $CH_3$-14a), 1.86 (3H, brs, $CH_3$-4a), 2.09 (1H, t, J=9.6 Hz, CH-4"), 2.46 (3H, s, $CH_3NH$), 3.23 (1H, t, J=9 Hz, CH-4'), 3.29 (1H, m, CH-2), 3.38 (3H, s, $OCH_3$), 3.43 (3H, s, $OCH_3$), 3.92 (1H, brs, CH-13), 3.96 (1H,

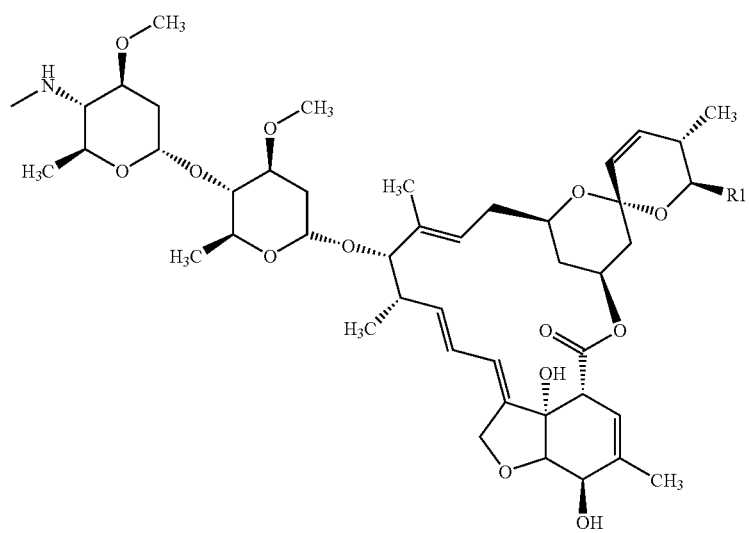

d, J=6.2 Hz, CH-6), 4.29 (1H, dm, J=6.2 Hz, CH-5), 4.64-4.71 (2H, ABX system, CH$_2$-8a), 4.99 (1H, m, CH-15).

Example A.10

Preparation of 4"-deoxy-4"-(S)—N-2-propenyl-N-methylamino-avermectin B1 of Formula

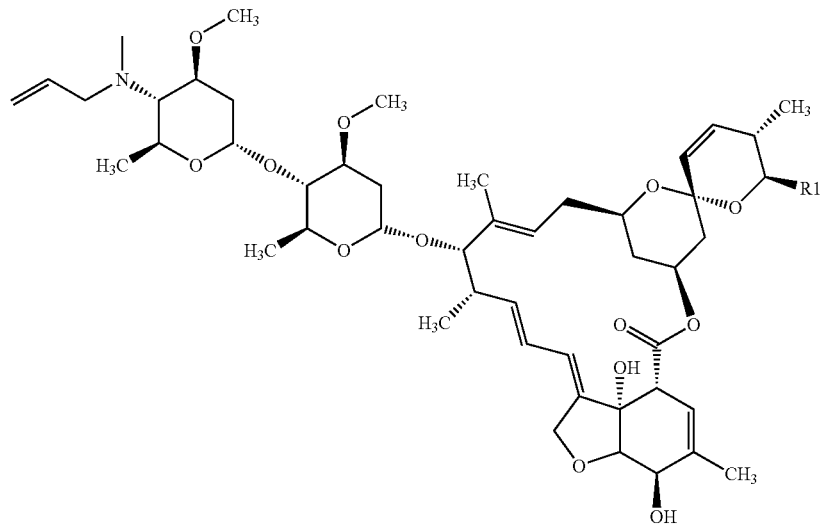

To a two-phase solution consisting of 84 mg of 4"-deoxy-4"-(S)-methylamino-avermectin B1 in 5 ml of ethyl acetate and 9.5 ml of 0.1M NaHCO$_3$ in H$_2$O there is added 0.80 ml of allyl bromide. The reaction mixture is stirred vigorously in a closed vessel, first for 18 hours at room temperature and then for 12 hours at 40° C. The mixture is then poured onto water, extracted with ethyl acetate, washed with saturated aqueous NaCl solution and dried over Na$_2$SO$_4$. The crude product, concentrated by evaporation, is purified on silica gel using ethyl acetate/hexane (1:1) as eluant.

There is thus obtained 4"-deoxy-4"-(S)—N-2-propenyl-N-methylamino-avermectin B1, which, in NMR (500 MHz), exhibits the following selected signals (δ, ppm) for the B1a derivative: 1.48 (brs, CH$_3$-14a), 1.86 (3H, brs, CH$_3$-4a), 2.23 (t, J=9.7 Hz, CH-4"), 2.30 (s, NCH$_3$), 3.24 (t, J=9.1 Hz, CH-4'), 3.29 (m, CH-2), overlapped by 3.28 (m, N CH$_2$CH=CH$_2$), 3.36 (3H, s, OCH$_3$), 3.43 (3H, s, OCH$_3$), 3.93 (brs, CH-13), 3.96 (1H, d, J=6.3 Hz, CH-6), 4.01 (1H, s, HO—C(7)), 4.28 (1H, m, CH-5), 4.64-4.70 (2H, ABX system, CH$_2$-8a), 4.75 (1H, d, J=approx. 3 Hz, CH-1'), 4.99 (1H, m, CH-15), 5.03-5.16 (2H, m, NCH$_2$CH=CH$_2$).

Example P:11

Preparation of 4"-deoxy-4"-(S)—N-isopropyl-N-methylamino-avermectin B1 of Formula

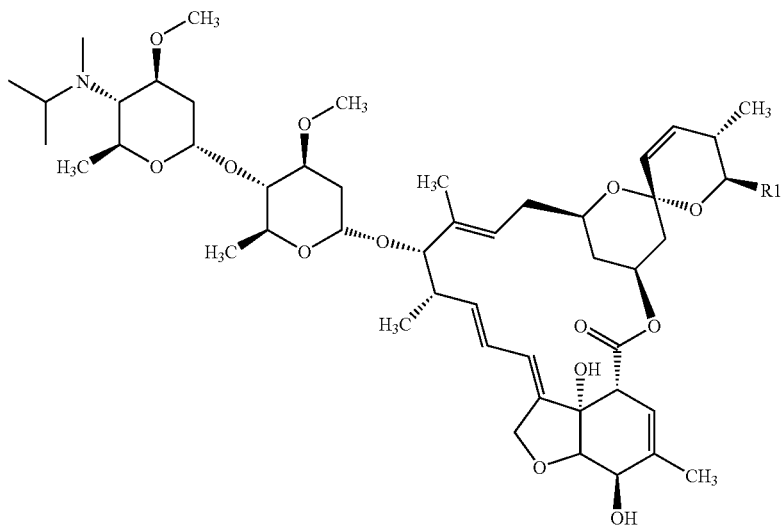

To a mixture consisting of 100 mg of 4"-deoxy-4"-(S)-methylamino-avermectin B1 in 5 ml of ethyl acetate and 11.3 ml of NaHCO₃ (0.1M in H₂O) there is added 0.226 ml (20 eq.) of 2-iodopropane, and heating is carried out, with vigorous stirring, at 75° C. for 72 h. The mixture is poured onto water, extracted with ethyl acetate, washed with saturated NaCl solution and dried with Na₂SO₄. From that crude mixture there is isolated, besides unreacted starting material, the desired compound (column chromatography on silica gel using CH₂Cl₂/MeOH (9:1) as eluant).

There is thus obtained 4"-deoxy-4"-(S)—N-isopropyl-N-methylamino-avermectin B1a, which, in NMR (500 MHz), exhibits the following selected signals (δ, ppm) for the B1a derivative: 1.03 (6H, t, J=6.6 Hz, NCH(CH₃)₂),1.48 (brs, CH₃-14a), 1.87 (3H, brs, CH₃-4a), 2.31 (t, J=9.7 Hz, CH-4"), 2.32 (d, J=8.3 Hz, HO—C-5), 2.91 (1H, sep, J=6.6 Hz, NCH(CH₃)₂), 3.25 (1H, t, J=8.9 Hz, CH-4'), 3.29 (1H, m, CH-2), 3.33 (3H, s, OCH₃), 3.43 (3H, s, OCH₃), 3.93 (brs, CH-13), 3.96 (1H, d, 6.1 Hz, CH-6), 4.01 (1H, s, HO—C-7), 4.28 (1H, m, CH-5), 4.64-4.71 (2H, ABX system, CH₂-8a), 4.76 (1H, d, J=approx. 3 Hz, CH-1'), 4.99 (1H, m, CH-15).

Example A.12

Preparation of 4"-deoxy-4"-(S)-amino-5-OTBDMS-avermectin B1 of Formula

Step 1): A solution of 500 mg of 4"-deoxy-4"-(S)-azido-5-OTBDMS-avermectin B1 and 1.48 ml of trimethylphosphine (1M in tetrahydrofuran) in 40 ml of absolute tetrahydrofuran under argon is left to stand at room temperature for 72 hours.

Step 2): To the solution from Step 1) there are added 6 ml of 0.1N aqueous ammonium hydroxide, and the mixture is left to stand for 15 hours. The solution is poured onto water, extracted three times with ethyl acetate, neutralised with water and a small amount of dilute sulfuric acid, washed with saturated aqueous NaCl solution and dried over Na₂SO₄. The crude product, concentrated by evaporation, is purified on silica gel using CH₂Cl₂/MeOH (95:5) as eluant.

There is thus obtained 4"-deoxy-4"-(S)-amino-5-OTBDMS-avermectin B1, which, in NMR (500 MHz), exhibits the following selected signals (δ, ppm) for the B1a derivative: 0.13 (6H, s, Si(CH₃)₂), 1.49 (brs, CH₃-14a), 1.78 (brs, CH₃-4a), 2.46 (t, J=9.4 Hz, CH-4"), 3.22 (1H, t, J=9 Hz, CH-4'), 3.40 (s, OCH₃), 3.43 (s, OCH₃), 3.82 (d, J=6.6 Hz, CH-6), 3.92 (1H, brs, CH-13), 4.05-4.13 (2H, br, NH₂), 4.42 (1H, m, CH-5), 4.56-4.69 (2H, ABX system, CH₂-8a), 4.76 (1H, d, J=approx. 3 Hz), 4.99 (1H, m, CH-15).

Example A.13

Preparation of 4"-deoxy-4"-(S)-amino-avermectin B1 of Formula

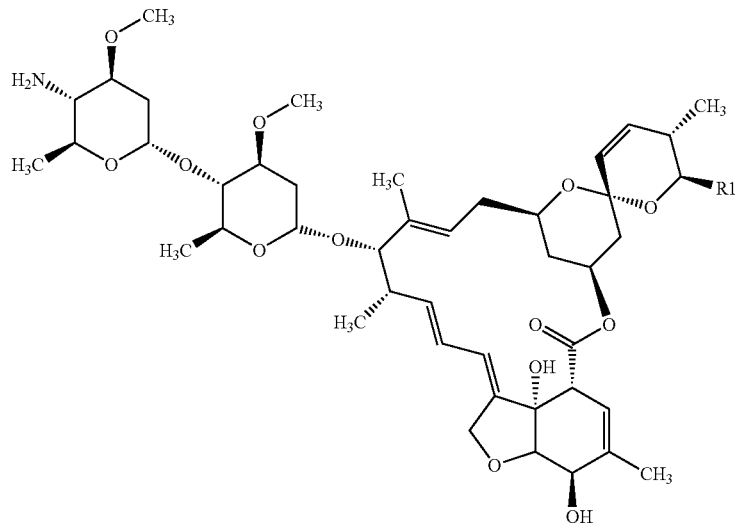

a) Variant 1

255 mg of 4"-deoxy-4"-(S)-amino-5-OTBDMS-avermectin B1 and 32 mg of methanesulfonic acid in 20 ml of methanol are stirred at 0° C. for 5 hours. The solution is poured onto water, extracted with ethyl acetate, washed with saturated aqueous NaCl solution and dried (Na$_2$SO$_4$). The crude product, concentrated by evaporation, is purified on silica gel using CH$_2$Cl$_2$/MeOH (95:5) as eluant. After drying, the title product is obtained.

b) Variant 2

Step 1): 1.41 g of 4"-deoxy-4"-(S)-azido-avermectin B1 in 100 ml of absolute tetrahydrofuran under argon are stirred with 7.85 ml of trimethylphosphine (1M in tetrahydrofuran) at 50° C. for 48 hours.

Step 2): To the solution from Step 1) there are added 30 ml of NaOH (0.001N) and heating is carried out at 45° C. for 18 hours. The mixture is poured onto water and extracted three times with ethyl acetate. The organic phase is washed with saturated aqueous NaCl solution and dried over Na$_2$SO$_4$. Purification of the crude product is carried out on silica gel using CH$_2$Cl$_2$/MeOH (95:5) as eluant.

There is thus obtained 4"-deoxy-4"-(S)-amino-avermectin B1, which, in NMR (500 MHz), exhibits the following selected signals (δ, ppm) for the B1a derivative: 1.48 (brs, CH$_3$-14a), 1.86 (brs, CH$_3$-4a), 2.46 (t, J=9.4 Hz, CH-4"), 3.22 (1H, t, J=9 Hz, CH-4'), 3.29 (1H, m, CH-2), 3.39 (s, OCH$_3$), 3.43 (s, OCH$_3$), 3.93 (brs, CH-13), 3.96 (d, J=6.1 Hz, CH-6), 4.28 (1H, m, CH-5), 4.64-4.71 (2H, ABX system, CH$_2$-8a), 4.76 (1H, d, J=approx. 3 Hz, CH-1'), 4.99 (1H, m, CH-15).

Example A.14

Preparation of 4"-deoxy-4"-(S)—N,N-dimethylamino-avermectin B1 of Formula

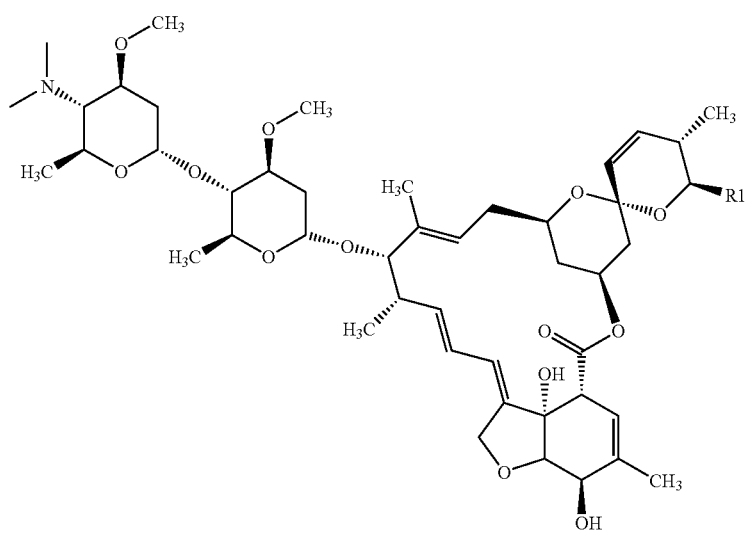

123 mg of 4"-deoxy-4"-(S)-amino-avermectin B1 and 100 mg of pivalic acid in 2 ml of acetonitrile are treated, for 2 hours, with 57 mg of formaldehyde (37% in H$_2$O) at room temperature. The reaction mixture is then poured onto saturated aqueous NaHCO$_3$ solution and extracted twice with ethyl acetate. The combined organic extracts are washed with saturated aqueous NaCl solution (twice) and dried over Na$_2$SO$_4$. The crude product is purified on silica gel in ethyl acetate/hexane (1:3) to (2:1). The title product is obtained in the form of a colourless, dry foam.

There is thus obtained 4"-deoxy-4"-(S)—N,N-dimethylamino-avermectin B1, which, in NMR (500 MHz), exhibits the following selected signals (δ, ppm) for the B1a derivative: 1.48 (brs, CH$_3$-14a), 1.87 (3H, brs, CH$_3$-4a), 2.14 (1H, t, J=9.7 Hz, CH-4"), 2.41 (6H, s, (CH$_3$)$_2$N), 3.24 (1H, t, J=9 Hz, CH-4'), 3.29 (1H, m, CH-2), 3.35 (3H, s, OCH$_3$), 3.43 (3H, s, OCH$_3$), 3.93 (1H, brs, CH-13), 3.96 (1H, d, J=6.4 Hz, CH-6), 4.01 (1H, s, HO—C-7), 4.28 (1H, m, CH-5), 4.64-4.70 (2H, ABX system, CH$_2$-8a), 4.75 (1H, d, J=approx. 3 Hz, CH-1'), 4.99 (1H, m, CH-15).

Example A.15

Preparation of 4"-deoxy-4"-(S)-(piperidin-1-yl)-avermectin B1

A solution of 100 mg of 4"-deoxy-4"-(S)-amino-avermectin B1, 40 mg of 1,5-dibromopentane and 0.016 ml of triethylamine in a mixture of 4 ml of THF and 1 ml of ethyl acetate is stirred at room temperature for 3 days. The solution is poured onto water, extracted with ethyl acetate, washed with saturated aqueous NaCl solution and dried over Na$_2$SO$_4$. The desired product is isolated from the crude mixture with the aid of column chromatography on silica gel in CH$_2$Cl$_2$/MeOH (9:1) as eluant.

There is thus obtained 4"-deoxy-4"-(S)-(piperidin-1-yl)-avermectin, which, in NMR (500 MHz), exhibits the following selected signals (δ, ppm) for the B1a derivative: 1.48 (brs, CH$_3$-14a), 1.87 (brs, CH$_3$-4a), 2.06 (t, J=9.8 Hz, CH-4"), 2.32 (d, J=8.3 Hz, HO—C-5), 2.56 and 2.77 (2 m, 4H, N(CH$_2$)$_2$), 3.23 (1H, t, J=9 Hz, CH-4'), 3.36 (3H, s, OCH$_3$), 3.42 (3H, s, OCH$_3$), 3.93 (1H, brs, CH-13), 3.96 (1H, d, J=6.1 Hz, CH-6), 4.01 (1H, s, HO—C-7), 4.28 (1H, m, CH-5), 4.64-4.71 (2H, ABX system, CH$_2$-8a), 4.75 (1H, d, J=approx. 3 Hz, CH-1'), 4.99 (1H, m, CH-15).

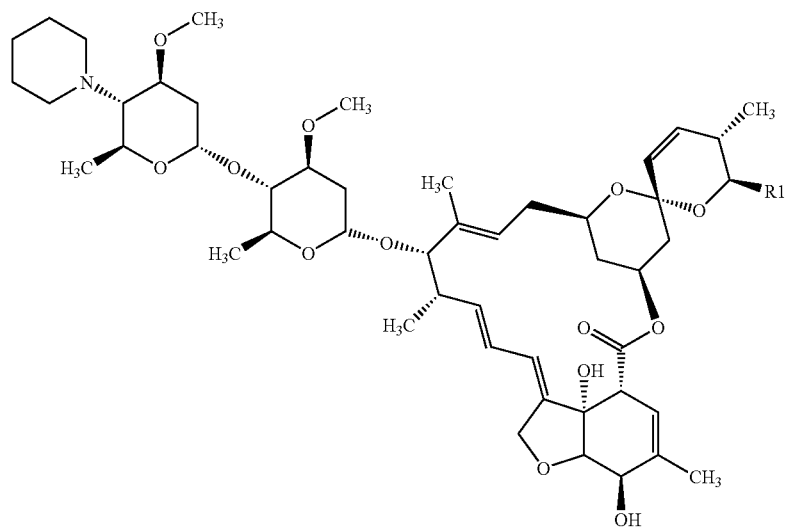

Example A.16

Preparation of the Benzoate Salt of 4'-deoxy-4'-(S)—N,N-dimethylamino-avermectin B1

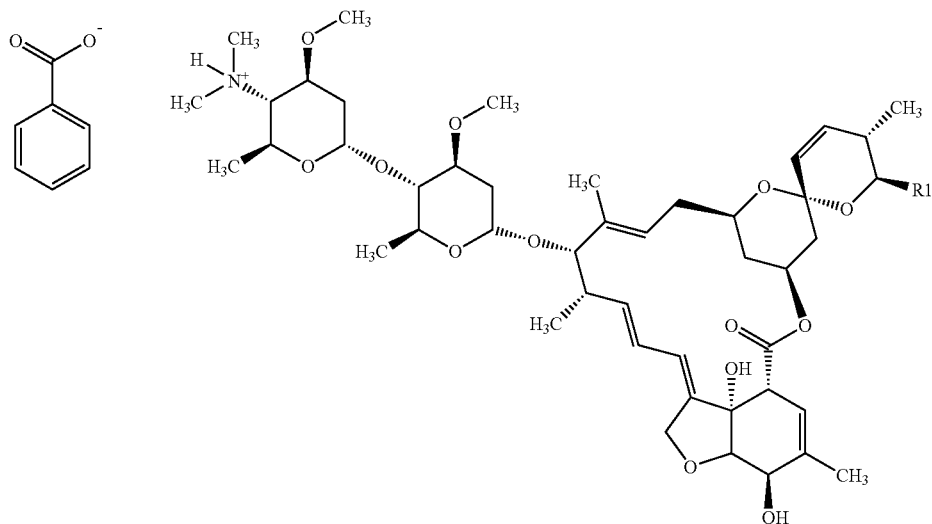

100 mg of 4"-deoxy-4"-(S)—N,N-dimethylamino-avermectin B1 and 14 mg of benzoic acid are dissolved in 20 ml of diethyl ether and concentrated to dryness by evaporation. The desired salt is thus obtained.

In analogous manner, the 1:1 salts of 4"-deoxy-4"-(S)—N,N-dimethylamino-avermectin B1 with isobutyric acid, salicylic acid, 2,5-dimethylbenzoic acid, thiosalicylic acid, 4-phenoxybutyric acid and citric acid are also prepared.

In analogous manner to Example A.16, the 1:1 salts of 4"-deoxy-4"-(S)—N-methylamino-avermectin B1 with benzoic acid, isobutyric acid, salicylic acid, 2,5-dimethylbenzoic acid, thiosalicylic acid, 4-phenoxybutyric acid and citric acid are also prepared.

Example A.17

Preparation of 4"-deoxy-4"-(S)—N-isopropylamino-avermectin $B_1$

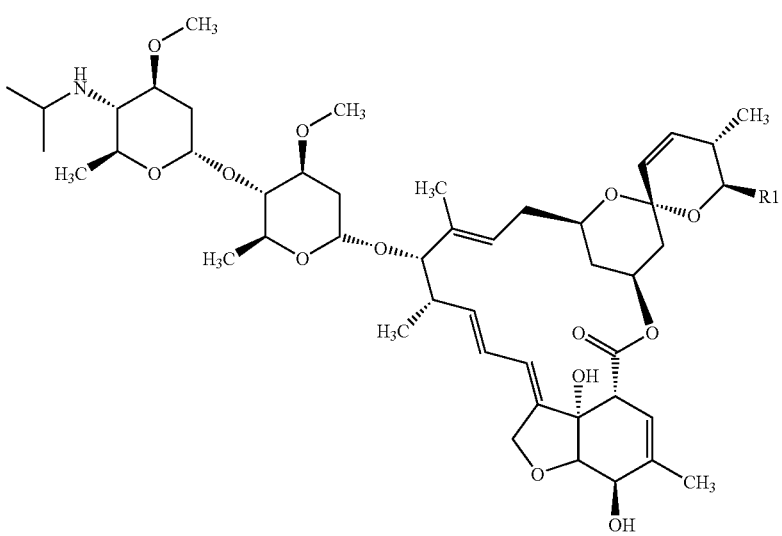

150 mg of 4"-(S)-amino-avermectin $B_1$ in 5 ml of THF are kept at room temperature for 15 hours together with 0.050 ml of acetone and 0.3 ml of ethyl acetate/water (9:1). Treatment with 8.5 mg of $NaBH_4$ is then carried out for 4 hours. The mixture is poured onto an ice-water mixture and extracted 3 times with ethyl acetate. The combined organic extracts are washed with saturated sodium chloride solution and dried with Na$_2$SO$_4$. Purification is carried out on silica gel using CH$_2$Cl$_2$/MeOH (95:5) as eluant.

There is thus obtained the title product, which, in NMR (500 MHz), exhibits the following selected signals (δ, ppm) for the B1a derivative: 1.05 (d overlapped, CH(CH$_3$)$_2$, 1.48 (brs, CH$_3$-14a), 1.86 (3H, brs, CH$_3$-4a), 2.24 (t, J=10.3 Hz, CH-4"), 2.90 (1H, m, NCH(CH$_3$)$_2$), 3.21 (t, J=9.1 Hz, CH-4'), 3.29 (1H, m, CH-2), 3.38 (3H, s, OCH$_3$), 3.43 (3H, s, OCH$_3$), 3.92 (1H, brs, CH-13), 3.96 (1H, d, J=6.3 Hz, CH-6), 3.99 (1H, s, HO—C(7)), 4.29 (1H, m, CH-5), 4.64-4.71 (2H, ABX system, CH$_2$-8a), 4.76 (1H, d, J=approx. 3 Hz, CH-1'), 4.99 (1H, m, CH-15).

The compounds listed in Tables A and 1 to 6 can also be prepared analogously to the above Preparation Examples. In Tables 1 to 6, the symbol ⌇⌇⌇indicates the bond by way of which the corresponding radical is attached to the nitrogen atom of the basic structure.

Because the compounds are, in most cases, present as mixtures of the avermectin derivatives B1a and B1b, characterisation by means of the usual physical data, such as melting point and refractive index, makes little sense. The compounds are therefore characterised, as indicated in the above Examples, after chromatographic purification, by means of NMR spectroscopy or using the retention times that are determined in HPLC analysis (high-resolution liquid chromatography). The indication B1a in the Tables relates to the main component, wherein R$_1$ is sec-butyl, the content of which is usually greater than 80%. B1b stands for the subsidiary component, wherein R$_1$ is isopropyl. In the case of compounds where a retention time is indicated only in the B1a column, it is not possible to determine the retention time for the B1b component because of the low B1b derivative content. Assignment of the correct structures of the B1a and B1b components is carried out by mass spectrometry.

The following method is used for the HPLC analysis:

| HPLC gradient conditions | | | | |
|---|---|---|---|---|
| solvent A: 0.01% trifluoroacetic acid in H$_2$O | | | | |
| solvent B: 0.01% trifluoroacetic acid in CH$_3$CN | | | | |
| time [min] | A [%] | B [%] | flow rate 1 [µl/min] | flow rate 2 [ml/min] |
| 0 | 80 | 20 | 500 | 3.5 |
| 0.1 | 50 | 50 | 500 | 3.5 |
| 10 | 5 | 95 | 500 | 3.5 |
| 15 | 0 | 100 | 500 | 3.5 |
| 17 | 0 | 100 | 500 | 3.5 |
| 17.1 | 80 | 20 | 500 | 3.5 |
| 22 | 80 | 20 | 500 | 3.5 |
| column: | YMC-Pack ODS-AQ 1 | | YMC-Pack ODS-AQ 2 | |
| column length: | 125 mm | | 30 mm | |
| column internal diameter: | 2 mm | | 4.6 mm | |
| temperature: | 40° C. | | 40° C. | |

The YMC-Pack ODS-AQ column used for chromatography of the compounds is manufactured by YMC, Alte Raesfelderstrasse 6, 46514 Schermbeck, Germany. For the HPLC analysis of compounds A.18 to A.34 of table A and of table 1, and for the compounds 1.70 and 1,159, flow rate 1 and YMC-Pack ODS-AQ 1 conditions were used, for all other compounds, flow rate 2 and YMC-Pack ODS-AQ 2 conditions were used.

TABLE A

Compounds of formula

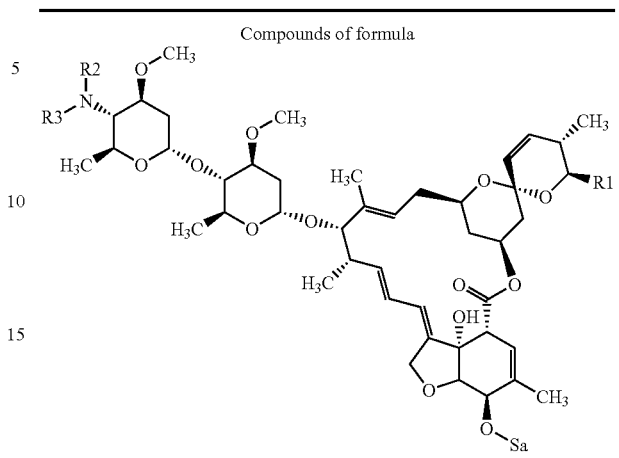

wherein R$_1$ is sec-butyl (B1a) or isopropyl (B1b).

| | R$_2$ | R$_3$ | Sa | LC B$_{1a}$ (min) | LC B$_{1b}$ (min) |
|---|---|---|---|---|---|
| A.18 | H | CH$_3$CH$_2$CH$_2$ | TBDMS | 9.87 | — |
| A.19 | H | CH$_3$CH$_2$CH$_2$ | H | 5.47 | — |
| A.20 | H | PhOH$_2$ | TBDMS | 10.03 | — |
| A.21 | H | PhOH$_2$ | H | 5.92 | — |
| A.22 | CH$_3$ | PhOH$_2$ | H | 6.72 | 6.13 |
| A.23 | CH$_3$ | CH$_3$CH$_2$OH$_2$ | H | 5.57 | — |
| A.24 | CH$_3$ | propargyl | H | 6.67 | 6.14 |
| A.25 | CH$_3$ | C$_2$H$_5$OCOCH$_2$ | H | 7.74 | 7.15 |
| A.26 | CH$_3$ | CH$_3$OCOCH$_2$ | H | 7.63 | 7.09 |
| A.27 | CH$_3$ | 4-F—PhCH$_2$ | H | 7.10 | 6.56 |
| A.28 | C$_2$H$_5$ | C$_2$H$_5$OCOCH$_2$ | H | 8.81 | — |
| A.29 | C$_2$H$_5$ | allyl | H | 6.00 | 5.51 |
| A.30 | C$_3$H$_7$(n) | propargyl | H | 8.94 | 8.40 |
| A.31 | C$_3$H$_7$(n) | C$_2$H$_5$ | H | 5.98 | — |
| A.32 | C$_3$H$_7$(n) | C$_2$H$_5$OCOCH$_2$ | H | 9.82 | 9.34 |
| A.33 | —(CH$_2$)$_4$— | | H | 6.88 | 6.38 |
| A.34 | —(CH$_2$)$_3$— | | H | 5.11 | 4.75 |

TABLE 1

Compounds of formula (I) wherein R$_1$ is sec-butyl (B1a) or isopropyl (B1b) and R$_2$ is hydrogen.

| | | Retention time (min.) | |
|---|---|---|---|
| No. | R$_3$ | B1a | B1b |
| 1.001 | 9-anthracenylmethyl | | |
| 1.002 | (2-hydroxy-3-methoxy-phenyl)methyl | | |
| 1.003 | (3-nitrophenyl)methyl | | |
| 1.004 | (4-dimethylaminophenyl)methyl | | |
| 1.005 | (3-bromophenyl)methyl | | |
| 1.006 | (2-nitro-5-hydroxy-phenyl)methyl | | |
| 1.007 | 2-phenyl-n-propyl | | |
| 1.008 | 3-pyridyl-methyl | | |
| 1.009 | (2,4-dimethylphenyl)methyl | | |
| 1.010 | (3-fluorophenyl)methyl | | |
| 1.011 | neopentyl | | |

TABLE 1-continued

Compounds of formula (I) wherein $R_1$ is sec-butyl (B1a) or isopropyl (B1b) and $R_2$ is hydrogen.

| No. | $R_3$ | Retention time (min.) B1a | B1b |
|---|---|---|---|
| 1.012 | [structure: CH₂-phenyl-COOH (meta)] | | |
| 1.013 | [structure: CH₂-phenanthrenyl] | | |
| 1.014 | (3,4-methylenedioxy-6-nitrophenyl)methyl | | |
| 1.015 | [structure: CH₂-(4-methoxynaphthalenyl)] | | |
| 1.016 | (2-hydroxy-5-methoxyphenyl)methyl | | |
| 1.017 | (2-hydroxy-4-methoxyphenyl)methyl | | |
| 1.018 | (2,3-dihydroxyphenyl)methyl | | |
| 1.019 | (2-hydroxy-5-nitrophenyl)methyl | | |
| 1.020 | [structure: CH₂-(2-methoxynaphthalenyl)] | | |
| 1.021 | dec-4-en-1-yl | | |
| 1.022 | (3-[4-methoxyphenoxy]-phenyl)methyl | | |
| 1.023 | [structure: CH₂-CH(CH₃)₂ isobutyl] | | |
| 1.024 | 3-phenyl-n-propyl | | |
| 1.025 | 4-pyridyl-methyl | | |
| 1.026 | [structure: CH₂-(4-methylimidazol-5-yl)] | | |
| 1.027 | ethyl | | |
| 1.028 | n-butyl | 2.48 | 2.32 |
| 1.029 | [structure: CH₂-CH=CH-phenyl] | | |
| 1.030 | (2-bromophenyl)methyl | | |
| 1.031 | [structure: CH₂-imidazol-2-yl] | | |
| 1.032 | [structure: CH₂-(5-methylfuran-2-yl)] | | |
| 1.033 | (4-n-propoxyphenyl)methyl | | |
| 1.034 | [structure: CH₂-phenyl-CH=CH-phenyl] | | |
| 1.035 | (2-chloro-4-hydroxyphenyl)methyl | | |
| 1.036 | cyclododecyl | | |
| 1.037 | 1-methyl-n-butyl | | |
| 1.038 | 4-hydroxy-1-methyl-n-butyl | | |
| 1.039 | 1-methyl-n-propyl | | |
| 1.040 | [structure: CH₂-CH(CH₃)-CH₂CH₂CH₂-C(CH₃)₂-OH] | | |
| 1.041 | (4-tert-butyl-phenyl)methyl | | |
| 1.042 | 3-phenyl-n-butyl | | |
| 1.043 | [structure: CH₂-phenyl-O-CH₂-phenyl] | | |
| 1.044 | —CH₂—C(=O)—O—CH₂-phenyl | 2.70 | — |
| 1.045 | —CH₂—C(=O)—O-methyl | 2.40 | 2.23 |
| 1.046 | —CH₂—C(=O)—O-ethyl | 2.44 | 2.35 |
| 1.047 | [structure: CH(CH₃)-CH₂-C(=O)-CH₃] | | |
| 1.048 | [structure: CH(CH₃)-(1-methylcyclopropyl)] | | |
| 1.049 | [structure: dimethyl 3-substituted glutarate] | | |

TABLE 1-continued

Compounds of formula (I) wherein $R_1$ is sec-butyl (B1a) or isopropyl (B1b) and $R_2$ is hydrogen.

| No. | $R_3$ | Retention time (min.) B1a | B1b |
|---|---|---|---|
| 1.050 | [CH₂-CH=CH-C≡C-C(CH₃)₃, trans] | | |
| 1.051 | [CH₂-CH=CH-C≡C-C(CH₃)₃, cis] | | |
| 1.052 | [CH(CH₃)-CH₂-P(=O)(OMe)₂] | | |
| 1.053 | [tetrahydropyran-4-yl] | | |
| 1.054 | 1,2-dimethyl-3-hydroxy-n-propyl | | |
| 1.055 | cyclobutyl | | |
| 1.056 | [CH(CH₃)-CH₂-C(=O)-NH-tBu] | | |
| 1.057 | [CH(CH₃)-CH(OMe)₂] | | |
| 1.058 | —CH₂C(=O)—O-isopropyl | | |
| 1.059 | —CH₂—C(=O)—O—CH₂—CH₂—O—CH₃ | | |
| 1.060 | —CH₂C(=O)—O-tert-butyl | 2.61 | 2.48 |
| 1.061 | —CH₂C(=O)NH₂ | 2.19 | — |
| 1.062 | [CH(CH₃)-C(=O)-OMe] | | |
| 1.063 | [CH₂-CH(OH)-CH(OH)-CH(OH)-CH(OH)-CH₂OH] | | |
| 1.064 | propargyl | | |
| 1.065 | 2-chloroallyl | | |
| 1.066 | 3,3-dichloroallyl | | |
| 1.067 | [CH₂-(2-chlorothiazol-5-yl)] | | |
| 1.068 | [CH₂-(6-chloropyridin-3-yl)] | | |
| 1.069 | [CH(CH₃)-CH₂-O-CH₃] | | |
| 1.070 | [CH₂-(furan-2-yl)] | 5.45 | 5.07 |
| 1.071 | 1-cyclopropyl-ethyl | | |
| 1.072 | [tetrahydrothiopyran-4-yl] | | |
| 1.073 | [CH(CH₃)-C(=O)-O-Et] | | |
| 1.074 | [CH(CH₃)-CH₂-C(=O)-OH] | | |
| 1.075 | [CH₂-C(CH₃)₃] | | |
| 1.076 | [CH(Et)₂] | | |
| 1.077 | [CH(CH₃)-CH(CH₃)₂] | | |
| 1.078 | [CH(CF₃)-CH₂-C(=O)-O-Et] | | |
| 1.079 | 3-methylcyclopentyl | | |
| 1.080 | [CH(CH₃)-CH₂-C(=O)-O-Et] | | |

TABLE 1-continued

Compounds of formula (I) wherein R₁ is sec-butyl (B1a) or isopropyl (B1b) and R₂ is hydrogen.

| No. | R₃ | Retention time (min.) B1a | B1b |
|---|---|---|---|
| 1.081 | 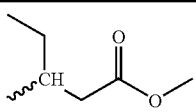 | | |
| 1.082 | 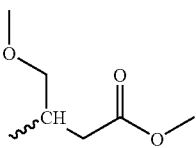 | | |
| 1.083 | (pentafluorophenyl)methyl | | |
| 1.084 | (2,3,5-trichlorophenyl)methyl | | |
| 1.085 | (2,3,6-trichlorophenyl)methyl | | |
| 1.086 | (2,3,4-trifluorophenyl)methyl | 2.60 | 2.48 |
| 1.087 | (2,6-dichlorophenyl)methyl | 2.70 | — |
| 1.088 | (2,3-dichlorophenyl)methyl | 2.70 | — |
| 1.089 | (2-hydroxy-3,5-dichlorophenyl)methyl | | |
| 1.090 | (2-chloro-6-fluorophenyl)methyl | | |
| 1.091 | (2-chloro-6-nitrophenyl)methyl | | |
| 1.092 | (3-chloro-4-nitrophenyl)methyl | | |
| 1.093 | (2-chloro-5-nitrophenyl)methyl | | |
| 1.094 | (2,6-difluorophenyl)methyl | 2.50 | 2.44 |
| 1.095 | (2,3-difluorophenyl)methyl | 2.60 | — |
| 1.096 | (2-hydroxy-5-bromophenyl)methyl | | |
| 1.097 | (2-hydroxy-5-chlorophenyl)methyl | | |
| 1.098 | (3-nitro-4-hydroxyphenyl)methyl | | |
| 1.099 | (3-hydroxy-4-nitro-phenyl)methyl | | |
| 1.100 | (3-hydroxy-phenyl)methyl | | |
| 1.101 | (2-hydroxyphenyl)methyl | | |
| 1.102 | (2,5-dihydroxyphenyl)methyl | | |
| 1.103 | 3-trifruoromethylcyclohexyl | | |
| 1.104 | 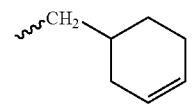 | | |
| 1.105 | 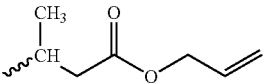 | | |
| 1.106 | 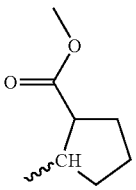 | | |
| 1.107 | 2-methoxycyclohexyl | | |
| 1.108 | 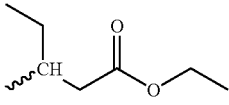 | | |
| 1.109 | 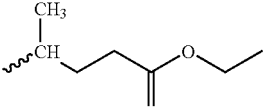 | | |
| 1.110 | 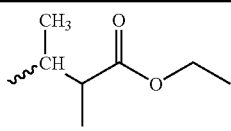 | | |
| 1.111 | 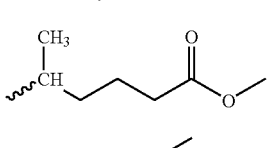 | | |
| 1.112 | 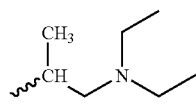 | | |
| 1.113 | (2-trifluoromethylphenyl)methyl | | |
| 1.114 | (3-trifluoromethoxyphenyl)methyl | 2.70 | 2.65 |
| 1.115 | (3-cyanophenyl)methyl | | |
| 1.116 | (2,3-methylenedioxyphenyl)methyl | | |
| 1.117 | (2-methoxy-5-bromo-phenyl)methyl | | |
| 1.118 | (3-bromo-4-hydroxy-5-methoxy-phenyl)methyl | | |
| 1.119 | (2-nitro-3-methoxyphenyl)methyl | | |
| 1.120 | (4-methoxyphenyl)methyl | | |
| 1.121 | (3-hydroxy-4-methoxyphenyl)methyl | | |
| 1.122 | 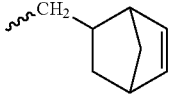 | | |
| 1.123 | 2-ethyl-hexyl | | |
| 1.124 | 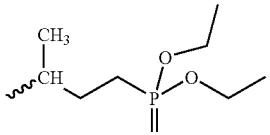 | | |
| 1.125 | (3,5-bis(trifluoromethyl)-phenyl)methyl | | |
| 1.126 | (3-pentafluoroethoxyphenyl)methyl | | |
| 1.127 | 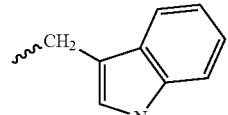 | | |
| 1.128 | 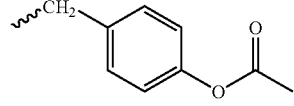 | | |
| 1.129 | (3-bromo-4,6-dimethoxyphenyl)methyl | | |
| 1.130 | (2-bromo-4,5-dimethoxyphenyl)methyl | | |
| 1.131 | 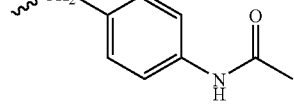 | | |
| 1.132 | (2-nitro-4,5-dimethoxyphenyl)methyl | | |

TABLE 1-continued

Compounds of formula (I) wherein $R_1$ is sec-butyl (B1a) or isopropyl (B1b) and $R_2$ is hydrogen.

| No. | $R_3$ | Retention time (min.) B1a | B1b |
|---|---|---|---|
| 1.133 | 2-benzyloxyethyl | | |
| 1.134 | (3,5-dimethyl-4-hydroxy-phenyl)methyl | | |
| 1.135 | (2-hydroxy-4,6-dimethoxyphenyl)methyl | | |
| 1.136 | (structure) | | |
| 1.137 | (structure) | | |
| 1.138 | (structure) | | |
| 1.139 | (structure) | | |
| 1.140 | (2,4,6-trimethylphenyl)methyl | | |
| 1.141 | 3,7-dimethyloct-6-en-1-yl | | |
| 1.142 | naphth-1-yl | | |
| 1.143 | naphth-2-yl | | |
| 1.144 | (structure) | | |
| 1.145 | (structure) | | |
| 1.146 | (structure) | | |
| 1.147 | (structure) | | |
| 1.148 | (structure) | | |
| 1.149 | (structure) | | |
| 1.150 | (structure) | | |
| 1.151 | n-dodecyl | | |
| 1.152 | (3-[3,4-dichlorophenoxy]-phenyl)methyl | | |
| 1.153 | (3-[4-chlorophenoxy]-phenyl)methyl | | |
| 1.154 | (structure) | | |
| 1.155 | (structure) | | |
| 1.156 | (structure) | | |
| 1.157 | (structure) | | |

TABLE 1-continued

Compounds of formula (I) wherein $R_1$ is sec-butyl (B1a) or isopropyl (B1b) and $R_2$ is hydrogen.

| No. | $R_3$ | Retention time (min.) B1a | B1b |
|---|---|---|---|
| 1.158 | (1-pyrenyl-methyl structure) | | |
| 1.159 | 2-thienyl-methyl (CH2-thiophene) | 5.87 | 5.39 |
| 1.160 | allyl | | |
| 1.161 | 2-hydroxyethyl | | |
| 1.162 | 2-methyl-n-propyl | 2.40 | 2.28 |
| 1.163 | n-pentyl | 2.57 | 2.40 |
| 1.164 | n-hexyl | 2.56 | 2.53 |
| 1.165 | n-heptyl | 2.78 | 2.61 |
| 1.166 | n-octyl | 2.90 | 2.69 |
| 1.167 | n-decyl | 3.11 | 2.94 |
| 1.168 | 2-phenyl-ethyl | 2.60 | 2.40 |
| 1.169 | trimethylsilyl-methyl | 2.69 | 2.40 |
| 1.170 | 4-acetoxy-n-butyl | 2.40 | 2.19 |
| 1.171 | 3,3,3-trifluoro-n-propyl | | |
| 1.172 | 2-buten-1-yl | | |
| 1.173 | 2-methyl-prop-1-en-3-yl | 2.50 | 2.36 |
| 1.174 | 3-methyl-but-2-en-1-yl | | |
| 1.175 | 2-penten-1-yl | | |
| 1.176 | 3-methoxycarbonyl-(E)-2-propen-1-yl | | |
| 1.177 | 3-ethoxycarbonyl-E-2-propen-1-yl | | |
| 1.178 | 2-methoxycarbonyl-1-propen-3-yl | | |
| 1.179 | 2-ethoxycarbonyl-1-propen-3-yl | | |
| 1.180 | 2-bromo-prop-2-en-1-yl | 2.50 | 2.36 |
| 1.181 | 2-tert-butoxycarbonyl-1-propen-3-yl | | |
| 1.182 | (E)-3,7-dimethyl-2,6-octadien-1-yl | 2.90 | 2.82 |
| 1.183 | isobutenyl-oxycarbonyl-methyl | 2.57 | — |
| 1.184 | cyclohexyl-oxycarbonyl-methyl | 2.73 | — |
| 1.185 | benzyl-oxycarbonyl-methyl | | |
| 1.186 | phenoxyethyl-oxycarbonyl-methyl | | |
| 1.187 | p-nitrophenyl-oxycarbonyl-methyl | | |
| 1.188 | (n-butoxycarbonylmethoxy)-carbonyl-methyl | 2.69 | — |
| 1.189 | (o-chlorophenyl)-aminocarbonyl-methyl | 2.60 | — |
| 1.190 | (3,5-dichlorophenyl)-aminocarbonyl-methyl | | |
| 1.191 | (2-trifluoromethyl-4-nitro-phenyl)-aminocarbonyl-methyl | 2.70 | — |
| 1.192 | (4-methylphenyl)-methyl | | |
| 1.193 | (3-methylphenyl)-methyl | | |
| 1.194 | (2-methylphenyl)-methyl | | |
| 1.195 | (2-fluorophenyl)-methyl | | |
| 1.196 | (4-cyanophenyl)-methyl | 2.50 | — |
| 1.197 | (2-cyanophenyl)-methyl | 2.40 | 2.36 |
| 1.198 | (3,5-dimethylphenyl)-methyl | | |
| 1.199 | (3-methoxyphenyl)-methyl | | |
| 1.200 | (3-methyl-2-fluorophenyl)-methyl | | |
| 1.201 | (4-chlorophenyl)-methyl | | |
| 1.202 | (3-chlorophenyl)-methyl | | |
| 1.203 | (2-chlorophenyl)-methyl | | |
| 1.204 | (3,5-difluorophenyl)-methyl | | |
| 1.205 | (2,4-difluorophenyl)-methyl | | |
| 1.206 | (3,4-difluorophenyl)-methyl | | |
| 1.207 | (2,5-difluorophenyl)-methyl | | |
| 1.208 | (4-nitrophenyl)-methyl | | |
| 1.209 | (2-nitrophenyl)-methyl | | |
| 1.210 | 2-naphthyl-methyl | | |
| 1.211 | (3-chloro-2-fluorophenyl)-methyl | 2.70 | 2.53 |
| 1.212 | (2-chloro-4-fluorophenyl)-methyl | | |
| 1.213 | (3,4,5-trifluorophenyl)-methyl | 2.60 | — |
| 1.214 | (2,4,6-trifluorophenyl)-methyl | | |
| 1.215 | (2,4,5-trifluorophenyl)-methyl | 2.60 | 2.48 |
| 1.216 | (2,3,5-trifluorophenyl)-methyl | 2.60 | 2.44 |
| 1.217 | (4-methoxycarbonylphenyl)-methyl | | |
| 1.218 | (3-methoxycarbonylphenyl)-methyl | | |
| 1.219 | (4-difluoromethoxyphenyl)-methyl | | |
| 1.220 | (3-difluoromethoxyphenyl)-methyl | | |
| 1.221 | (2-difluoromethoxyphenyl)-methyl | | |
| 1.222 | (4-trifluoromethylphenyl)-methyl | | |
| 1.223 | (3-trifluoromethylphenyl)-methyl | | |
| 1.224 | (3,4-dichlorophenyl)-methyl | 2.70 | — |
| 1.225 | (2,5-dichlorophenyl)-methyl | 2.70 | — |
| 1.226 | (2-(methoxycarbonylmethyl)-phenyl)-methyl | | |
| 1.227 | (2-methoxy-4-nitrophenyl)-methyl | | |
| 1.228 | biphenyl-4-yl-methyl | 3.60 | — |
| 1.229 | biphenyl-2-yl-methyl | 3.50 | — |
| 1.230 | (4-methylsulphonylphenyl)-methyl | | |
| 1.231 | (4-bromophenyl)-methyl | | |
| 1.232 | (4-trifluoromethoxyphenyl)-methyl | | |
| 1.233 | (2-fluoro-4-trifluoromethylphenyl)-methyl | 2.70 | 2.57 |
| 1.234 | (4-fluoro-2-trifluaromethylphenyl)-methyl | | |
| 1.235 | (4-fluoro-3-trifluoromethylphenyl)-methyl | | |
| 1.236 | (5-fluoro-2-trifluoromethylphenyl)-methyl | 2.70 | 2.57 |
| 1.237 | (2-fluoro-5-trifluoromethylphenyl)-methyl | 2.70 | 2.53 |
| 1.238 | (2-fluoro-3-trifluoromethylphenyl)-methyl | | |
| 1.239 | (3-fluoro-5-trifluoromethylphenyl)-methyl | 2.70 | 2.57 |
| 1.240 | (3-fluoro-4-trifluoromethylphenyl)-methyl | 2.70 | 2.57 |
| 1.241 | (2-methoxy-4-methoxycarbonylphenyl)-methyl | | |
| 1.242 | (2-fluoro-4-bromophenyl)-methyl | | |
| 1.243 | (5-fluoro-2-bromophenyl)-methyl | 2.70 | 2.48 |
| 1.244 | (2,3-dichloro-4-methoxyphenyl)-methyl | | |
| 1.245 | (4-trifluoromethylthio-phenyl)-methyl | | |
| 1.246 | (3-trifluoromethylthio-phenyl)-methyl | | |
| 1.247 | (2-trifluoromethylthio-phenyl)-methyl | | |
| 1.248 | (4-(o-cyanophenyl)-methyl | 3.50 | — |
| 1.249 | (2-chloro-3-trifluoromethylphenyl)-methyl | 2.70 | 2.61 |
| 1.250 | (3,4-difluoro-5-trifluorophenyl)-methyl | 2.70 | — |
| 1.251 | (2-nitro-4,5-dimethoxyphenyl)-methyl | | |
| 1.252 | (4-iodophenyl)-methyl | | |
| 1.253 | (3-iodophenyl)-methyl | | |
| 1.254 | (2-iodophenyl)-methyl | | |
| 1.255 | (2,4-bis(trifluoromethyl)-phenyl)-methyl | | |
| 1.256 | (3,5-dibromophenyl)-methyl | 2.80 | 2.65 |
| 1.257 | 5-bromo-thiophene-2-yl-methyl | | |
| 1.258 | 4-bromo-thiophene-2-yl-methyl | | |
| 1.259 | 10-undecen-1-yl | | |
| 1.260 | (4-isobutylphenyl)-methyl | | |
| 1.261 | (2-isopropylthiophenyl)-methyl | | |
| 1.262 | (4-isopropylphenyl)-methyl | | |
| 1.262 | (3-isopropylphenyl)-methyl | | |
| 1.263 | 2-ethyl-n-butyl | | |
| 1.264 | n-nonyl | | |
| 1.265 | n-undecyl | | |
| 1.266 | isopentyl | | |
| 1.267 | (4-ethylphenyl)-methyl | | |
| 1.268 | (1-methylthio-1-cyclopropyl)-methyl | | |
| 1.269 | 3-methylthio-n-propyl | | |
| 1.270 | (4-methylthiophenyl)-methyl | | |
| 1.271 | (2,5-dimethylphenyl)-methyl | | |
| 1.272 | (3-fluoro-4-methylphenyl)-methyl | | |
| 1.273 | (5-methyl-thien-2-yl) | | |
| 1.274 | (3-methyl-thien-2-yl) | | |
| 1.275 | (4-methylphenyl)-ethyl | | |
| 1.276 | (3,5-dichlorophenyl)-methyl | | |
| 1.277 | (2,4-dichlorophenyl)-methyl | | |
| 1.278 | 1-methyl-1H-pyrrole-2-yl-methyl | | |
| 1.279 | (3-fluoro-4-chlorophenyl)-methyl | | |
| 1.280 | (4-fluorophenyl)-methyl | | |
| 1.281 | 4-fluorophenylthio)-3-n-propyl | | |
| 1.281 | cyclopropyl-methyl | | |
| 1.282 | cyclohexyl-methyl | | |
| 1.283 | cyclohexyl-3-n-propyl | | |
| 1.284 | 2-pyridyl-methyl | | |

TABLE 1-continued

Compounds of formula (I) wherein $R_1$ is sec-butyl (B1a) or isopropyl (B1b) and $R_2$ is hydrogen.

| No. | $R_3$ | Retention time (min.) B1a | B1b |
|---|---|---|---|
| 1.285 | 3-furyl-methyl | | |
| 1.286 | 3-thienyl-methyl | | |
| 1.287 | 2-thiazolyl-methyl | | |
| 1.288 | neopentyl | | |
| 1.289 | isohexyl | | |
| 1.290 | tert-butyl | | |
| 1.291 | 3-hydroxypropyl | | |

TABLE 2

Compounds of formula (I) wherein $R_1$ is sec-butyl (B1a) or isopropyl (B1b) and $R_2$ is methyl:

| No. | $R_3$ | Retention time (min.) B1a | B1b |
|---|---|---|---|
| 2.001 | benzyl | | |
| 2.002 | allyl | | |
| 2.003 | —CH$_2$—C(=O)—O-ethyl | | |
| 2.004 | 2-hydroxyethyl | | |
| 2.005 | —CH$_2$—C(=O)—O-methyl | | |
| 2.006 | but-2-en-1-yl | | |
| 2.007 | [structure: ~CH$_2$—C(=O)—O—benzyl] | | |
| 2.008 | —CH$_2$—C(=O)—O-tert-butyl | | |
| 2.009 | (4-fluoro-2-trifluoromethylphenyl)methyl | | |
| 2.010 | (4-fluoro-3-trifluoromethylphenyl)methyl | | |
| 2.011 | (3,4-difluorophenyl)methyl | | |
| 2.012 | isopropyl | | |
| 2.013 | (3-trifluoromethylphenyl)methyl | | |
| 2.014 | [structure: ~CH$_2$—CH=CH—C(=O)—O-ethyl] | | |
| 2.015 | 2-methylallyl | | |
| 2.016 | —CH$_2$—C(=O)—OH | | |
| 2.017 | —CH$_2$—C(=O)—NH$_2$ | | |
| 2.018 | [structure: ~CH$_2$—C(=O)—O—CH$_2$—(4-nitrophenyl)] | | |
| 2.019 | (2-methylphenyl)methyl | | |
| 2.020 | [structure: ~CH$_2$—C(=CH$_2$)—C(=O)—O-ethyl] | | |
| 2.021 | [structure: ~CH$_2$—C(=O)—(3-bromophenyl)] | | |
| 2.022 | ethyl | | |
| 2.023 | [structure: ~CH$_2$—C(=O)—NH—CH$_2$—C(=O)—O—benzyl] | | |
| 2.024 | [structure: ~CH$_2$—C(=O)—NH—CH(CH$_3$)—C(=O)—O—benzyl] | | |
| 2.025 | [structure: ~CH$_2$—C(CH$_3$)$_2$—OH] | | |
| 2.026 | (4-phenylphenyl)methyl | | |
| 2.027 | [structure: ~CH$_2$—CH=CH—C≡C—C(CH$_3$)$_3$ (cis)] | | |
| 2.028 | [structure: ~CH$_2$—CH=CH—C≡C—C(CH$_3$)$_3$ (trans)] | | |
| 2.029 | (4-tert-butylphenyl)methyl | | |
| 2.030 | (4-fluorophenyl)methyl | | |
| 2.031 | (4-bromophenyl)methyl | | |
| 2.032 | 2-bromoallyl | | |
| 2.033 | —CH$_2$—C(=O)—O-isopropyl | | |
| 2.034 | —CH$_2$—C(=O)—O—CH$_2$—CH$_2$—O—CH$_3$ | | |
| 2.035 | (2,3,4-trifluorophenyl)methyl | | |
| 2.036 | (2,4,5-trifluorophenyl)methyl | | |
| 2.037 | (2,3,6-trifluorophenyl)methyl | | |
| 2.038 | (3,5-dibromophenyl)methyl | | |
| 2.039 | (3-fluoro-6-bromophenyl)methyl | | |
| 2.040 | (2,3-dichlorophenyl)methyl | | |
| 2.041 | (2,6-dichlorophenyl)methyl | | |
| 2.042 | (2,5-dichlorophenyl)methyl | | |
| 2.043 | (3,4-dichlorophenyl)methyl | | |
| 2.044 | (2-fluoro-3-chloro-phenyl)methyl | | |
| 2.045 | (2-chloro-4-fluoro-phenyl)methyl | | |
| 2.046 | (2,5-difluorophenyl)methyl | | |
| 2.047 | (2,6-difluorophenyl)methyl | | |
| 2.048 | (2,3-difluorophenyl)methyl | | |
| 2.049 | (3,5-difluorophenyl)methyl | | |

TABLE 2-continued

Compounds of formula (I) wherein $R_1$ is sec-butyl (B1a) or isopropyl (B1b) and $R_2$ is methyl:

| No. | $R_3$ | Retention time (min.) B1a | B1b |
|---|---|---|---|
| 2.050 | (2-bromophenyl)methyl | | |
| 2.051 | (2-chlorophenyl)methyl | | |
| 2.052 | (2-fluorophenyl)methyl | | |
| 2.053 | (3-fluorophenyl)methyl | | |
| 2.054 | (4-iodophenyl)methyl | | |
| 2.055 | (2-iodophenyl)methyl | | |
| 2.056 | (4-nitrophenyl)methyl | | |
| 2.057 | (3-nitrophenyl)methyl | | |
| 2.058 | (3-trifluoromethyl-6-chlorophenyl)methyl | | |
| 2.059 | (3-trifluoromethyl-5-fluorophenyl)methyl | | |
| 2.060 | (3,5-dichlorophenyl)methyl | | |
| 2.061 | (2-trifluoromethylphenyl)methyl | | |
| 2.062 | (3-trifluoromethoxyphenyl)methyl | | |
| 2.063 | (4-cyanophenyl)methyl | | |
| 2.064 | (2-cyanophenyl)methyl | | |
| 2.065 | (3-cyanophenyl)methyl | | |
| 2.066 | (2,3-dichloro-4-methoxy-phenyl)methyl | | |
| 2.067 | [structure: CH2-NH-C(=O)-(2-chlorophenyl)] | | |
| 2.068 | (4-difluoromethoxyphenyl)methyl | | |
| 2.069 | (2-fluoro-3-methylphenyl)methyl | | |
| 2.070 | [structure: CH2-C(OEt)=CH-C(=O)OEt] | | |
| 2.071 | (3,5-bis(trifluoromethyl)-phenyl)methyl | | |
| 2.072 | (2,4-bis(trifluoromethyl)-phenyl)methyl | | |
| 2.073 | [structure: CH2-(4-methoxycarbonylphenyl)] | | |
| 2.074 | [structure: CH2-(3-methoxycarbonylphenyl)] | | |
| 2.075 | (3,5-dimethylphenyl)methyl | | |
| 2.076 | (2-methoxy-4-methoxycarbonyl-phenyl)methyl | | |
| 2.077 | [structure: CH2-naphthalen-2-yl] | | |
| 2.078 | [structure: CH2-CH=CH-C(=O)-O-CH2-C(=O)-phenyl] | | |
| 2.079 | (2-phenylphenyl)methyl | | |
| 2.080 | (4-phenylphenyl)methyl | | |
| 2.081 | [structure: CH2-(2'-cyanobiphenyl-4-yl)] | | |
| 2.082 | n-propyl | | |
| 2.083 | isopropyl | | |
| 2.084 | n-butyl | | |
| 2.085 | n-pentyl | | |
| 2.086 | n-hexyl | | |
| 2.087 | n-heptyl | | |
| 2.088 | n-octyl | | |
| 2.089 | isobutyl | | |
| 2.090 | sec.-butyl | | |
| 2.091 | tert.-butyl | | |
| 2.092 | isopentyl | | |
| 2.093 | neopentyl | | |
| 2.094 | isohexyl | | |
| 2.095 | [structure: CH2-C(=O)-NH-CH(CH3)-COOH (alanine derivative)] | | |
| 2.096 | (4-methylphenyl)-methyl | | |
| 2.097 | (3-methylphenyl)-methyl | | |
| 2.098 | (3-methoxyphenyl)-methyl | | |
| 2.099 | (4-chlorophenyl)-methyl | | |
| 2.100 | (3-chlorophenyl)-methyl | | |
| 2.101 | (2,4-difluorophenyl)-methyl | | |
| 2.102 | (2-nitrophenyl)-methyl | | |
| 2.103 | (3,4,5-trifluorophenyl)-methyl | | |
| 2.104 | (2,4,6-trifluorophenyl)-methyl | | |
| 2.105 | (2,3,5-trifluorophenyl)-methyl | | |
| 2.106 | 2-penten-1-yl | | |
| 2.107 | 3,3-dimethyl-allyl | | |
| 2.108 | (3-difluoromethoxyphenyl)-methyl | | |
| 2.109 | (2-difluoromethoxyphenyl)-methyl | | |
| 2.110 | (4-trifluoromethylphenyl)-methyl | | |
| 2.111 | (3-methoxycarbonylmethylphenyl)-methyl | | |
| 2.112 | (4-methylsulphonylphenyl)-methyl | | |
| 2.113 | (3-bromophenyl)-methyl | | |
| 2.114 | (4-trifluoromethoxyphenyl)-methyl | | |
| 2.115 | (2-fluoro-4-trifluoromethylphenyl)-methyl | | |
| 2.116 | (5-fluoro-2-trifluoromethylphenyl)-methyl | | |
| 2.117 | (2-fluoro-5-trifluoromethylphenyl)-methyl | | |
| 2.118 | (2-fluoro-3-trifluoromethylphenyl)-methyl | | |
| 2.119 | (3-fluoro-4-trifluoromethylphenyl)-methyl | | |
| 2.120 | (2,3,6-trichlorophenyl)-methyl | | |
| 2.121 | pentafluorophenyl-methyl | | |
| 2.122 | (4-bromo-2-fluorophenyl)-methyl | | |
| 2.123 | (3-trifluoromethylthiophenyl)-methyl | | |
| 2.124 | (4-trifluoromethylthiophenyl)-methyl | | |
| 2.125 | (2-trifluoromethylthiophenyl)-methyl | | |
| 2.126 | (3,4-difluoro-5-trifluoromethylphenyl)-methyl | | |
| 2.127 | (3-iodophenyl)-methyl | | |
| 2.128 | (5-bromo-thien-2-yl)-methyl | | |
| 2.129 | (4-bromo-thien-2-yl)-methyl | | |
| 2.130 | 10-undecen-1-yl | | |
| 2.131 | (4-isobutylphenyl)-methyl | | |

TABLE 2-continued

Compounds of formula (I) wherein $R_1$ is sec-butyl (B1a) or isopropyl (B1b) and $R_2$ is methyl:

| No. | $R_3$ | Retention time (min.) B1a | B1b |
|---|---|---|---|
| 2.132 | (2-isopropylthiophenyl)-methyl | | |
| 2.133 | (4-isopropylphenyl)-methyl | | |
| 2.134 | (3-isopropylphenyl)-methyl | | |
| 2.135 | 2-ethyl-n-butyl | | |
| 2.136 | 4-decen-1-yl | | |
| 2.137 | n-nonyl | | |
| 2.138 | n-decyl | | |
| 2.139 | n-undecyl | | |
| 2.140 | n-dodecyl | | |
| 2.141 | (4-ethylphenyl)-methyl | | |
| 2.142 | 3-methylthio-n-propyl | | |
| 2.143 | ([4-methylthio]phenyl)-methyl | | |
| 2.144 | (2,4,6-trimethylphenyl)-methyl | | |
| 2.145 | (2,5-dimethylphenyl)-methyl | | |
| 2.146 | (2,4-dimethylphenyl)-methyl | | |
| 2.147 | (3-fluoro-4-methylphenyl)-methyl | | |
| 2.148 | (5-methyl-furan-2-yl)-methyl | | |
| 2.149 | (5-methyl-thien-2-yl)-methyl | | |
| 2.150 | (4-methylphenyl)-3-ethyl | | |
| 2.151 | (3-methyl-thien-2-yl)-methyl | | |
| 2.152 | (2,3,5-trichlorophenyl)-methyl | | |
| 2.153 | (2,3,6-trichlorophenyl)-methyl | | |
| 2.154 | (2,4-dichlorophenyl)-methyl | | |
| 2.155 | (3-fluoro-4-chlorophenyl)-methyl | | |
| 2.156 | (3,4-difluorophenyl)-methyl | | |
| 2.157 | Cyclopropylmethyl | | |
| 2.158 | cyclohex-3-en-1-yl-methyl | | |
| 2.159 | cyclohexyl-methyl | | |
| 2.160 | cyclohexyl-n-propyl | | |
| 2.161 | phenyl-3-n-propyl | | |
| 2.162 | phenyl-2-ethyl | | |
| 2.163 | 2-pyridyl-methyl | | |
| 2.164 | 3-pyridyl-methyl | | |
| 2.165 | 2-furyl-methyl | | |
| 2.166 | 3-furyl-methyl | | |
| 2.167 | 4-pyridyl-methyl | | |
| 2.168 | 3-thienyl-methyl | | |
| 2.169 | 2-thiazolyl-methyl | | |
| 2.170 | isobutenyl-oxycarbonyl-methyl | | |
| 2.171 | cyclohexyl-oxycarbonyl-methyl | | |
| 2.172 | n-butoxycarbonyl-methoxycarbonyl-methyl | | |
| 2.173 | phenoxyethyl-oxycarbonyl-methyl | | |
| 2.174 | p-nitrophenyl-oxycarbonyl-methyl | | |
| 2.175 | 3-phenyl-allyl | | |
| 2.176 | 3,5-dichlorophenyl-aminocarbonyl-methyl | | |
| 2.177 | 2-(tert-butoxycarbonyl)-allyl | | |
| 2.178 | 4-acetoxy-n-butyl | | |
| 2.179 | 2-trifluoromethyl-ethyl | | |
| 2.180 | trimethylsilyl-methyl | | |
| 2.181 | 3,7-dimethyloct-6-en-1-yl | | |
| 2.182 | 3-hydroxypropyl | | |

TABLE 3

Compounds of formula (I) wherein $R_1$ is sec-butyl (B1a) or isopropyl (B1b):

| No. | $R_2$ | $R_3$ | Retention time (min.) B1a | B1b |
|---|---|---|---|---|
| 3.001 | 3-phenylallyl | 3-phenylallyl | | |
| 3.002 | 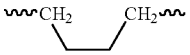 | | | |
| 3003 | 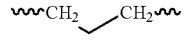 | | | |
| 3.004 | 3-phenyl-n-propyl | 3-phenyl-n-propyl | | |
| 3.005 | 3,7-dimethyloct-6-en-1-yl | 3,7-dimethyloct-6-en-1-yl | | |
| 3.006 | ethyl | 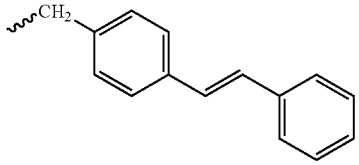 | | |
| 3.007 | ethyl | ethyl | | |
| 3.008 | 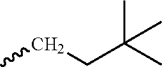 | 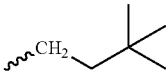 | | |
| 3.009 | 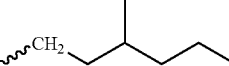 | 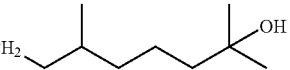 | | |

TABLE 3-continued

Compounds of formula (I) wherein R₁ is sec-butyl (B1a) or isopropyl (B1b):

| No. | R₂ | R₃ | Retention time (min.) B1a | B1b |
|---|---|---|---|---|
| 3.010 | 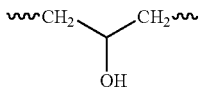 | | | |
| 3.011 | 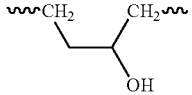 | | | |
| 3.012 | 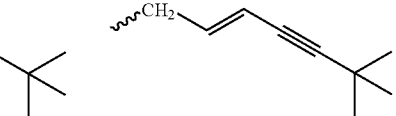 | 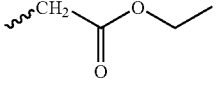 | | |
| 3.013 | ethyl | benzyl | | |
| 3.014 | ethyl | allyl | | |
| 3.015 | ethyl | 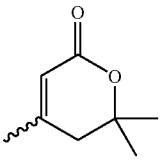 | | |
| 3.016 | 3-methyl-n-butyl | 3-methyl-n-butyl | | |
| 3.017 | 3-phenyl-n-butyl | 3-phenyl-n-butyl | | |
| 3.018 | ethyl | n-propyl | | |
| 3.019 | ethyl | isopropyl | | |
| 3.020 | ethyl | n-butyl | | |
| 3.021 | ethyl | pentyl | | |
| 3.022 | ethyl | hexyl | | |
| 3.023 | ethyl | heptyl | | |
| 3.024 | ethyl | n-octyl | | |
| 3.025 | ethyl | sec-butyl | | |
| 3.026 | ethyl | tert-butyl | | |
| 3.027 | ethyl | isopentyl | | |
| 3.028 | ethyl | neopentyl | | |
| 3.029 | ethyl | isohexyl | | |

TABLE 4

Compounds of formula (I) wherein R₁ is sec-butyl (B1a) or isopropyl (B1b) and R₂ is hydrogen:

| No. | R3 | Retention time (min.) B1a | B1b |
|---|---|---|---|
| 4.001 | 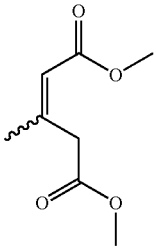 | | |
| 4.002 | | | |

TABLE 4-continued

Compounds of formula (I) wherein $R_1$ is sec-butyl (B1a) or isopropyl (B1b) and $R_2$ is hydrogen:

| No. | R3 | Retention time (min.) B1a | B1b |
|---|---|---|---|
| 4.003 | | | |
| 4.004 | | | |
| 4.005 | | | |
| 4.006 | | | |
| 4.007 | | | |
| 4.008 | | | |
| 4.009 | | | |
| 4.010 | | | |
| 4.011 | | | |
| 4.012 | | | |
| 4.013 | | | |
| 4.014 | | | |
| 4.015 | | | |
| 4.016 | | | |
| 4.017 | | | |
| 4.018 | | | |
| 4.019 | | | |
| 4.020 | | | |
| 4.021 | | | |
| 4.022 | | | |
| 4.023 | | | |
| 4.024 | | | |
| 4.025 | | | |

TABLE 4-continued

Compounds of formula (I) wherein $R_1$ is sec-butyl (B1a) or isopropyl (B1b) and $R_2$ is hydrogen:

| No. | R3 | Retention time (min.) B1a | B1b |
|---|---|---|---|
| 4.026 | [2-(thiomorpholin-4-yl)ethyl] | | |
| 4.027 | [2-(4-methylpiperazin-1-yl)ethyl] | | |
| 4.028 | [2-(4-phenylpiperazin-1-yl)ethyl] | | |
| 4.029 | [2-(4-(ethoxycarbonylmethyl)piperazin-1-yl)ethyl] | | |
| 4.030 | [2-(4-(2-hydroxyethyl)piperazin-1-yl)ethyl] | | |
| 4.031 | [2-(4-(2-hydroxy-2-methylpropyl)piperazin-1-yl)ethyl] | | |
| 4.032 | [4-(1,3-dioxoisoindolin-2-yl)butyl] | | |
| 4.033 | [2-(2-(1,3-dioxoisoindolin-2-yl)ethoxy)ethyl] | | |

TABLE 5

Compounds of formula (I) wherein $R_1$ is sec-butyl (B1a) or isopropyl (B1b) and $R_2$ is methyl

| No. | R3 | Retention time (min.) B1a | B1b |
|---|---|---|---|
| 5.001 | trifluoromethyl | | |
| 5.002 | [dibenzyl N-acyl-D-glutamate] | | |
| 5.003 | 3,3-dichloroallyl | | |
| 5.004 | 2-chloroallyl | | |
| 5.005 | [benzyl N-acyl-O-benzyl-L-tyrosinate] | | |

TABLE 5-continued

Compounds of formula (I) wherein $R_1$ is sec-butyl (B1a) or isopropyl (B1b) and $R_2$ is methyl

| No. | $R_3$ | Retention time (min.) B1a | B1b |
|---|---|---|---|
| 5.006 | benzyl ester of N-acyl phenylalanine | | |
| 5.007 | 3-iodopropyl | | |
| 5.008 | cyclobutyl | | |
| 5.009 | -CH2CH2CH2-N(CH3)2 | | |
| 5.010 | -CH2CH2CH2-NH2 | | |
| 5.011 | -CH2CH2CH2-NHCH3 | | |
| 5.012 | -CH2CH2CH2-O-C(O)CH3 | | |
| 5.013 | -CH(CH2CH3)2 | | |
| 5.014 | -CH2-CH=CH-CH2Cl | | |
| 5.015 | -CH2-CH=CH-CH2-N(CH3)2 | | |
| 5.016 | -CH2CH2-C(O)-O-CH2CH3 | | |
| 5.017 | -CH2CH2-C≡N | | |
| 5.018 | -CH2CH2CH2-O-C(O)-CH(OH)CH3 | | |
| 5.019 | -CH2CH2-C(O)-O-C(CH3)3 | | |
| 5.020 | -CH2-C≡C-CH2Cl | | |

TABLE 5-continued

Compounds of formula (I) wherein $R_1$ is sec-butyl (B1a) or isopropyl (B1b) and $R_2$ is methyl

| No. | $R_3$ | Retention time (min.) B1a | B1b |
|---|---|---|---|
| 5.021 | –CH₂C≡N | | |
| 5.022 | –CH₂C(CH₃)₂OH | | |
| 5.023 | –CH₂CH₂CH₂OC(O)H | | |
| 5.024 | –CH₂CH₂CH₂OC(O)CH=CH₂ | | |
| 5.025 | –CH₂CH₂CH₂OC(O)(CH₂)₆CH₃ | | |
| 5.026 | –CH₂CH₂CH₂OC(O)CH₂CH₂CH₂OH | | |
| 5.027 | –CH₂CH₂CH₂OC(O)CH₂C(O)OCH₃ | | |
| 5.028 | –CH₂CH₂CH₂OC(O)C₆H₅ | | |
| 5.029 | –CH₂CH₂CH₂OC(O)-(2,5-diCl-C₆H₃) | | |
| 5.030 | –CH₂CH₂CH₂OC(O)CH₂CH₃ | | |
| 5.031 | –CH₂CH₂CH₂OC(O)CH(OH)CH₃ (R) | | |
| 5.032 | –CH₂CH₂CH₂OC(O)CH₂C(O)OCH₂CH₃ | | |

TABLE 5-continued

Compounds of formula (I) wherein R₁ is sec-butyl (B1a) or isopropyl (B1b) and R₂ is methyl

| No. | R₃ | Retention time (min.) B1a | B1b |
|---|---|---|---|
| 5.033 | | | |
| 5.034 | | | |
| 5.035 | | | |
| 5.036 | | | |
| 5.037 | | | |
| 5.038 | | | |
| 5.039 | | | |
| 5.040 | | | |
| 5.041 | | | |
| 5.042 | | | |
| 5.043 | | | |
| 5.044 | | | |

TABLE 5-continued
Compounds of formula (I) wherein R₁ is sec-butyl (B1a) or isopropyl (B1b) and R₂ is methyl
| No. | R₃ | Retention time (min.) B1a | B1b |
|---|---|---|---|
| 5.045 | 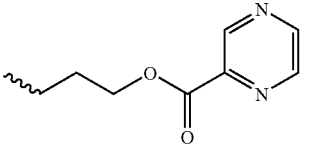 | | |
| 5.046 | 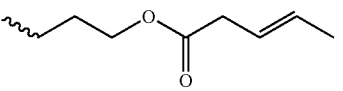 | | |
| 5.047 | 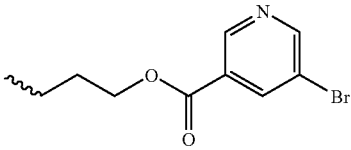 | | |
| 5.048 | 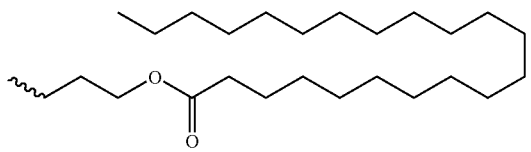 | | |
| 5.049 | 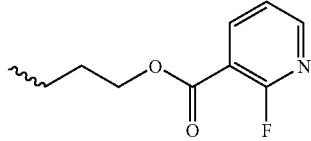 | | |
| 5.050 | 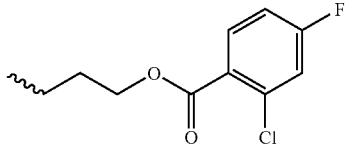 | | |
| 5.051 | 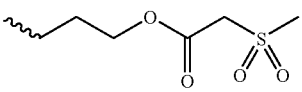 | | |
| 5.052 | 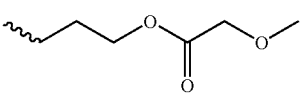 | | |
| 5.053 | 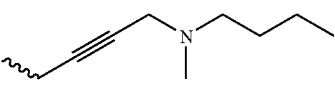 | | |
| 5.054 | 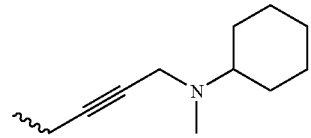 | | |
| 5.055 | 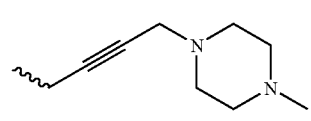 | | |

TABLE 5-continued

Compounds of formula (I) wherein R₁ is sec-butyl (B1a) or isopropyl (B1b) and R₂ is methyl

| No. | R₃ | Retention time (min.) B1a | B1b |
|---|---|---|---|
| 5.056 | | | |
| 5.057 | | | |
| 5.058 | | | |
| 5.059 | | | |
| 5.060 | | | |
| 5.061 | | | |
| 5.062 | | | |
| 5.063 | | | |
| 5.064 | | | |
| 5.065 | | | |
| 5.066 | | | |

TABLE 5-continued
Compounds of formula (I) wherein R₁ is sec-butyl
(B1a) or isopropyl (B1b) and R₂ is methyl
| No. | R₃ | Retention time (min.) B1a | B1b |
|---|---|---|---|
| 5.067 | 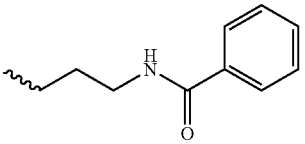 | | |
| 5.068 | 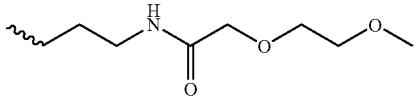 | | |
| 5.069 | 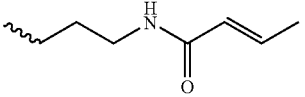 | | |
| 5.070 | 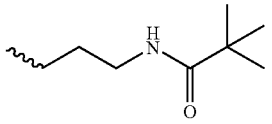 | | |
| 5.071 | 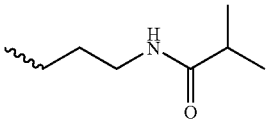 | | |
| 5.072 | 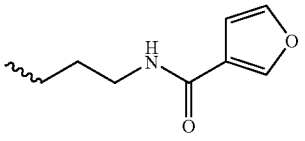 | | |
| 5.073 | 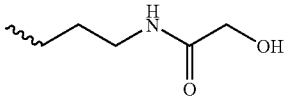 | | |
| 5.074 | 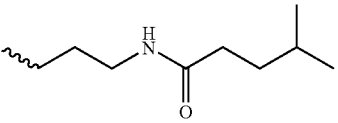 | | |
| 5.075 | 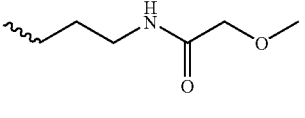 | | |
| 5.076 | 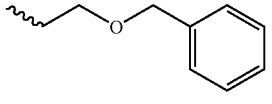 | | |
| 5.077 | 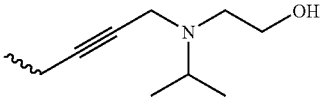 | | |

TABLE 5-continued
Compounds of formula (I) wherein R₁ is sec-butyl
(B1a) or isopropyl (B1b) and R₂ is methyl
| | | Retention time (min.) | |
|---|---|---|---|
| No. | R₃ | B1a | B1b |
| 5.078 | 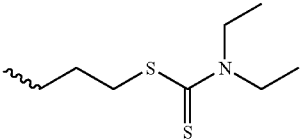 | | |
| 5.079 | 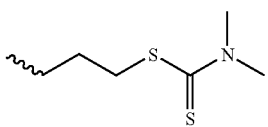 | | |
| 5.080 | 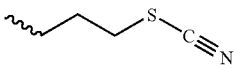 | | |
| 5.081 | 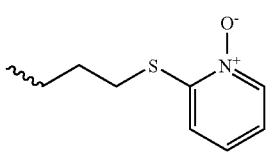 | | |
| 5.082 | 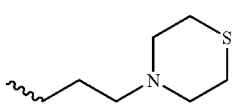 | | |
| 5.083 | 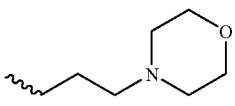 | | |
| 5.084 | 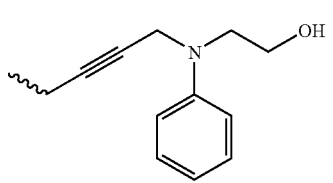 | | |
| 5.085 | 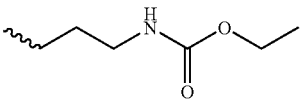 | | |
| 5.086 | 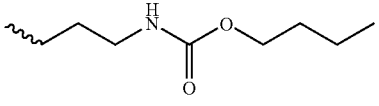 | | |
| 5.087 | 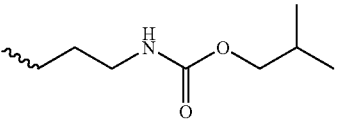 | | |
| 5.088 | 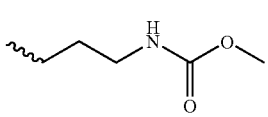 | | |

TABLE 5-continued
Compounds of formula (I) wherein R₁ is sec-butyl
(B1a) or isopropyl (B1b) and R₂ is methyl
| No. | R₃ | Retention time (min.) B1a | B1b |
|---|---|---|---|
| 5.089 | 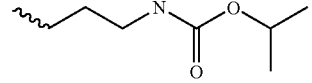 | | |
| 5.090 | 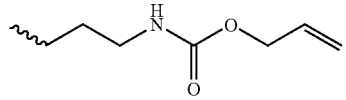 | | |
| 5.091 | 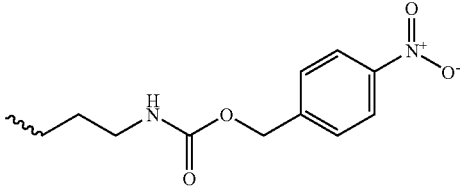 | | |
| 5.092 | 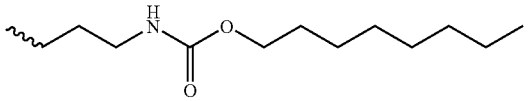 | | |
| 5.093 | 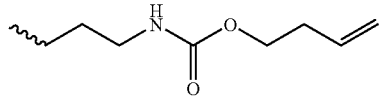 | | |
| 5.094 | 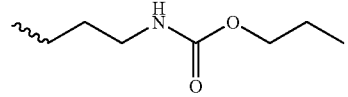 | | |
| 5.095 | 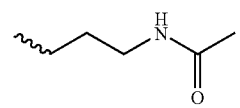 | | |
| 5.096 | 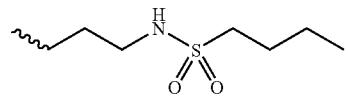 | | |
| 5.097 | 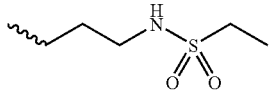 | | |
| 5.098 | 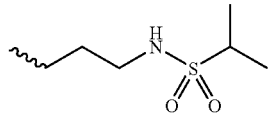 | | |
| 5.099 | 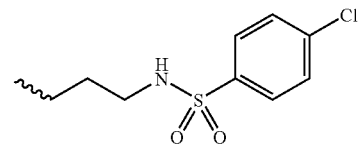 | | |

TABLE 5-continued

Compounds of formula (I) wherein $R_1$ is sec-butyl (B1a) or isopropyl (B1b) and $R_2$ is methyl

| No. | $R_3$ | Retention time (min.) B1a | B1b |
|---|---|---|---|
| 5.100 | ~~~CH2CH2CH2-NH-SO2-CH2-C6H5 | | |
| 5.101 | ~~~CH2CH2CH2-NH-SO2-C6H4-4-F | | |
| 5.102 | ~~~CH2CH2CH2-NH-SO2-C6H4-4-OCH3 | | |
| 5.103 | ~~~CH2CH2CH2-NH-SO2-C6H4-4-CH3 | | |
| 5.104 | ~~~CH2CH2CH2-NH-SO2-C6H4-2-Cl | | |
| 5.105 | ~~~CH2CH2-phthalimide | | |
| 5.106 | ~~~CH2CH2-NH2 | | |
| 5.108 | ~~~CH2CH2-N(CH3)2 | | |
| 5.109 | ~~~CH2CH2-pyrrolidinyl | | |
| 5.110 | ~~~CH2CH2-piperidinyl | | |
| 5.111 | ~~~CH2CH2-morpholinyl | | |

TABLE 5-continued
Compounds of formula (I) wherein R₁ is sec-butyl (B1a) or isopropyl (B1b) and R₂ is methyl
| No. | R₃ | Retention time (min.) B1a | B1b |
|---|---|---|---|
| 5.112 | 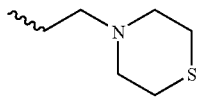 | | |
| 5.113 | 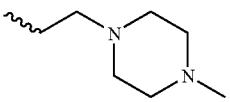 | | |
| 5.114 | 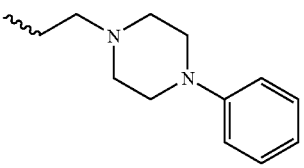 | | |
| 5.115 | 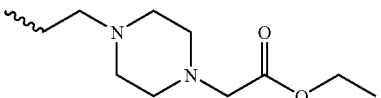 | | |
| 5.116 | 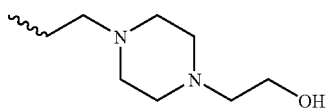 | | |
| 5.117 | 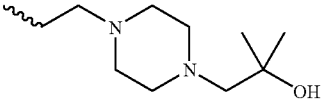 | | |
| 5.118 | 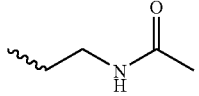 | | |
| 5.119 | 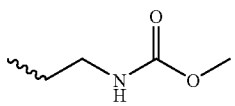 | | |
| 5.120 | 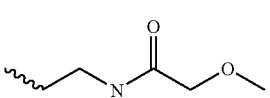 | | |
| 5.121 | 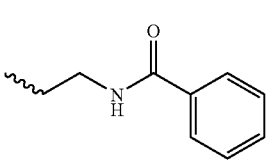 | | |
| 5.122 | 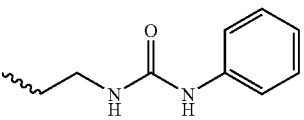 | | |

TABLE 5-continued

Compounds of formula (I) wherein $R_1$ is sec-butyl (B1a) or isopropyl (B1b) and $R_2$ is methyl

| No. | $R_3$ | Retention time (min.) B1a | B1b |
|---|---|---|---|
| 5.123 | ~NH-S(O)₂-Et | | |
| 5.124 | ~NH-S(O)₂-Ph | | |
| 5.125 | ~(CH₂)₄-NH₂ | | |
| 5.126 | ~(CH₂)₄-N(CH₃)₂ | | |
| 5.127 | ~(CH₂)₄-NH-C(O)CH₃ | | |
| 5.128 | ~(CH₂)₄-NH-C(O)OCH₃ | | |
| 5.129 | ~CH₂-O-CH₂CH₂-NH₂ | | |
| 5.130 | ~CH₂-O-CH₂CH₂-N(CH₃)₂ | | |
| 5.131 | ~CH₂-O-CH₂CH₂-NH-C(O)CH₃ | | |
| 5.132 | ~CH₂-O-CH₂CH₂-NH-C(O)OCH₃ | | |
| 5.133 | ~(CH₂)₄-phthalimide | | |
| 5.134 | ~CH₂-O-CH₂CH₂-phthalimide | | |

TABLE 5-continued

Compounds of formula (I) wherein R₁ is sec-butyl
(B1a) or isopropyl (B1b) and R₂ is methyl

| No. | R₃ | Retention time (min.) B1a | B1b |
|---|---|---|---|
| 5.135 | 3-methylphenyl urea | | |
| 5.136 | 4-chlorophenyl urea | | |
| 5.137 | 3,4-dichlorophenyl urea | | |
| 5.138 | phenyl urea | | |
| 5.139 | 1-naphthyl urea | | |
| 5.140 | n-butyl urea | | |
| 5.141 | 4-methoxyphenyl urea | | |
| 5.142 | cyclohexyl urea | | |
| 5.143 | n-propyl urea | | |
| 5.144 | 3-(trifluoromethyl)phenyl urea | | |

TABLE 5-continued

Compounds of formula (I) wherein $R_1$ is sec-butyl
(B1a) or isopropyl (B1b) and $R_2$ is methyl

| No. | $R_3$ | Retention time (min.) B1a | B1b |
|---|---|---|---|
| 5.145 | 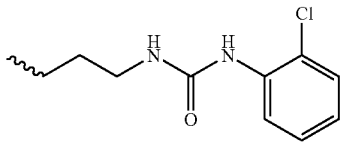 | | |
| 5.146 | 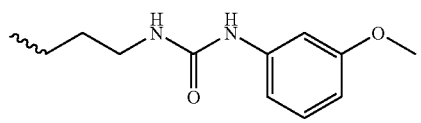 | | |

TABLE 6

Compounds of formula (1) wherein $R_1$ is
sec-butyl (B1a) or isopropyl (B1b)

| No. | $R_2$ | $R_3$ | Retention time (min.) B1a | B1b |
|---|---|---|---|---|
| 6.001 | ·····CH₂ | ·····CH₂  | 6.13 | 5.71 |
| 6.002 | ·····CH₂ | CH₂····· 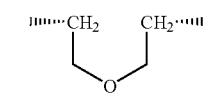 | | |
| 6.003 | ·····CH₂ | CH₂····· 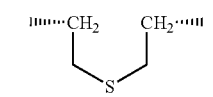 | | |
| 6.004 | ·····CH₂ | CH₂····· 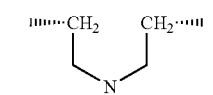 | | |
| 6.005 | ·····CH₂ | CH₂····· 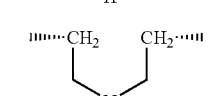 | | |
| 6.007 | ·····CH₂ | CH₂····· 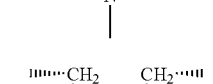 | | |
| 6.008 | ·····CH₂ | CH₂····· 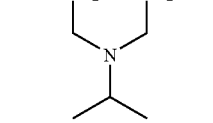 | | |
| 6.009 | ·····CH₂ | CH₂····· 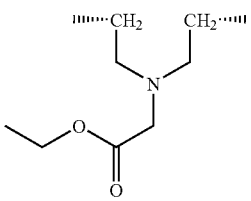 | | |
| 6.010 | ·····CH₂ | CH₂····· 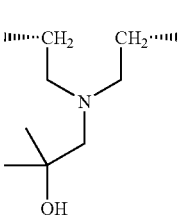 | | |
| 6.011 | ·····CH₂ | CH₂····· 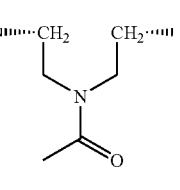 | | |
| 6.012 | ·····CH₂ | CH₂····· 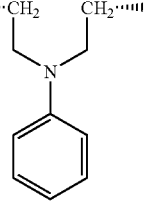 | | |

TABLE 6-continued

Compounds of formula (1) wherein $R_1$ is sec-butyl (B1a) or isopropyl (B1b)

| No. | $R_2$ | $R_3$ | Retention time (min.) B1a | B1b |
|---|---|---|---|---|
| 6.013 | ⅲ····CH$_2$–N(–CH$_2$····ⅲ)(–C$_6$H$_5$) | | | |

Formulation Examples for use in Crop Protection (%=Percent by Weight)

Example F1: Emulsifiable concentrates

|  | a) | b) | c) |
|---|---|---|---|
| active ingredient | 25% | 40% | 50% |
| calcium dodecylbenzenesulfonate | 5% | 8% | 6% |
| castor oil polyethylene glycol ether (36 mol of ethylene oxide) | 5% | — | — |
| tributylphenol polyethylene glycol ether (30 mol of ethylene oxide) | — | 12% | 4% |
| cyclohexanone | — | 15% | 20% |
| xylene mixture | 65% | 25% | 20% |

Mixing together the finely ground active ingredient and additives yields an emulsifiable concentrate which, on dilution with water, yields emulsions of the desired concentration.

Example F2: Solutions

|  | a) | b) | c) | d) |
|---|---|---|---|---|
| active ingredient | 80% | 10% | 5% | 95% |
| ethylene glycol monomethyl ether | — | 20% | — | — |
| polyethylene glycol (MW 400) | — | 70% | — | — |
| N-methyl-2-pyrrolidone | 20% | 20% | 1% | 5% |
| epoxidised coconut oil | — | — | — | 1% |
| petroleum ethers (boiling range 160-190°) | — | — | 94% | — |

Mixing together the finely ground active ingredient and additives yields a solution suitable for application in the form of microdrops.

Example F3: Granules

|  | a) | b) | c) | d) |
|---|---|---|---|---|
| active ingredient | 5% | 10% | 8% | 21% |
| kaolin | 94% | — | 79% | 54% |
| highly disperse silicic acid | 1% | — | 13% | 7% |
| attapulgite | — | 90% | — | 18% |

The active ingredient is dissolved in dichloromethane, the solution is sprayed onto the carrier mixture, and the solvent is evaporated off in vacuo.

Example F4: Wettable powders

|  | a) | b) | c) |
|---|---|---|---|
| active ingredient | 25% | 50% | 75% |
| sodium lignosulfonate | 5% | 5% | — |
| sodium lauryl sulfate | 3% | — | 5% |
| sodium diisobutylnaphthalene-sulfonate | — | 6% | 10% |
| octylphenol polyethylene glycol ether (7-8 mol of ethylene oxide) | — | 2% | — |
| highly disperse silicic acid | 5% | 10% | 10% |
| kaolin | 62% | 27% | — |

Active ingredient and additives are mixed together and the mixture is ground in a suitable mill, yielding wettable powders which can be diluted with water to give suspensions of the desired concentration.

Example F5

Emulsifiable Concentrate

| active ingredient | 10% |
|---|---|
| octylphenol polyethylene glycol ether (4-5 mol of ethylene oxide) | 3% |
| calcium dodecylbenzenesulfonate | 3% |
| castor oil polyethylene glycol ether (36 mol of ethylene oxide) | 4% |
| cyclohexanone | 30% |
| xylene mixture | 50% |

Mixing together the finely ground active ingredient and additives yields an emulsifiable concentrate which, on dilution with water, yields emulsions of the desired concentration.

Example F6

Extruder Granules

| active ingredient | 10% |
|---|---|
| sodium lignosulfonate | 2% |
| carboxymethylcellulose | 1% |
| kaolin | 87% |

Active ingredient and additives are mixed together and the mixture is ground, moistened with water, extruded and granulated, and the granules are dried in a stream of air.

Example F7

Coated Granules

| active ingredient | 3% |
|---|---|
| polyethylene glycol (MW 200) | 3% |
| kaolin | 94% |

Uniform application of the finely ground active ingredient to the kaolin moistened with polyethylene glycol in a mixer yields non-dusty coated granules.

Example F8

Suspension Concentrate

| | |
|---|---|
| active ingredient | 40% |
| ethylene glycol | 10% |
| nonylphenol polyethylene glycol ether (15 mol of ethylene oxide) | 6% |
| sodium lignosulfonate | 10% |
| carboxymethylcellulose | 1% |
| aqueous formaldehyde solution (37%) | 0.2% |
| aqueous silicone oil emulsion (75%) | 0.8% |
| water | 32% |

Mixing together the finely ground active ingredient and additives yields a suspension concentrate which, on dilution with water, yields suspensions of the desired concentration.

Biological Examples

Example B1

Action Against *Spodoptera littoralis*

Young soybean plants are sprayed with an aqueous emulsion spray mixture comprising 12.5 ppm of active ingredient and, after the spray-coating has dried, are populated with 10 caterpillars of *Spodoptera littoralis* in the first stage and then placed in a plastics container. 3 days later, the percentage reduction in population and the percentage reduction in feeding damage (% activity) are determined by comparing the number of dead caterpillars and the feeding damage on the treated plants with that on untreated plants.

The compounds of the Tables exhibit good activity in this test. For example, especially compounds A.2, A.4, A.9, A.10, A.12, A.13, A.14, A.19, A.21 to A.25 and A.28 have activity of more than 90% in this test.

Example B2

Systemic Action Against *Spodoptera littoralis*

Maize seedlings are laid in the solution under test. 6 days later, the leaves are cut off and placed in a petri dish on moist filter paper and infested with from 12 to 15 larvae of *Spodoptera littoralis* in the $L_1$ stage. 4 days later, the percentage reduction in population (% activity) is determined by comparing the number of dead caterpillars on the treated plants with that on untreated plants.

The compounds of the Tables exhibit good activity in this test. For example, especially compounds A.5, A.9, A.10, A.13, A.14, A.19, A.22 to A.25 and A.28 have activity of more than 90% in this test.

Example B3

Action Against *Heliothis virescens*

30-35 eggs of *Heliothis virescens* that are from 0 to 24 hours old are deposited on filter paper lying in a petri dish on a layer of artificial nutrient. 0.8 ml of the solution under test is then pipetted onto the filter papers. Evaluation is carried out after 6 days. The percentage reduction in population (% activity) is determined by comparing the number of dead eggs and larvae on the filter papers with that on untreated filter papers.

The compounds of the Tables exhibit good activity in this test. For example, especially compounds A.2 and A.14 have activity of more than 90% in this test.

Example B4

Action Against *Plutella xylostella* Caterpillars

Young cabbage plants are sprayed with an aqueous emulsion spray mixture comprising 12.5 ppm of active ingredient and, after the spray-coating has dried, are populated with 10 caterpillars of *Plutella xylostella* in the first stage and then placed in a plastics container. Evaluation is carried out 3 days later. The percentage reduction in population and the percentage reduction in feeding damage (% activity) are determined by comparing the number of dead caterpillars and the feeding damage on the treated plants with that on untreated plants.

The compounds of Table 1 exhibit good activity against *Plutella xylostella* in this test. For example, especially compounds A.2, A.4, A.5, A.9, A.10, A.12, A.13, A.14, A.19, A.21 to A.25 and A.28 have activity of more than 90% in this test.

Example B5

Action Against *Diabrotica balteata*

Maize seedlings are sprayed with an aqueous emulsion spray mixture comprising 12.5 ppm of active ingredient and, after the spray-coating has dried, are populated with 10 *Diabrotica balteata* larvae in the second stage and then placed in a plastics container. 6 days later, the percentage reduction in population (% activity) is determined by comparing the number of dead larvae on the treated plants with that on untreated plants.

The compounds of the Tables exhibit good activity in this test. For example, especially compounds A.2, A.4, A.9, A.10, A.13, A.14, A.19 and A.23 have activity of more than 90% in this test.

Example B6

Action Against *Tetranychus urticae*

Young bean plants are populated with a mixed population of *Tetranychus urticae* and sprayed 1 day later with an aqueous emulsion spray mixture comprising 12.5 ppm of active ingredient, incubated for 6 days at 25° C. and then evaluated. The percentage reduction in population (% activity) is determined by comparing the number of dead eggs, larvae and adults on the treated plants with that on untreated plants.

The compounds of the Tables exhibit good activity in this test. For example, especially compounds A.2, A.4, A.5, A.9, A.10, A.13, A.14, A.19, A.21 to A.25 and A.28 have activity of more than 90% in this test.

What is claimed is:

1. A compound of formula

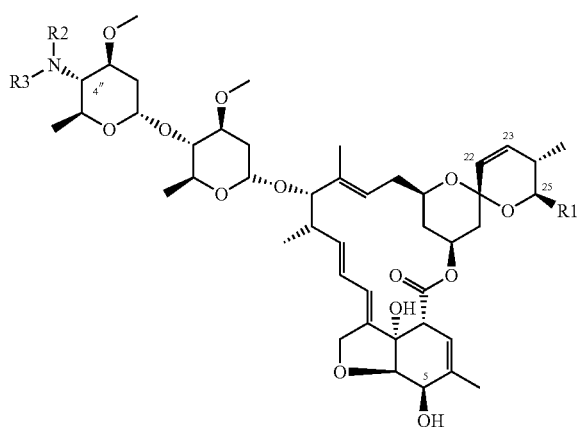

which in the 4''-position has the (S)-configuration and wherein
- $R_1$ is $C_3$-$C_8$ cycloalkyl or $C_2$-$C_{12}$ alkenyl;
- $R_2$ is hydrogen, or unsubstituted or mono- to penta-substituted $C_2$-$C_{12}$ alkenyl;
- $R_3$ is mono- to penta-substituted $C_1$-$C_{12}$ alkyl, unsubstituted or mono- to penta-substituted $C_3$-$C_{12}$ cycloalkyl, unsubstituted or mono- to penta-substituted $C_2$-$C_{12}$ alkenyl, unsubstituted or mono- to penta-substituted $C_4$-$C_{12}$ cycloalkenyl, unsubstituted or mono- to penta-substituted $C_2$-$C_{12}$ alkynyl; or
- $R_2$ and $R_3$ together are a three- to seven-membered alkylene bridge in each of which a $CH_2$ group may optionally be replaced by S or $NR_4$;

wherein the substituents of the mentioned alkyl, alkenyl, alkynyl, alkylene, alkenylene, cycloalkyl and cycloalkenyl radicals in $R_1$, $R_2$, $R_3$, and $R_2$ and $R_3$ together are selected from the group consisting of halogen, halo-$C_1$-$C_2$ alkyl, CN, SCN, $NO_2$, $Si(C_1$-$C_{12}$ alkyl$)_3$, $C_2$-$C_6$alkynyl, $C_3$-$C_8$ cycloalkyl that is unsubstituted or substituted by from one to three methyl groups, norbornylenyl, $C_3$-$C_8$ cycloalkenyl that is unsubstituted or substituted by from one to three methyl groups, $C_3$-$C_8$ halocycloalkyl, $C_1$-$C_{12}$ alkoxy, $C_1$-$C_6$ alkoxy-$C_1$-$C_6$ alkoxy, $C_3$-$C_8$ cycloalkoxy, $C_1$-$C_{12}$ haloalkoxy, $C_1$-$C_{12}$ alkylthio, $C_3$-$C_8$ cycloalkylthio, $C_1$-$C_{12}$ haloalkylthio, $C_1$-$C_{12}$ alkylsulfinyl, $C_3$-$C_8$ cycloalkylsulfinyl, $C_1$-$C_{12}$ haloalkylsulfinyl, $C_3$-$C_8$ halocycloalkylsulfinyl, $C_2$-$C_8$ alkenyl, $C_2$-$C_8$ alkynyl, NH(hydroxy-$C_1$-$C_6$ alkyl), N($C_1$-$C_6$ alkyl)(hydroxy-$C_1$-$C_6$ alkyl), N(phenyl)(hydroxy-$C_1$-$C_6$alkyl), —O—C(=X)N($R_8$)$R_6$, —NHC(=X)$R_6$, —NHC(=X)O$R_6$, —NHC(=X)S$R_6$, —NHC(=X)N($R_8$)$R_6$, —S—C(=S)$R_6$, —NHS(O)$_2$—$R_9$, —P(=O)(O$C_1$-$C_6$ alkyl)$_2$, aryl, heterocyclyl, and aryloxy, wherein said aryl, heterocyclyl, and aryloxy, are mono- to penta-substituted by substituents selected from the group consisting of OH, halogen, CN, $NO_2$, $C_1$-$C_{12}$ alkyl, hydroxyl-$C_1$-$C_{12}$ alkyl, $C_3$-$C_8$ cycloalkyl, $C_1$-$C_{12}$haloalkyl, $C_1$-$C_{12}$ alkoxy, $C_1$-$C_{12}$ haloalkoxy, $C_1$-$C_{12}$ alkylthio, $C_1$-$C_{12}$ haloalkylthio, $C_1$-$C_6$ alkoxy-$C_1$-$C_6$ alkyl, dimethylamino-$C_1$-$C_6$ alkoxy, $C_2$-$C_8$ alkenyl, $C_2$-$C_8$ alkynyl, $Si(C_1$-$C_{12}$ alkyl$)_3$, methylenedioxy, —C(=X)$R_5$, —O(=X)$R_6$, —$CH_2$—C(=O)$R_5$, —$CH_2$—C—C(=O)$R_6$, —NH—C(=X)$R_6$, —S—C(=S)$R_6$, $NH_2$, NH($C_1$-$C_{12}$ alkyl), —N($C_1$-$C_{12}$ alkyl)$_2$, $C_1$-$C_6$ alkylsulfinyl, $C_3$-$C_8$ cycloalkylsulfinyl, $C_1$-$C_6$ haloalkylsulfinyl, $C_3$-$C_8$ halocycloalkylsulfinyl, $C_1$-$C_6$ alkylsulfonyl, $C_3$-$C_8$ cycloalkylsulfonyl, $C_1$-$C_6$ haloalkylsulfonyl and $C_3$-$C_8$ halocycloalkylsulfonyl, unsubstituted phenyl, phenoxy, phenyl-$C_1$-$C_6$ alkyl, phenyl-$C_1$-$C_6$ alkoxy, phenyl-$C_2$-$C_6$ alkenyl, phenyl-$C_2$-$C_6$ alkynyl, phenyl, phenoxy, phenyl-$C_1$-$C_6$ alkyl, phenyl-$C_1$-$C_6$ alkoxy, phenyl-$C_2$-$C_6$ alkenyl and phenyl-$C_2$-$C_6$ alkynyl, each of which is substituted in the phenyl ring by from one to three substituents independently selected of one another from nitro, cyano, halogen, $C_1$-$C_{12}$ alkoxy, halo-$C_1$-$C_{12}$ alkyl and halo-$C_1$-$C_{12}$ alkoxy;

X is O or S;

$R_4$ is $C_1$-$C_8$ alkyl, $C_3$-$C_8$ cycloalkyl, $C_2$-$C_8$ alkenyl, $C_2$-$C_8$ alkynyl, benzyl or —C(=O—$R_5$;

$R_5$ is H, OH, SH, $C_1$-$C_{12}$alkyl, or $C_1$-$C_{12}$haloalkyl;

$R_6$ is H, $C_1$-$C_{24}$ alkyl, $C_1$-$C_6$ alkoxy-$C_1$-$C_6$ alkyl, $C_1$-$C_{12}$ hydroxyalkyl, $C_1$-$C_{12}$ haloalkyl, $C_2$-$C_8$ alkenyl, $C_2$-$C_8$ alkynyl, $C_3$-$C_8$ cycloalkyl, —$C_1$-$C_6S(O)_2$—$R_9$, aryl or phenyl-$C_1$-$C_6$ alkyl, wherein the phenyl- and aryl-radicals may carry from one to three substituents selected independently of one another from nitro, cyano, halogen, $C_1$-$C_6$ alkyl, $C_1$-$C_6$ alkoxy, $C_1$-$C_6$ haloalkyl and $C_1$-$C_6$haloalkoxy;

$R_7$ is H, OH, $C_1$-$C_{12}$ alkyl, $C_1$-$C_{12}$ alkoxy, $C_1$-$C_6$ alkoxy-$C_1$-$C_6$ alkoxy, $C_2$-$C_8$ alkenyloxy, phenyl, phenoxy, benzyloxy, $NH_2$, NH($C_1$-$C_{12}$ alkyl), N($C_1$-$C_{12}$ alkyl)$_2$, —NH-phenyl or —N($C_1$-$C_{12}$ alkyl)-phenyl;

$R_8$ is H, $C_1$-$C_{12}$ alkyl, phenyl or benzyl; and $R_9$ is H, $C_1$-$C_{12}$ alkyl, aryl, or aryl-$C_1$-$C_{12}$ alkyl, wherein the aryl radical may carry from one to three substituents selected independently of one another from nitro, cyano, halogen, $C_1$-$C_6$ alkyl, $C_1$-$C_6$ alkoxy, $C_1$-$C_6$ haloalkyl and $C_1$-$C_6$ haloalkoxy;

and, where appropriate, E/Z isomers, mixtures of E/Z isomers and/or tautomers thereof, in each case in free form or in salt form.

2. A compound according to claim 1 of the formula (I) in free form.

3. A compound according to claim 1 of the formula (I) in which $R_3$ is mono- to penta-substituted $C_1$-$C_{12}$ alkyl.

4. A pesticide composition which comprises at least one compound according to claim 1 of the formula (I), in free form or in agrochemically useable salt form, as active ingredient and at least one auxiliary.

5. A process for preparing a composition as described in claim 4, which comprises intimately mixing the active substance with the auxiliary or auxiliaries.

6. A method of controlling pests, which comprises applying a pesticidal composition as described in claim 4 to the pests or their habitat.

* * * * *

UNITED STATES PATENT AND TRADEMARK OFFICE
CERTIFICATE OF CORRECTION

| | | |
|---|---|---|
| PATENT NO. | : 7,605,134 B2 | Page 1 of 1 |
| APPLICATION NO. | : 10/488225 | |
| DATED | : October 20, 2009 | |
| INVENTOR(S) | : Hans Tobler | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1004 days.

Signed and Sealed this

Fifth Day of October, 2010

David J. Kappos
*Director of the United States Patent and Trademark Office*